United States Patent
Yamada et al.

(10) Patent No.: US 7,220,736 B2
(45) Date of Patent: *May 22, 2007

(54) PYRIMIDINE COMPOUNDS

(75) Inventors: Koichiro Yamada, Saitama-ken (JP); Kenji Matsuki, Saitama-ken (JP); Kenji Omori, Saitama (JP); Kohei Kikkawa, Kawaguchi (JP)

(73) Assignee: Tanabe Seiyaku Co., Ltd., Osaka (JP)

( * ) Notice: Subject to any disclaimer, the term of this patent is extended or adjusted under 35 U.S.C. 154(b) by 517 days.

This patent is subject to a terminal disclaimer.

(21) Appl. No.: 10/258,545

(22) PCT Filed: Mar. 15, 2001

(86) PCT No.: PCT/JP01/02034

§ 371 (c)(1), (2), (4) Date: Oct. 25, 2002

(87) PCT Pub. No.: WO01/83460

PCT Pub. Date: Nov. 8, 2001

(65) Prior Publication Data

US 2003/0229089 A1 Dec. 11, 2003

(30) Foreign Application Priority Data

Apr. 28, 2000 (JP) .............................. 2000-130371

(51) Int. Cl.
C07D 239/42 (2006.01)
C07D 401/12 (2006.01)
A61K 31/505 (2006.01)
C07D 471/04 (2006.01)

(52) U.S. Cl. ................ 514/211.1; 514/218; 514/235.8; 514/249; 514/255.05; 514/264.1; 514/274; 514/275; 540/548; 540/552; 540/575; 544/122; 544/279; 544/296; 544/317; 544/323; 544/324

(58) Field of Classification Search ................ 544/122, 544/279, 296, 317, 323, 324; 540/552, 548, 540/575; 514/211.1, 218, 235.8, 249, 255.05, 514/264.1, 274, 275
See application file for complete search history.

(56) References Cited

U.S. PATENT DOCUMENTS

| | | | |
|---|---|---|---|
| 3,560,624 A | 2/1971 | Rogers et al. | 424/310 |
| 4,464,457 A | 8/1984 | Bosse et al. | 430/288 |
| 4,704,459 A | 11/1987 | Todo et al. | 546/123 |
| 5,716,993 A | 2/1998 | Ozaki et al. | 514/619 |
| 6,432,963 B1 * | 8/2002 | Hisamichi et al. | 514/256 |
| 6,656,935 B2 * | 12/2003 | Yamada et al. | 514/230.5 |
| 6,797,709 B2 | 9/2004 | Yamada et al. | |

FOREIGN PATENT DOCUMENTS

| | | |
|---|---|---|
| AU | 199955977 A1 | 5/2000 |
| EP | 0 668 280 A1 | 3/1995 |
| EP | 0 722 936 A1 | 2/1996 |
| EP | 0 459 819 B1 | 8/1996 |
| EP | 0 995 750 A1 | 4/2000 |
| HU | 211 649 A9 | 6/1995 |
| JP | 95273 | 7/1975 |

(Continued)

OTHER PUBLICATIONS

Heaney et al., Pyrimidine annealated heterocycles—synthesis and cycloaddition of the first pyrimido[1,4]diazepine N-oxides, J. Chem. Soc., Perkin Trans. 1, (6) pp. 622-632, Feb. 2001.*

(Continued)

*Primary Examiner*—Deepak Rao
(74) *Attorney, Agent, or Firm*—Finnegan, Henderson, Farabow, Garrett & Dunner, L.L.P.

(57) ABSTRACT

A cyclic compound of the formula (I) or a pharmacologically acceptable salt thereof,

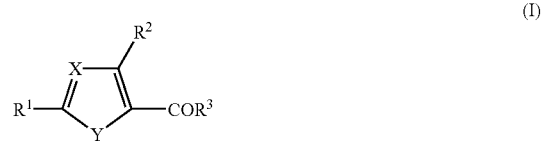

(I)

wherein X is =CH— or =N—, Y is —NH—, —NR$^4$—, —S—, —O—, —CH=N—, —N=CH—, —N=N—, —CH=CH—, etc., R$^1$ is a lower alkoxy group, an amino group, a heterocyclic ring containing N atom(s), or a hydroxy group substituted by a heterocyclic ring containing N atom(s) (each of which is optionally substituted), R$^2$ is a lower alkylamino group which is optionally substituted by an aryl group, a lower alkoxy group which is optionally substituted by an aryl group, a lower alkoxy group substituted by an aromatic heterocyclic ring containing N atom(s), R$^3$ is an aryl group, a heterocyclic ring containing N atom(s), a lower alkyl group, a lower alkoxy group, a cyclo lower alkoxy group, a hydroxy group substituted by a heterocyclic ring containing N atom(s), or an amino group (each of which is optionally substituted), and R$^3$ and a substituent in Y may be combined to form a lactone ring.

The compound of the present invention has excellent selective PDE V inhibitory activity and therefore, is useful as a therapeutic or prophylactic drug for treating various diseases due to functional disorders on cGMP-signaling.

8 Claims, No Drawings

FOREIGN PATENT DOCUMENTS

| | | |
|---|---|---|
| JP | 54 081299 | 6/1979 |
| JP | 2000-26294 | 1/2000 |
| WO | WO 94/28902 | 12/1994 |
| WO | WO 96/22991 | 8/1996 |
| WO | WO 98/23597 | 6/1998 |
| WO | WO 9931073 A1 * | 6/1999 |
| WO | WO 00/76980 A1 | 12/2000 |

OTHER PUBLICATIONS

Humburg et al., CAPLUS Abstract 100:6542, 1984.*

O'Brien et al., CAPLUS Abstract 59:54964, 1963.*

Nuss et al., CAPLUS Abstract No. 132:64265, 1999.*

Hisamichi et al., CAPLUS Abstract 131:44844, 1999.*

Yurugi et al., CAPLUS Abstract No. 72:55401, 1970.*

Kentaro Hirai et al., "Heterocyclic Cation Systems. 14.[1] Synthesis of Thieno[3,2-e][1,4]diazepine, Thiazolo[4,5-e][1,4]diazepine, and s-Triazolo[3,4-c]thiazolo[4,5-e][1,4]diazepine Derivatives," *J. Org. Chem.* 1980, 45, 253-260.

Mathias P. Mertes et al., "Approaches to the Synthesis of 1-Deazauridine and 2'-Deoxy-1-deazauridine[1]," *J. Med. Chem.*, (1967), vol. 10(2), 320-5, compound 16.

Dong Chan Kim et al., "Synthesis of new Pyrrolidine C-Nucleosides via Staudinger-aza-Wittig Cyclization of γ-Azido Ketone," *Tetrahedron Letters* 40 (1999) 4825-4828, compound 2.

Rebecca L. Chan et al., "the Chemistry of an Electron-Deficient 5-Deazaflavin. 8-Cyano-10-methyl-5-deazaisoalloxazine," *J. Am. Chem. Soc.* (1977), 99(20), 6721-30, compound IX.

Theunis G. van Aardt et al., "Direct Synthesis of Pterocarpans via Aldol Condensation of Phenylacetates with Benzaldehydes," *Tetrahedron* (1999), 55 (40), 11773-11786, *compound No. 6*.

Ann. Rept. Takeda Res. Lab. 28, pp. 1-11 (1969).

Life Sciences, 67, pp. 23-29 (2000).

J. Clin. Invest. 106, pp. 373-384 (2000).

Gastroenterology, 118, pp. 253-257 (2000).

Br. J. Pharmacol. 127, pp. 514-520 (1999).

Br. J. Pharmacol. 111, pp. 1198-1204 (1994).

J. Cell. Biochem. 77 pp. 159-167 (2000).

The Journal of Urology, Supplement. vol. 155, No. 5, pp. 495A739 (1996).

Bioorganic & Medicinal Chemistry Letters, vol. 6., No. 15, pp. 1819 (1996).

British Journal of Pharmacology, Proceeding Supplement, vol. 118, pp. 153 (1996).

The New England Journal of Medicine, vol. 338, No. 20, pp. 1397-1404 (1998).

Clinical Therapeutics, vol. 20, No. 6, pp. 1033-1048 (1998).

International Journal of Impotence Research, vol. 10, No. 2. pp. 69-73 (1998).

European Journal of Pharmacology, vol. 352, pp. 157-163 (1998).

J. Am. Chem. Soc. vol. 65, pp. 350 (1943).

Igor S. Kovalev et al., CAPLUS Abstract 134:193276, 2000.

* cited by examiner

PYRIMIDINE COMPOUNDS

TECHNICAL FIELD

The present invention relates to a novel cyclic compound exhibiting a cGMP specific phosphodiesterase (PDE) inhibitory activity (PDE V inhibitory activity) and being useful as a medicament, and a process for preparing the same.

BACKGROUND ART

In general, it is known that cGMP, which is an intracellular second messenger, is decomposed and inactivated by phosphodiesterase which is widely distributed in tissues of the living body, and when said PDE activity is inactivated, the level of cGMP in cells is increased, and as a result, various pharmacological activities, for example, relaxation of vascular smooth muscle, relaxation of bronchial smooth muscle, and inhibition of platelet aggregation are exhibited.

Moreover, it has been reported that such cGMP specific PDE inhibitors (i.e., PDE V inhibitors) are useful in the treatment of diseases caused by a functional disorder of cGMP-signaling, including hypertension, angina pectoris, myocardial infarction, chronic or acute heart failure, pulmonary hypertension, etc. (cf., PCT Patent Publication WO 96/05176, etc.), and prostatic hyperplasia (Australian Patent Publication No. 9955977). It has also been reported that PDE V inhibitors may be useful in the treatment of female sexual dysfunction (Vemulapalli et al., Life Sciences, 67, 23–29 (2000)), diabetic gastroparesis (Watkins et al., J. Clin. Invest. 106: 373–384 (2000)), achalasia (Bortolotti et al., Gastroenterology; 118: 253–257 (2000)), diarrhea (Mule et al., Br. J. Pharmacol., 127, 514–20 (1999)), constipation (Bakre et al., J. Cell. Biochem. 77: 159–167 (2000)) and asthma (Turner et al., Br. J. Pharmacol., 111, 1198–1204 (1994)).

Furthermore, it has been also reported that 1-[4-ethoxy-3-(6,7-dihydro-1-methyl-7-oxo-3-propyl-1H-pyrazolo[4,3-d]pyrimidin-5-yl)-phenylsulfonyl]-4-methylpiperazine [general name: Sildenafil] having PDE V inhibitory activity is useful in the treatment of diseases such as penile erectile dysfunction (copulative impotence), etc. (cf., Boolell et al., The Journal of Urology, Supplement, vol. 155, no. 5, p. 495A739 (1996); Terrett et al., Bioorganic & Medicinal Chemistry Letters, vol. 6, no. 15, p. 1819 (1996); and Ballard et al., British Journal of Pharmacology, Proceeding Supplement, vol. 118, p. 153 (1996)).

However, sildenafil has been reported to have side effects such as headache, facial suffusion, gut disorder, rhinitis, color sense disorder, penile erectile continuance, etc. (Irwin et al., The New England Journal of Medicine, vol. 338, no. 20, p. 1397–1404 (1998); Morales et al., International Journal of Impotence Research, vol. 10, no. 2, p. 69–73 (1998); and Goldenberg, Clinical Therapeutics, vol. 20, no. 6, p. 1033–1048 (1998)).

In addition, sildenafil has also been reported that the effects of sildenafil on light response of retina tissues and its PDE VI inhibitory activity correlate each other in the experiments on dogs (Morales et al., International Journal of Impotence Research, vol. 10, no. 2, p. 69–73 (1998)), while it has been reported that PDE VI on retina plays an importance role in the sensation of light (Morrales et al., International Journal of Impotence Research, vol. 10, no. 2, p. 69–73 (1998); Estrade et al., European Journal of Pharmacology, vol. 352, p. 157–163 (1998)).

DISCLOSURE OF INVENTION

An object of the present invention is to provide a novel cyclic compound showing an excellent phosphodiesterase V (PDE V) inhibitory activity, and being useful as a remedy for the prophylaxis or treatment of penile erectile dysfunction with few side effects. Another object of the present invention is to provide a process for preparing such a cyclic compound.

The present invention is to provide a cyclic compound of the formula (I) or a pharmacologically acceptable salt thereof,

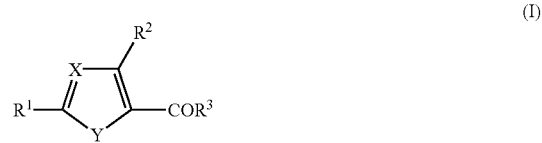

wherein X is =CH— or =N—,
Y is —NH—, —NR$^4$—, —S—, —O—, —CH=N—, or —N=CH—, —N=N—, —CH=CH—,

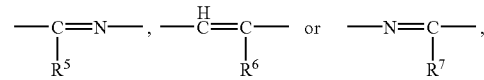

R$^1$ is a lower alkoxy group which is optionally substituted, an amino group which is optionally substituted, a heterocyclic ring containing N atom(s) which is optionally substituted, a hydroxy group which is optionally substituted by a heterocyclic ring containing N atom(s) which is optionally substituted, or cyno group, R$^2$ is a lower alkylamino group which is optionally substituted by an aryl group which is optionally substituted, a lower alkoxy group which is optionally substituted by an aryl group which is optionally substituted, a lower alkoxy group substituted by an aromatic heterocyclic ring containing N atom(s), a lower alkylamino group substituted by a heterocyclic ring which is optionally substituted, or an amino group substituted by an aryl group which is optionally substituted, R$^3$ is an aryl group which is optionally substituted, a heterocyclic ring containing N atom(s) which is optionally substituted, a lower alkyl group which is optionally substituted, a lower alkoxy group which is optionally substituted, a cyclo lower alkoxy group which is optionally substituted, a hydroxy group substituted by a heterocyclic ring containing N atom(s) which is optionally substituted, or an amino group which is optionally substituted, and R$^4$, R$^5$, R$^6$ or R$^7$ is an aryl group which is optionally substituted, a heterocyclic ring containing N atom(s) which is optionally substituted, a lower alkoxy group which is optionally substituted, or an amino group which is optionally substituted, and R$^4$, R$^5$, R$^6$ or R$^7$ may combine with R$^3$ to form a lactone ring represented by the following formula,

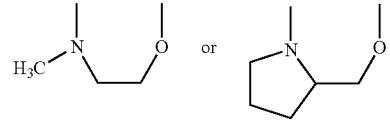

wherein, when X is =N—, Y is —CH=N—, or —N=CH—, R² is an amino group mono-substituted by a methyl group substituted by an aryl which is optionally substituted, and R³ is a lower alkyl which is optionally substituted, an amino group mono-substituted by a lower alkyl group substituted by a heterocyclic ring containing N atom(s) which is optionally substituted, an amino group mono-substituted by a heterocyclic ring containing N atom(s) which is optionally substituted or an amino group mono-substituted by a cyclo lower alkyl group which is optionally substituted, R¹ is a lower alkoxy group which is optionally substituted, an amino group which is optionally substituted, a hydroxy group which is optionally substituted by a heterocyclic ring containing N atom(s) which is optionally substituted, or cyano group.

THE BEST MODE FOR CARRYING OUT THE INVENTION

As a ring represented by the following formula in the compound (I),

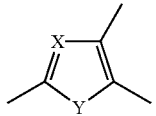

wherein X and Y are the same as defined above, is illustrated benzene ring or a 5–6 membered monocyclic hetero ring containing N atom(s), such as phenyl group, or a 5–6 membered aromatic monocyclic hetero ring (e.g. pyrrolyl, thienyl, furyl, imidazolyl, thiazolyl, oxazolyl, pyridyl, pyrimidinyl, pyridazinyl, 1,2,4-triazinyl).

As "a lower alkoxy group which is optionally substituted", represented by R¹, is illustrated a lower alkoxy group which is optionally substituted by one to three, same or different substituents selected from the group consisting of an cyclo lower alkyl group, hydroxy group, a lower alkylamino group which is optionally protected, a lower alkoxy group, a lower alkyl group substituted by hydroxy group, an aryl group, a lower alkoxyaryl group, a lower alkylaryl group substituted by hydroxy group, an aryl group substituted by halogen atom(s), furyl group, pyridyl group, a lower alkoxypyridyl group, a lower alkylpyridyl group substituted by hydroxy group, a lower alkylpyridyl group, a pyrimidinyl group, a lower alkoxypyrimidinyl group, and a morphorinyl group.

As "an amino group which is optionally substituted", represented by R¹, is illustrated a lower alkylamino group which is optionally substituted by one to three, same or different substituents selected from the group consisting of a hydroxy group, a lower alkoxy group, a pyridyl group, a lower alkylamino group, cyano group, phenyl group, a phenyl group which is optionally substituted by a lower alkoxy group and/or a halogen atom, an indanyl group and a lower alkyl group substituted by hydroxy group, or an indanylamino group.

As a heterocyclic ring containing N atom(s) of "a heterocyclic ring containing N atom(s) which is optionally substituted", represented by R¹, is illustrated a 5–14 membered mono- or bi-cyclic hetero ring containing N atom(s), more concretely a 5–6 membered monocyclic hetero ring containing N atom(s), or a 8–12 membered bicyclic hetero ring containing N atom(s), furthermore concretely, a 5–6 membered non-aromatic monocyclic hetero ring containing N atom(s), such as a pyrrolidinyl group, a piperazinyl group, a piperidyl group, or a 8–10 membered bicyclic hetero ring containing N atom(s) formed by fusing above mentioned mono- 5–6 membered non-aromatic hetero ring containing N atom(s) together with a mono- 5–6 membered aromatic ring containing N atom(s), such as 1H-2,3-dihydropyrrolo[3,4-b]pyridin-2-yl, 5,6,7,8-tetrahydroimidazo[1,2-a]pyrazin-7-yl or 5,6,7,8-tetrahydro-1,7-naphthyridin-7-yl. These heterocyclic rings containing N atom(s) are optionally substituted by one to four, same or different substituents selected from the group consisting of hydroxy group, an amino group which is optionally protected, a lower alkyl group, a lower alkoxy group, a lower alkoxycarbonyl group, a lower alkyl group substituted by hydroxy group, oxo group, a pyridyl group, a pyrimidinyl group, formyl group, mesyl, a lower alkanoyl group substituted by hydroxy group which is optionally protected, a lower alkoxy-substituted lower alkyl group, a carbamoyl group, a benzylamino group in which the benzene ring is substituted by a lower alkoxy group, and a benzylamino group in which the benzene ring is substituted by a halogen atom.

As "a hydroxy group which is optionally substituted by a heterocyclic ring which is optionally substituted", represented by R¹, is illustrated a hydroxy group which is optionally substituted by a hetero cyclic ring containing N atom(s) selected from the group consisting of a piperidyl group, a lower alkyl piperidyl group and a pyridyl group.

As an aryl group of "an aryl which is optionally substituted", represented by R², is illustrated a 5–10 membered mono- or bicyclic aromatic hydrocarbon ring, more concretely phenyl group or naphthyl group. As a substituent of "an aryl group which is optionally substituted", in case of "a lower alkylamino group which is optionally substituted by an aryl group which is optionally substituted", is one to four, same or different, groups selected from a lower alkoxy group, a halogen atom, an amino group which is optionally protected, hydroxy group, a lower alkoxypyridyl group, a lower alkylamino group which is optionally protected, nitro group, a lower alkyl group substituted by a halogen atom, a lower alkylenedioxy group, cyano group, a lower alkyl group substituted by a hydroxy group which is optionally protected, a lower alkylsulfonyl group and a lower alkylsulfinyl group. In case of "a lower alkoxy group which is optionally substituted by an aryl group which is optionally substituted", said aryl group is optionally substituted by one to four, same or different, substituents selected from the group consisting of a lower alkoxy group, a halogen atom and cyano group.

As "a lower alkoxy group substituted by an aromatic heterocyclic ring containing N atom(s)", represented by R², is illustrated a lower alkoxy group substituted by one to three, same or different, aromatic heterocyclic rings containing N atom(s) selected from the group consisting of a pyridyl group, a pyrimidinyl group and a pyrazinyl group.

As "a lower alkylamino group substituted by a heterocyclic ring which is optionally substituted", represented by R², is illustrated a lower alkylamino group substituted by one to four, same or different, heterocyclic rings which are optionally substituted selected from the group consisting of an indolyl group, a pyrimidinyl group, a benzofuranyl group, a dihydrobenzofuranyl group, a lower alkylpyrimidinyl group, a dihydrobenzoxazolyl group and a dihydrobenzoimidazolyl group.

As "an aryl group which is optionally substituted", represented by R³, is illustrated an aryl group which is optionally substituted by one to four, same or different, substituents selected from a lower alkoxy group and a lower alkylamino group, or an aryl group which is optionally substituted by one or two lower alkylenedioxy groups. As "an aryl group", is illustrated a 5–10 membered mono- or bicyclic aromatic hydrocarbon, such as phenyl group or naphthyl group.

As a heterocyclic ring containing N atom(s) of "a heterocyclic ring containing N atom(s) which is optionally substituted", represented by $R^3$, is illustrated a 5–6 membered monocyclic herero ring containing N atom(s), such as a 5–6 membered non-aromatic monocyclic hetero ring containing N atom(s), e.g. a piperidyl group, a piperazinyl group, or a morpholinyl group, or such as a 5–6 membered aromatic monocyclic hetero ring containing N atom(s), e.g. a pyrimidinyl group, a pyridazinyl group, a pyridyl group or an imidazolyl group. Said heterocyclic ring containing N atom(s) is optionally substituted by one to four, same or different, substituents selected from the group consisting of a lower alkyl group, hydroxy group, an amino group, chlorosulfinyloxy group and piperidinyloxysulfinyloxy group.

As "a lower alkyl group which is optionally substituted", represented by $R^3$, is illustrated a lower alkyl group which is optionally substituted by one to three, same or different, substituents selected from the group consisting of a morpholinyl group, a pyridyl group, a lower alkylsulfonyl group and a di-lower alkoxyphosphoryl group.

As "a lower alkoxy group which is optionally substituted", represented by $R^3$, is illustrated a lower alkoxy group which is optionally substituted by one to three, same or different, substituents selected from the group consisting of a pyridyl group, a lower alkoxypyridyl group, a pyrimidinyl group, a lower alkylamino group, a pyrazinyl group, a lower alkoxy group which is optionally substituted by a phenyl group, a pyrimidinyl-substituted oxy group, a pyridyl-substituted oxy group, a pyrimidinyl-substituted lower alkoxy group, a morpholinyl group, a lower alkylmorpholinyl group, a N-lower alkyl-N-pyrimidinylamino group, a di-lower alkyldioxolanyl group, a lower alkoxy lower alkoxy group, a pyridylcarbonylamino group, hydroxy group, a piperidyl group and a lower alkylpiperidyl group.

As "a cyclo lower alkoxy group which is optionally substituted", represented by $R^3$, is illustrated a cyclo lower alkoxy group which is optionally substituted by hydroxy group.

As "a hydroxy group substituted by a heterocyclic ring containing N atom(s) which is optionally substituted", represented by $R^3$, is illustrated a hydroxy group substituted by a heterocyclic ring containing N atom(s) which is optionally substituted by one to four, same or different, substituents selected from a pyrimidinyl group and cyano-substituted lower alkyl group.

As "an amino group which is optionally substituted", represented by $R^3$, is illustrated an amino group which is optionally substituted by one or two, same or different, substituents selected from the group consisting of (i) a lower alkoxy group which is optionally substituted by a lower alkoxy group, (ii) a lower alkyl group which is optionally substituted by one to three, same or different, substituents selected from the group consisting of cyano group, hydroxy group, a lower alkoxy group, a phenyl group which is optionally substituted by a lower alkoxy group and/or a halogen atom, carbamoyl group, a lower alkylamino group, a pyridyl group, a lower alkylpyridyl group, a lower alkoxypyridyl group, a pyrimidinyl group, a lower alkoxypyrimidinyl group, a morpholinyl group, a lower alkylmorpholinyl group, a hydroxy-substituted lower alkylmorpholinyl group, a cyano-substituted lower alkylmorpholonyl group, a hydroxy-substituted piperidyl group, an oxo-substituted piperazinyl group, a lower alkylpiperazinyl group, a lower alkylsulfonylpiperazinyl group, a pyrrolidinyl group, a lower alkylpyrrolidinyl group, a lower alkylpirazinyl group, a tetrahydrofuranyl group, a lower alkoxyphenoxy group, a lower alkoxypyridylamino group and a pyrimidinylamino group, (iii) phenyl group which is optionally substituted by hydroxy group or a lower alkoxy group, (iv) a pyridyl group which is optionally substituted by a lower alkyl group, (v) a pyrimidinyl group, (vi) a pyrazolyl group which is optionally substituted by a lower alkyl group, (vii) an isoxazolyl group which is optionally substituted by a lower alkyl group, (viii) a benz[b]morpholinyl group which is optionally substituted by oxo group, (ix) a morpholinyl group, (x) a piperidyl group which is optionally substituted by one to four, same or different, substituents selected from the group consisting of a lower alkoxycarbonyl group, a lower alkyl sulfonyl, a lower alkyl group, a cyano-substituted lower alkyl group, a hydroxy-substituted lower alkanoyl group, formyl group, a lower alkoxy-substituted lower alkanoyl group and a lower alkylamino-substituted lower alkanoyl group, (xi) a cyclo lower alkyl group which is optionally substituted by one to three, same or different, substituents selected from hydroxy group which is optionally protected, a lower alkoxy group and a pyrimidinyl-substituted oxy group, and (xii) a pyrimidinylamino group which is optionally substituted by a lower alkyl group and a lower alkoxycarbonyl group.

Further, as a protective group of an amino group, a lower alkylamino group and hydroxyl group, is illustrated formyl group, a lower alkanoyl group, etc.

In substituents represented by $R^4$, $R^5$, $R^6$ or $R^7$, as "an aryl group which is optionally substituted", is illustrated a phenyl group which is optionally substituted by a lower alkoxy group, as "a hererocyclic ring containing N atom(s) which is optionally substituted", is illustrated a heterocyclic ring containing N atom(s) which is optionally substituted by hydroxy group, a lower alkyl group or a hydroxy-substituted lower alkyl group, as "a heterocyclic ring containing N atom(s)", is illustrated a 5–14 membered monocyclic or bicyclic hetero ring, more concretely, a 5–6 membered monocyclic hetero ring containing N atom(s) or a 8–12 membered bicyclic hetero ring containing N atom(s), further more concretely, a 5–6 membered non-aromatic monocyclic hetero ring containing N atom(s), such as a pyrrolidinyl group, piperazinyl group, a piperidyl group, or a 8–10 membered bicyclic hetero ring containing N atom(s), which is a 5–6 membered aromatic monocyclic hetero ring containing N atom(s) fused to the above 5–6 membered non aromatic monocyclic hetero ring containing N atom(s), such as 1H-2,3-dihydropyrrolo[3,4-b]pyridin-2-yl, 5,6,7,8-tetrahydroimidazo[1,2-a]pyrazin-7-yl, 5,6,7,8-tetrahydro-1,7-naphthylidin-7-yl, etc., as "a lower alkoxy which is optionally substituted", is illustrated a lower alkoxy group, and as "an amino group which is optionally substituted", is illustrated an amino group which is optionally substituted by a lower alkyl group substituted by a heterocyclic ring containing N atom(s), a hydroxy-substituted cyclo lower alkyl group or a lower alkyl group. $R^4$, $R^5$, $R^6$ or $R^7$ can combine with $R^3$ to form a lactone ring represented by the following formula,

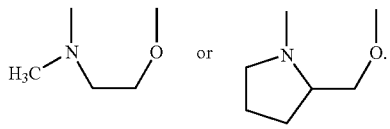

In the above compounds of the present invention, in case of the number of the substituent being not specified, the substituent includes plural substituents (for example, the expression "lower alkylamino group" means mono and di lower alkylamino groups.).

In the present specification, a lower alkyl group means a $C_1$–$C_6$ straight or branched alkyl group, such as methyl, ethyl, propyl, isopropyl, butyl, iso-butyl, tert-butyl, etc. A lower alkoxy group means a $C_1$–$C_6$ straight or branched alkoxy group, such as methoxy, ethoxy, propoxy, isopropyloxy, butyloxy, iso-butyloxy, tert-butyloxy, etc. A lower alkanoyloxy group means a $C_2$–$C_7$ straight or branched alkanoyl group, such as actetyl, propionyl, butyryl, etc. A cycloalkyl group means a $C_3$–$C_8$ cycloalkyl group, such as cyclopropyl, cyclobutyl, cyclopentyl, cyclohexyl, cycloheptyl, etc. A lower alkylene means a $C_1$–$C_6$ straight or branched alkylene group, such as methylene, ethylene, trimethylene, etc. An aryl group means a $C_6$–$C_{14}$ mono-, bi- or tri-cyclic aryl group (including a partially suturated ring), such as phenyl, naphthyl, indolyl, indanyl, etc. A hetero cyclic ring containing N atom(s) means a 5–14 membered mono- or bi-cyclic hetero ring containing N atom(s).

Preferable compounds (I) of the present invention are compounds (I) wherein
X is =N—,
Y is —NH—, —NR$^4$—, —S—, —O—, —CH=N—, —N=CH—, —N=N—, —CH=CH—,

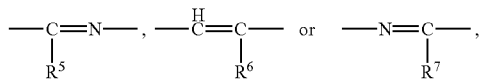

R$^1$ is a lower alkoxy group which is optionally substituted, an amino group which is optionally substituted, a heterocyclic ring containing N atom(s) which is optionally substituted, a hydroxy group which is optionally substituted by a heterocyclic ring containing N atom(s) which is optionally substituted, or cyano group, R$^2$ is a lower alkylamino group which is optionally substituted by an aryl group which is optionally substituted, a lower alkoxy group which is optionally substituted by an aryl group which is optionally substituted, a lower alkoxy group substituted by an aromatic heterocyclic ring containing N atom(s) which is optionally substituted, a lower alkylamino group substituted by a heterocyclic ring which is optionally substituted, or an amino group substituted by an aryl group which is optionally substituted, R$^3$ is an aryl group which is optionally substituted, a heterocyclic ring containing N atom(s) which is optionally substituted, a lower alkyl group which is optionally substituted, a lower alkoxy group which is optionally substituted, a cyclo lower alkoxy group which is optionally substituted, a hydroxy group substituted by a heterocyclic ring containing N atom(s) which is optionally substituted, or an amino group which is optionally substituted, and R$^4$, R$^5$, R$^6$ or R$^7$ is an aryl group which is optionally substituted, a heterocyclic ring containing N atom(s) which is optionally substituted, a lower alkoxy group which is optionally substituted or an amino group which is optionally substituted, and R$^4$, R$^5$, R$^6$ or R$^7$ optionally combines with R$^3$ to form a lactone ring represented by the following formula,

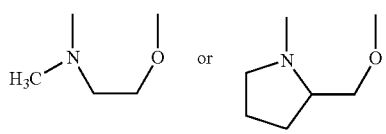

wherein, when X is =N—, Y is —CH=N—, or —N=CH—, R$^2$ is an amino group mono-substituted by a methyl group substituted by an aryl which is optionally substituted, and R$^3$ is a lower alkyl which is optionally substituted, an amino group mono-substituted by a lower alkyl group substituted by a heterocyclic ring containing N atom(s) which is optionally be substituted, or an amino group mono-substituted by a cyclo lower alkyl group which is optionally substituted, R$^1$ is a lower alkoxy which is optionally substituted, an amino group which is optionally substituted, a hydroxy group which is optionally substituted by a heterocyclic ring containing N atom(s) which is optionally substituted, or cyano group.

Other preferable compounds (I) of the present invention are compounds (I) wherein
X is =CH— or =N—,
Y is —NH—, —NR$^4$—, —S—, or —O—,
R$^1$ is a lower alkoxy group which is optionally substituted, an amino group which is optionally substituted, a heterocyclic ring containing N atom(s) which is optionally substituted, a hydroxy group which is optionally substituted by a heterocyclic ring containing N atom(s) which is optionally substituted, or cyano group, R$^2$ is a lower alkylamino group which is optionally substituted by an aryl group which is optionally substituted, a lower alkoxy group which is optionally substituted by an aryl group which is optionally substituted, a lower alkoxy group substituted by an aromatic heterocyclic ring containing N atom(s) which is optionally substituted, a lower alkylamino group substituted by a heterocyclic ring which is optionally substituted, or an amino group substituted by an aryl group which may substituted, R$^3$ is an aryl group which is optionally substituted, a heterocyclic ring containing N atom(s) which is optionally substituted, a lower alkyl group which is optionally substituted, a lower alkoxy group which is optionally substituted, a cyclo lower alkoxy group which is optionally substituted, a hydroxy group substituted by a heterocyclic ring containing N atom(s) which is optionally substituted, an amino group which is optionally substituted, or R$^4$ is an aryl group which is optionally substituted, a heterocyclic ring containing N atom(s) which is optionally substituted, a lower alkoxy group which is optionally substituted, or an amino group which is optionally substituted, and R$^4$ optionally combines with R$^3$ to form a lactone ring represented by following formula,

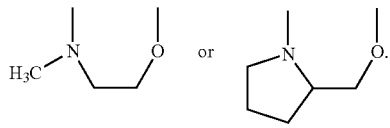

Preferable compounds (I) of the present invention are compounds (I) wherein
X is =N—,
Y is —N=N—, —CH=CH—,

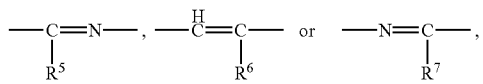

R¹ is a lower alkoxy group which is optionally substituted, an amino group which is optionally substituted, a heterocyclic ring containing N atom(s) which is optionally substituted, a hydroxy group which is optionally substituted by a heterocyclic ring containing N atom(s) which is optionally substituted, or cyano group, R² is a lower alkylamino group which is optionally substituted by an aryl group which is optionally substituted, a lower alkoxy group which is optionally substituted by an aryl group which is optionally substituted, a lower alkoxy group substituted by an aromatic heterocyclic ring containing N atom(s) which is optionally substituted, a lower alkylamino group substituted by a heterocyclic ring which is optionally substituted, or an amino group substituted by an aryl group which is optionally substituted, R³ is an aryl group which is optionally substituted, a heterocyclic ring containing N atom(s) which is optionally substituted, a lower alkyl group which is optionally substituted, a lower alkoxy group which is optionally substituted, a cyclo lower alkoxy group which is optionally substituted, a hydroxy group substituted by a heterocyclic ring containing N atom(s) which is optionally substituted, an amino group which is optionally substituted, or R⁵, R⁶ or R⁷ is an aryl group which is optionally substituted, a heterocyclic ring containing N atom(s) which is optionally substituted, a lower alkoxy group which is optionally substituted, or an amino group which is optionally substituted, and R⁵, R⁶ or R⁷ optionally combines with R³ to form a lactone ring represented by the following formula,

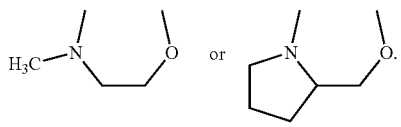

Preferable compounds (I) of the present invention are compounds (I) wherein
X is =N—,
Y is —CH=N— or —N=CH—,
R¹ is a lower alkoxy group which is optionally substituted, an amino group which is optionally substituted, a heterocyclic ring containing N atom(s) which is optionally substituted, a hydroxy group which is optionally substituted by a heterocyclic ring containing N atom(s) which is optionally substituted, or cyano group, R² is a lower alkylamino group which is optionally substituted by an aryl group which is optionally substituted, a lower alkoxy group which is optionally substituted by an aryl group which is optionally substituted, a lower alkoxy group substituted by an aromatic heterocyclic ring containing N atom(s) which is optionally substituted, a lower alkylamino group substituted by a heterocyclic ring which is optionally substituted, or an amino group substituted by an aryl group which is optionally substituted, R³ is an aryl group which is optionally substituted, a heterocyclic ring containing N atom(s) which is optionally substituted, a lower alkyl group which is optionally substituted, a lower alkoxy group which is optionally substituted, a cyclo lower alkoxy group which is optionally substituted, a hydroxy group substituted by a heterocyclic ring containing N atom(s) which is optionally substituted, an amino group which is optionally substituted, provided that when R² is an amino group mono-substituted by methyl group substituted by an aryl group which is optionally substituted, R³ is a lower alkyl group which is optionally substituted, an amino group mono-substituted by a lower alkyl group substituted by a heterocyclic ring containing N atom(s) which is optionally substituted, an amino group mono-substituted by a heterocyclic ring containing N atom(s) which is optionally substituted, or an amino group mono-substituted by a cycloalkyl group which is optionally substituted, R¹ is a lower alkoxy group which is optionally substituted, an amino group which is optionally substituted, a hydroxy group which is optionally substituted by a heterocyclic ring containing N atom(s) which is optionally substituted, or cyano group.

Preferable compounds (I) of the present invention are compounds (I) wherein
X is =CH—,
Y is —C=N—, —N=CH—, —N=N—,

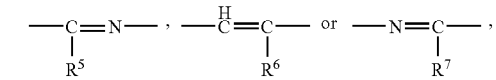

R¹ is a lower alkoxy group which is optionally substituted, an amino group which is optionally substituted, a heterocyclic ring containing N atom(s) which is optionally substituted, a hydroxy group which is optionally substituted by a heterocyclic ring containing N atom(s) which is optionally substituted, or cyano group, R² is a lower alkylamino group which is optionally substituted by an aryl group which is optionally substituted, a lower alkoxy group which is optionally substituted by an aryl group which is optionally substituted, a lower alkoxy group substituted by an aromatic heterocyclic ring containing N atom(s) which is optionally substituted, a lower alkylamino group substituted by a heterocyclic ring which is optionally substituted, or an amino group substituted by an aryl group which may substituted, R³ is an aryl group which is optionally substituted, a heterocyclic ring containing N atom(s) which is optionally substituted, a lower alkyl group which is optionally substituted, a lower alkoxy group which is optionally substituted, a cyclo lower alkoxy group which is optionally substituted, a hydroxyl group substituted by a heterocyclic ring containing N atom(s) which is optionally substituted, an amino group which is optionally substituted, or R⁵, R⁶ or R⁷ is an aryl group which is optionally substituted, a heterocyclic ring containing N atom(s) which is optionally substituted, a lower alkoxy group which is optionally substituted, or an amino group which is optionally substituted, and R⁵, R⁶ or R⁷ may combine with R³ to form a lactone ring represented by following formula,

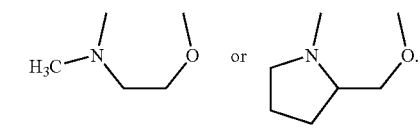

Preferable compounds (I) of the present invention are compounds (I) wherein
X is =CH—,
Y is —CH=CH—, $R^1$ is a lower alkoxy group which is optionally substituted, an amino group which is optionally substituted, a heterocyclic ring containing N atom(s) which is optionally substituted, a hydroxy group which is optionally substituted by a heterocyclic ring containing N atom(s) which is optionally substituted, or cyano group, $R^2$ is a lower alkylamino group which is optionally substituted by an aryl group which is optionally substituted, a lower alkoxy group which is optionally substituted by an aryl group which is optionally substituted, a lower alkoxy group substituted by an aromatic heterocyclic ring containing N atom(s) which is optionally substituted, a lower alkylamino group substituted by a heterocyclic ring which is optionally substituted, or an amino group substituted by an aryl group which is optionally substituted, $R^3$ is an aryl group which is optionally substituted, a heterocyclic ring containing N atom(s) which is optionally substituted, a lower alkyl group which is optionally substituted, a lower alkoxy group which is optionally substituted, a cyclo lower alkoxy group which is optionally substituted, a hydroxy group substituted by a heterocyclic ring containing N atom(s) which is optionally substituted, an amino group which is optionally substituted.

Preferable compounds (I) of the present invention are compounds (I) wherein $R^1$ is (1) a lower alkoxy group which is optionally substituted by one to three, same or different, substituents selected from the group consisting of a cyclo lower alkyl group, hydroxy group, a lower alkylamino group which is optionally protected, a lower alkoxy group, a hydroxy-substituted lower alkyl group, phenyl group, a lower alkoxyphenyl group, a hydroxy-substituted lower alkylphenyl group, a furyl group, a pyridyl group, a lower alkoxypyridyl group, a hydroxy-substituted lower alkylpyridyl group, a lower alkylpyridyl group, a pyrimidinyl group, a lower alkoxypyrimidinyl group, and a morpholinyl group, (2) a lower alkylamino group which is optionally substituted by one to three, same or different, substituents selected from the group consisting of hydroxy group, a lower alkoxy group, a lower alkyl group, a pyridyl group, a lower alkylamino group, cyano group, a phenyl group which is optionally substituted by a lower alkoxy group and/or a halogen atom, and a hydroxy-substituted lower alkyl group, (3) an indanylamino group, (4) a heterocyclic ring containing N atom(s) which is optionally substituted by one to four, same or different, substituents selected from the group consisting of hydroxyl group, a lower alkyl group, a lower alkoxy group, a hydroxy-substituted lower alkyl group, oxo group, a pyridyl group which is optionally substituted by a hydroxy-substituted lower alkyl group, a pyrimidinyl group which is optionally substituted by a lower alkylamino group, formyl group, mesyl group, a lower alkanoyl group substituted by a hydroxy group which is optionally protected, and carbamoyl group, (5) a hydroxy group which is optionally substituted by a pyridyl group, or (6) cyano group, $R^2$ is (1) a lower alkylamino group substituted by an aryl group which is optionally substituted by one to four, same or different, substituents selected from the group consisting of a lower alkoxy group, a halogen atom, an amino group, a lower alkanoylamino group, a formylamino group, hydroxy group, a lower alkoxypyridyl group, a lower alkylamino group, nitro group, a halogeno-substituted lower alkyl group, a lower alkylenedioxy group, cyano group, a lower alkyl group substituted by a hydroxy group which is optionally protected, a lower alkylsulfonyl group, and a lower alkylsulfinyl group, (2) a lower alkoxy group substituted by one to four, same or different, substituents selected from the group consisting of a lower alkoxy group and a halogen atom, (3) a lower alkoxy group substituted by a pyridyl group, (4) a lower alkylamino group substituted by an indolyl group, a pyrimidinyl group, a benzofuranyl group, a dihydrobenzofuranyl group, a lower alkylpyrimidinyl group, a dihydrobenzoxazolyl or a dihydrobenzimidazolyl group, or (5) an indanylamino group, $R^3$ is (1) an aryl group which is optionally substituted by one to four, same or different, substituents selected from the group consisting of a lower alkoxy group and an lower alkylamino group, or an aryl group which is optionally substituted by one or two lower alkylenedioxy groups, (2) a heterocyclic ring containing N atom(s) which is optionally substituted by one to four, same or different, substituents selected from the group consisting of a lower alkyl group, hydroxy group, an amino group, chlorosulfinyloxy group and a piperidinyloxysulfinyloxy group, (3) a lower alkyl group which is optionally substituted by one to three, same or different, substituents selected from the group consisting of a morpholinyl group and a di-lower alkoxyphosphoryl group, (4) a lower alkoxy group which is optionally substituted by one to three, same or different, substituents selected from the group consisting of a pyridyl group, a lower alkoxypyridyl group, a pyrimidinyl group, a lower alkylamino group, a pyrazinyl group, a lower alkoxy group which is optionally substituted by phenyl group, a pyrimidinyl-substituted oxy group, a pyridyl-substituted oxy group, a pyrimidinyl-substituted lower alkoxy group, a morpholinyl group, a lower alkylmorpholinyl group, a N-lower alkyl-N-pyrimidinylamino group, a lower alkyldioxolanyl group, a lower alkoxy-substituted lower alkoxy group, a pyridylcarbonylamino group, hydroxy group, and a lower alkylpiperidyl group, (5) a cyclo lower alkoxy group which is optionally substituted by hydroxy group, (6) a piperidyl-substituted hydroxy group which is optionally substituted by one to four, same or different, substituents selected from the group consisting of a pyrimidinyl group, a lower alkyl group and a cyano-substituted lower alkyl group, or (7) an amino group which is optionally substituted by one or two, same or different, substituents selected from the group consisting of (i) a lower alkoxy group which is optionally substituted by a lower alkoxy group, (ii) a lower alkyl group which is optionally substituted by one to three, same or different, substituents selected from the group consisting of cyano group, hydroxy group, a lower alkoxy group, a phenyl group which is optionally substituted by a lower alkoxy group and/or a halogen atom, carbamoyl group, a lower alkylamino group, a pyridyl group, a lower alkyl pyridyl group, a lower alkoxy pyridyl group, a pyrimidinyl group, a lower alkoxy pyrimidinyl group, a morpholinyl group, a lower alkyl morpholinyl group, a hydroxy-substituted lower alkyl morpholinyl group, a cyano-substituted lower alkylmorpholinyl group, a hydroxy-substituted piperidyl group, an oxo-substituted piperazinyl group, a lower alkyl piperazinyl group, a lower alkylsulfonylpiperazinyl group, a pyrrolidinyl group, a lower alkylpyrrolidinyl group, a lower alkylpyrazinyl group, a tetrahydrofuranyl group, a lower alkoxypyridylamino group, and a pyrimidinylamino group, (iii) a phenyl group which is optionally substituted by hydroxy group or a lower alkoxy group, (iv) a pyridyl group which is optionally substituted by a lower alkyl group, (v) a pyrazolyl group which is optionally substituted by a lower alkyl group, (vi) an isoxazolyl group which is optionally substituted by a lower alkyl group, (vii) a morpholinyl group, (viii) a piperidyl group which is optionally substituted by one to four, same or different, substituents selected from the group consisting of a lower alkoxycarbonyl group, a lower alkylsulfonyl group, a lower alkyl group, a cyano-substituted lower alkyl group, a hydroxy-substituted lower alkanoyl group, formyl group, a lower alkoxy-substituted lower alkanoyl group, and a lower alkylamino-substituted lower alkanoyl group, (ix) a cyclo lower alkyl group which is optionally substituted by one to three, same or different, substituents selected from the group consisting of a hydroxy group which is optionally protected, a lower alkoxy group, and a pyrimidinyl-substituted oxy group, and (x) a pyrimidinylamino group which is optionally substituted by a lower alkyl group or a lower alkoxycarbonyl group, $R^4$, R, $R^6$ or $R^7$ is (1) a phenyl group which is optionally substituted by a lower alkoxy group, (2) a heterocyclic ring containing N atom(s) which is optionally substituted by hydroxy group, a lower alkyl group or a hydroxy-substituted lower alkyl group, (3) a lower alkoxy group, or (4) an amino group which is optionally substituted by a lower alkyl group substituted by a heterocyclic ring containing N atom(s), a hydroxy-substituted cyclo lower alkyl group, or a lower alkyl group, or $R^4$, $R^5$, $R^6$ or $R^7$ (5) optionally combines with $R^3$ to form a lactone ring as shown in following formula;

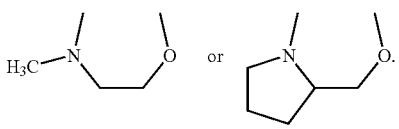

Preferable compounds (I) of the present invention are compounds (I) wherein

X is =N—,

Y is —S—, $R^1$ is a pyrrolidinyl group which is optionally substituted by a hydroxy-substituted lower alkyl, $R^2$ is a lower alkylamino group which is optionally substituted by a phenyl group which is optionally substituted by one or two, same or different, substituents selected from a lower alkoxy group and a halogen atom, and $R^3$ is an amino group which is optionally substituted by a lower alkoxy group or a pyrimidinyl-substituted lower alkyl group.

Preferable compounds (I) of the present invention are compounds (I) wherein

X is =N—,

Y is —N=N—, —CH=CH—,

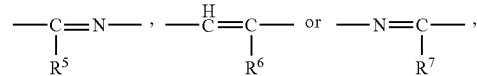

$R^1$ is (1) a lower alkoxy group which is optionally substituted by a lower alkylamino group or a pyridyl group, (2) an amino group which is optionally substituted by hydroxy group or a lower alkoxy group, (3) a heterocyclic ring containing N atom(s) which is optionally substituted by hydroxy group, a lower alkoxy group, a lower alkyl group, a hydroxy-substituted lower alkyl group, oxo group, a pyridyl group which is optionally substituted by a hydroxy-substituted lower alkyl group, or a pyrimidinyl group which is optionally substituted by a lower alkylamino group, or (4) a hydroxy group which is optionally substituted by a pyridyl group, $R^2$ is a lower alkylamino group which is optionally substituted by a phenyl group which is optionally substituted by a lower alkoxy group and/or a halogen atom, $R^3$ is (1) a lower alkoxy group which is optionally substituted by a phenyl-substituted lower alkoxy group, or (2) an amino group which is optionally substituted by (i) a lower alkyl group which is optionally substituted by the same or different subsituents selected from a group of consisting of a lower alkoxy group, a pyridyl group, a lower alkylpyridyl group, a pyrimidinyl group, a lower alkoxypyrimidinyl group, a morpholinyl group, and a lower alkylpyrazinyl group, (ii) a pyridyl group which is optionally substituted by a lower alkyl group, or (iii) a cyclo lower alkyl group which is optionally substituted by hydroxy group, $R^5$, $R^6$ or $R^7$ is (1) a phenyl group which is optionally substituted by a lower alkoxy group, (2) a heterocyclic ring containing N atom(s) which is optionally substituted by a hydroxy group, a lower alkyl group or a hydroxy-substituted lower alkyl group, (3) a lower alkoxy group, (4) an amino group which is optionally substituted by a lower alkyl group substituted by a heterocyclic ring containing N atom(s), a hydroxy-substituted cyclo lower alkyl group, or a lower alkyl group, or (5) optionally combines with $R^3$ to form a lactone ring as shown in following formula,

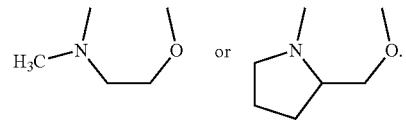

Preferable compounds (I) of the present invention are compounds (I) wherein

X is =N—,

Y is —CH=N— or —N=CH—, $R^1$ is (1) a lower alkoxy group which is optionally substituted by one to three, same or different, substituents selected from the group consisting of a cyclo lower alkyl group, hydroxy group, a lower alkylamino group which is optionally protected, a lower alkylamino group, a lower alkoxy group, a hydroxy-substituted lower alkyl group, phenyl group, a lower alkoxyphenyl group, a hydroxy-substituted lower alkylphenyl group, a furyl group, a pyridyl group, a lower alkoxypyridyl group, a hydroxy-substituted lower alkylpyridyl group, a lower alkylpyridyl group, a pyrimidinyl group, a lower alkoxypyrimidinyl group, and a morpholinyl group, (2) a lower alkylamino group which is optionally substituted by one to three, same or different, substituents selected from the group consisting of hydroxy group, a lower alkoxy group, a lower alkyl group, a pyridyl group, a lower alkylamino group, cyano group, a phenyl group which is optionally substituted by a lower alkoxy group and/or a halogen atom, and a hydroxy-substituted lower alkyl group, (3) an indanylamino group, (4) a heterocyclic ring containing N atom(s) which is optionally substituted by one to four, same or different, substituents selected from the group consisting of hydroxy group, a lower alkyl group, a lower alkoxy group, a hydroxy-substituted lower alkyl group, oxo group, a pyridyl group which is optionally substituted by a hydroxy-substituted lower alkyl group, a pyrimidinyl group which is optionally substituted by a lower alkylamino group, formyl group, mesyl group, a lower alkanoyl group substituted by a hydroxy group which is optionally protected, and carbamoyl group, (5) cyano group, or (6) a hydroxyl group which is optionally substituted by a pyridyl group, $R^2$ is (1) a lower alkylamino group substituted by an aryl group which is optionally substituted by one to four, same or different, substituents selected from the group consisting of a lower alkoxy group, a halogen atom, an amino group, a lower alkanoylamino group, a formylamino group, hydroxy group, a lower alkoxy pyridyl group, a lower alkylamino group, nitro group, a halogen-substituted lower alkyl group, a lower alkylenedioxy group, cyano group, a lower alkyl group substituted by a hydroxyl group which is optionally protected, a lower alkylsulfonyl group, and a lower alkylsulfinyl group, (2) a lower alkylamino group substituted by an indolyl group, a pyrimidinyl group, a benzofuranyl group, a dihydrobenzofuranyl group, a lower alkylpyrimidinyl group, a dihydrobenzoxazolyl group or a dihydrobenzimidazolyl group, or (3) an indanylamino group, (4) a lower alkoxy group substituted by an aryl group which is optionally substituted by one to four, same or different, substituents selected from a lower alkoxy group and a halogen atom, or (5) a lower alkoxy group substituted by a pyridyl group, $R^3$ is (1) an aryl group which is optionally substituted by one to four, same or different, substituents selected from the group consisting of a lower alkoxy group and a lower alkylamino group, or an aryl group which is optionally substituted by one or two lower alkylenedioxy group, (2) a heterocyclic ring containing N atom(s) which is optionally substituted by one to four, same or different, substituents selected from the group consisting of a lower alkyl group, hydroxy group, an amino group, chlorosulfinyloxy group and a piperidyloxysulfinyloxy group, (3) a lower alkyl group which is optionally substituted by one to three, same or different, substituents selected from the group consisting of a morpholinyl group and a di-lower alkoxyphosphoryl group, (4) a lower alkoxy group which is optionally substituted by one to three, same or different, substituents selected from the group consisting of a pyridyl group, a lower alkoxypyridyl group, a pyrimidinyl group, a lower alkylamino group, a pyrazinyl group, a lower alkoxy group which is optionally substituted by phenyl group, a pyrimidinyl-substituted oxy group, a pyridyl-substituted oxy group, a pyrimidinyl-substituted lower alkoxy group, a morpholinyl group, a lower alkylmorpholinyl group, a N-lower alkyl-N-pyrimidinylamino group, a lower alkyl dioxolanyl group, a lower alkoxy-substituted lower alkoxy group, a pyridylcarbonylamino group, hydroxy group, and a lower alkylpiperidyl group, (5) a cyclo lower alkoxy group which is optionally substituted by hydroxyl group, (6) a piperidyl-substituted hydroxy group which is optionally substituted by one to four, same or different, substituents selected from the group consisting of a pyrimidinyl group, a lower alkyl group and a cyano-substituted lower alkyl group, or (7) an amino group which is optionally substituted by one or two, same or different, substituents selected from the group consisting of (i) a lower alkoxy group which is optionally substituted by a lower alkoxy group, (ii) a lower alkyl group which is optionally substituted by one to three, same or different, substituents selected from the group consisting of cyano group, hydroxy group, a lower alkoxy group, a phenyl group which is optionally substituted by a lower alkoxy group and/or a halogen atom, carbamoyl group, a lower alkylamino group, a pyridyl group, a lower alkylpyridyl group, a lower alkoxypyridyl group, pyrimidinyl group, a lower alkoxypyrimidinyl group, a morpholinyl group, a lower alkyl morpholinyl group, a hydroxy-substituted lower alkyl morpholinyl group, a cyano-substituted lower alkyl morpholinyl group, a hydroxy-substituted piperidyl group, an oxo-substituted piperazinyl group, a lower alkyl piperazinyl group, a lower alkylsulfonylpiperazinyl group, a pyrrolidinyl group, a lower alkyl pyrrolidinyl group, a lower alkyl pyrazinyl group, a tetrahydrofuranyl group, a lower alkoxy pyridylamino group, and a pyrimidinylamino group, (iii) a phenyl group which is optionally substituted by hydroxy group or a lower alkoxy group, (iv) a pyridyl group which is optionally substituted by a lower alkyl group, (v) a pyrazolyl group which is optionally substituted by a lower alkyl group, (vi) an isoxazolyl group which is optionally substituted by a lower alkyl group, (vii) a morpholinyl group, (viii) a piperidyl group which is optionally substituted by one to four, same or different, substituents selected from the group consisting of a lower alkoxycarbonyl group, a lower alkylsulfonyl group, a lower alkyl group, a cyano-substituted lower alkyl group, a hydroxy-substituted lower alkanoyl group, formyl group, a lower alkoxy-substituted lower alkanoyl group, and a lower alkylamino-substituted lower alkanoyl group, (ix) a cyclo lower alkyl group which is optionally substituted by one to three, same or different, substituents selected from the group consisting of a hydroxy group which is optionally protected, a lower alkoxy group, and a pyrimidinyl-substituted oxy group, and (x) a pyrimidinylamino group which is optionally substituted by a lower alkyl group or a lower alkoxycarbonyl group.

Preferable compounds (I) of the present invention are compounds (I) wherein

X is =CH—,

Y is —CH—N—, —N=CH—, —N=N—,

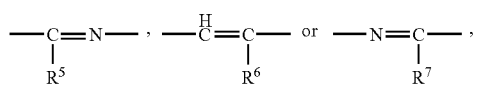

$R^1$ is a pyrrolidyl group which is optionally substituted by a hydroxy-substituted lower alkyl group, $R^2$ is a lower alkylamino group which is optionally substituted by a phenyl group which is optionally substituted by one or two substituents selected from a lower alkoxy group and a halogen atom, and $R^3$ is (1) a lower alkoxy group, (2) a lower alkyl group which is optionally substituted by a pyrimidinyl group or a morpholinyl group, or (3) an amino group which is optionally substituted by a cyclo lower alkyl group which is optionally substituted by hydroxy group.

Preferable compounds (I) of the present invention are compounds (I) wherein

X is =CH—,

Y is —CH=CH—, $R^1$ is a pyrrolidinyl group which is optionally substituted by a pyridyl-substituted lower alkoxy group or a hydroxy-substituted lower alkyl group, $R^2$ is a lower alkylamino group which is optionally substituted by an phenyl group which is optionally substituted by one or two substituents selected from a lower alkoxy group and a halogen atom, and $R^3$ is (1) a lower alkoxy group, or (2) a lower alkyl group which is optionally substituted by a pyrimidinyl group or a morpholinyl group.

Preferable compounds (I) of the present invention are compounds (I) wherein an aryl group on $R^1$, $R^2$, $R^3$, $R^4$, $R^5$, $R^6$ or $R^7$ is a monocyclic, bicyclic or tricyclic 6–14 membered aryl group which may be partially saturated, or a heterocyclic ring containing N atom(s) on $R^1$, $R^3$, $R^4$, $R^5$, $R^6$ or $R^7$ is a monocyclic or bicyclic 5 to 14 membered heterocyclic containing N atom(s). More concretely, said monocyclic, bicyclic or tricyclic 6–14 membered aryl group which may be partially saturated on $R^1$, $R^3$, $R^4$, $R^5$, $R^6$ or $R^7$ is phenyl, naphthyl, indenyl or indanyl.

More concretely said monocyclic or bicyclic 5 to 14 membered heterocyclic ring containing N atom(s) on $R^1$, $R^3$, $R^4$, $R^5$, $R^6$ or $R^7$ is shown as following structures:

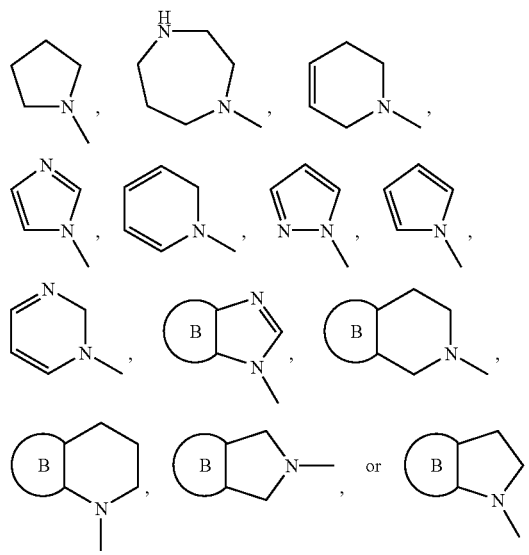

wherein ring B is shown as following structures;

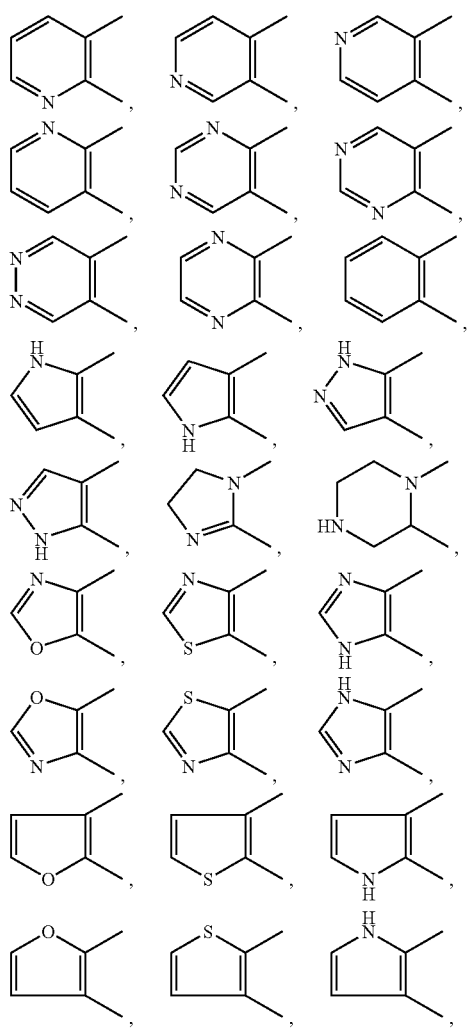

-continued

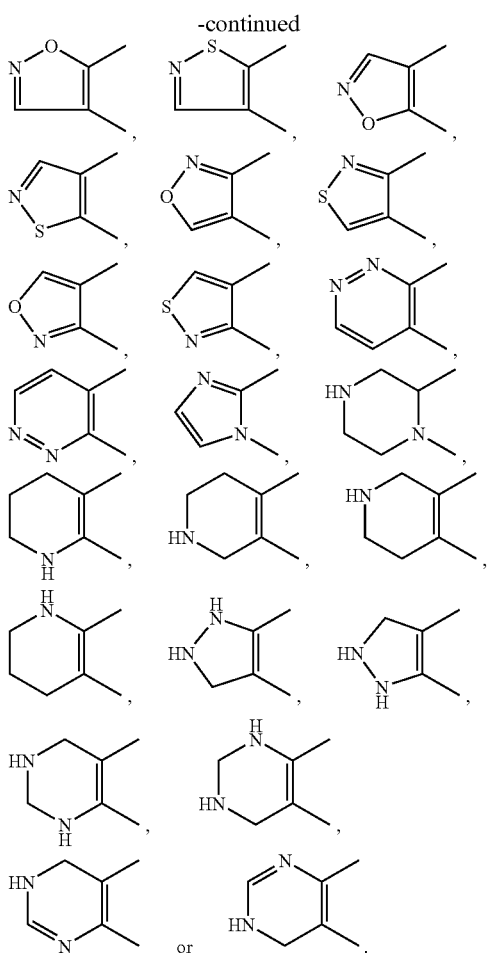

or

Furthermore concretely, said monocyclic or bicyclic 5 to 14 membered heterocyclic ring containing N atom(s) on $R^1$, $R^3$, $R^4$, $R^5$, $R^6$ or $R^7$ is pyridyl, pyrimidinyl, imidazolyl, piperidyl, pyrazolyl, morpholinyl, piperazinyl, pyrrolidinyl, dihydroisoindolyl, tetrahydroimidazo[1,2-a]pyrazyl, tetrahydroisoquinolyl, dihydro-5-pyrrolo[3,4-b]pyridyl, naphthylidinyl, pyrazo[3,4-d]pyridyl, tetrahydropyridyl, oxazolo[4,5-c]pyridyl, octahydropyrido[3,4-d]pyrimidinyl, thiazolo[4,5-d]pyridyl, imidazo[4,5-d]pyridyl, perhydrodiazepinyl, perhydropiperadino[3,4-c]piperadinyl, tetrahydroisoxazolo[4,5-c]pyridyl, hexahydropyrazolo[4,3-c]pyridyl, dihydropyridyl, tetrahydroxazolo[5,4-c]pyridyl, hexahydropyrido[3,4-d]pyrimidinyl, octahydropyrido[4,3-d]pyrimidinyl, tetrahydrothiazolo[5,4-c]pyridyl, imidazo[4,5-b]pyridyl, homopiperazinyl, perhydropyrazino[1,2-a]pyrazinyl, tetrahydropyrido[4,3-d]pyrimidinyl, tetrahydrothieno[3,2-c]pyridyl, or tetrahydronaphthylidinyl.

The compound (I) of the present invention or its pharmacologically acceptable salt can be present in form of optical isomers, in case that $R^1$, $R^2$, $R^3$, $R^4$, $R^5$, $R^6$ and/or $R^7$ have an asymmetric carbon atom, and the present invention includes these optical isomers and their mixture.

The compound (I) of the present invention or its pharmacologically acceptable salt has an excellent specific PDEV inhibitory activity, does affect little color sense disoder and blood pressure, and therefore, is useful for prophylactic or therapeutic agents for erectile dysfunction, etc.

The compound (I) of the present invention can be used as a medicine in free base or its acceptable salt. As a pharmacologically acceptable salt of the compound (I), are illustrated inorganic acid salts such as a hydrochloride, a sulfate, a nitrate, a hydrobromide, organic acid salts such as an acetate, a fumarate, an oxalate, a citrate, a methanesulfonate, a benzenesulfonate, a tosylate or a maleate.

The compound (I) of the present invention or its salt includes an intramolecular salt, an additive salt, its solvates or its hydrates.

The compound (I) of the present invention or its pharmacologically acceptable salt is manufactured into traditional pharmaceutical preparations. These preparations are prepared by a conventional method with additives, such as excipients, binders, poultices, disintegrants, or fillers.

The compound (I) of the present invention or its pharmacologically acceptable salt is, depending on administration route, age, body weight or situation of the patients, usually administerd about 0.001–100 mg/kg/day, especially 0.1–10 mg/kg/day.

According to the present invention, the compound (I) is prepared by [method A] to [Method D].

[Method A]

The compound (I) of the present invention is prepared by reacting a compound of the following formula(II),

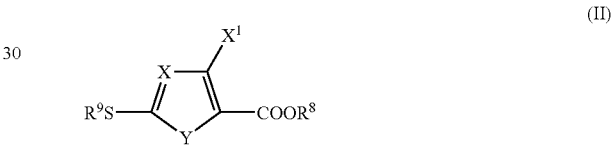

(II)

wherein $X^1$ is a halogen atom, $R^8$ is a protective group of the carboxyl group, $R^9$ is a lower alkyl group or an aryl group whose each group is optionally substituted, and X and Y are the same as defined above, with a compound of the following formula (III),

(III)

wherein $R^2$ is the same as defined above, to prepare a compound of the following formula (IV),

(IV)

wherein each symbol is the same as defined above, and by oxidizing the compound (IV) to prepare a compound of the following formula (V),

(V)

wherein n is 1 or 2, and other symbols are the same as defined above, and further, by reacting the compound (V) with a compound of the following formula (VI) or a salt thereof, $$R^1\text{—H} \tag{VI}$$

wherein $R^1$ is the same as defined above, to prepare a compound of the following formula (VII),

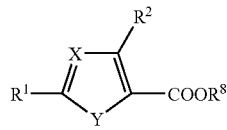
(VII)

wherein each symbol is the same as defined above, and then by removing a protective group of the carboxyl group, $R^8$ to prepare a compound of the following formula (VIII),

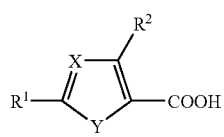
(VIII)

wherein each symbol is the same as defined above, and further by reacting the compound (VIII) with a compound of the following formula (IX) or its reactive derivative, $$R^3\text{—H} \tag{IX}$$

wherein $R^3$ is the same as defined above, to prepare the compound (I).

The compound (I) of the present invention is also prepared by halgenating the compound (VIII) to prepare a compound of the following formula (X),

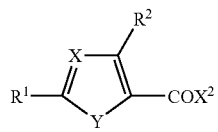
(X)

wherein $X^2$ is a halogen atom and other symbols are the same as defined, and then by reacting the compound (X) with a compound (IX) or its reactive derivative.

A compound (VII) wherein Y is —CH=N—, —N=CH— or —N=N—, is also prepared by reacting carbon dioxide and a dihalogeno compound of the following formula (XI),

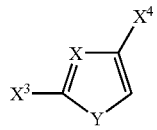
(XI)

wherein $X^3$ and $X^4$ are a halogen atom, and X is the same as defined above, and Y is —CH=N—, —N=CH— or —N=N—, to prepare a compound of the following formula (XII),

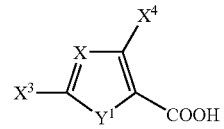
(XII)

wherein $Y^1$ is —CH=N—, —N=CH— or —N=N—, and other symbols are the same as defined, and by protecting the carboxyl group of the compound (XII) to prepare a compound of the following formula (XIII),

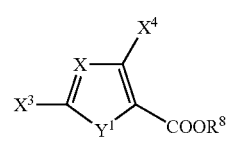
(XIII)

wherein the above symbols are the same as defined above, and then by reacting the compound (XIII) with a compound (III) to prepare a compound of the following formula (XIV),

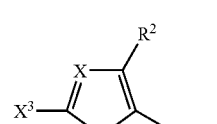
(XIV)

wherein the above symbols are the same as defined above, and then by reacting the compound (XIV) with the compound (VI).

A compound (XIV) is also prepared by hydrolyzing a compound (V) wherein Y is —CH=N—, —N=CH— or —N=N—, to prepare a compound of the following formula (XV),

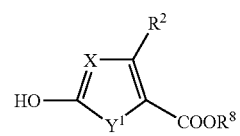
(XV)

wherein the above symbols are the same as defined above, and then by halogenating the compound (XV).

[Method B]

The compound (I) of the present invention is prepared by reducing a compound (IV) to prepare a compound of the following formula (XVI),

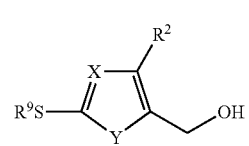
(XVI)

wherein the above symbols are the same as defined above, and then by oxidizing the compound (XVI) to prepare a compound the following formula (XVII),

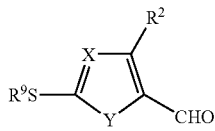
(XVII)

wherein the above symbols are the same as defined above, and then, by oxidizing the compound (XVII) to prepare a compound of the following formula (XVIII),

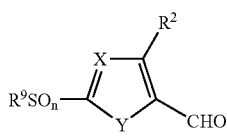
(XVIII)

wherein the above symbols are the same as defined above, and then by reacting the compound (XVIII) with a compound (VI) or its salt, to prepare a compound of the following formula (XIX),

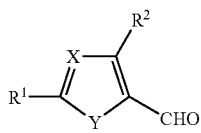
(XIX)

wherein the above symbols are the same as defined above, and further by reacting the compound (XIX) with a compound (IX) or its reactive derivative to prepare a compound of the following formula (XX),

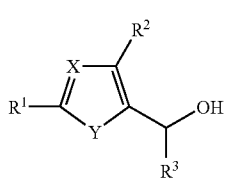
(XX)

wherein the above symbols are the same as defined above, and then by further oxidizing the compound (XX).

The compound (I) in which $R^3$ is a lower alkoxy-substituted ethyl group or a morpholino-substituted ethyl group, namely a compound of the following formula (I-a),

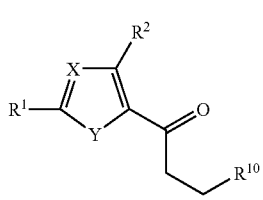
(I-a)

wherein $R^{10}$ is a lower alkoxy group or morpholino group, and other symbols are the same as defined above, is also prepared by reacting a compound (XIX) and a Grignard agent of the following formula (XXI),

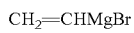
$CH_2$=CHMgBr  (XXI)

to prepare a compound of the following formula (XXII),

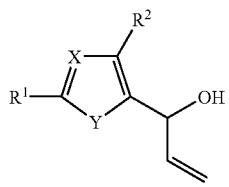
(XXII)

wherein the above symbols are the same as defined above, and by oxidizing the compound (XXII) to prepare a compound of the following formula (XXIII),

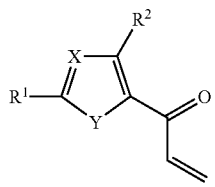
(XXIII)

wherein the above symbols are the same as defined above, and then by reacting the compound (XXIII) and a compound of the following formula (XXIV) or its salt,

$R^{10}$—H  (XXIV)

wherein $R^{10}$ is the same as defined above.

[Method C]

The compound (I) of the present invention is also prepared by reacting a compound of the following formula (XXV),

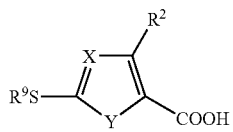
(XXV)

wherein the above symbols are the same as defined above, which is prepared by deprotecting the protective group ($R^8$) of the carboxyl group of a compound (IV), and a compound (IX) or its reactive group to prepare a compound of the following formula (XXVI),

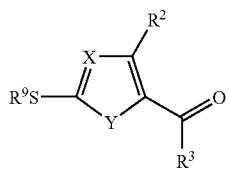
(XXVI)

wherein the above symbols are the same as defined above, and by oxidizing the compound (XXVI) to prepare a compound of the following formula (XXVII),

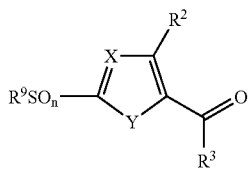
(XXVII)

wherein the above symbols are the same as defined above, and by reacting the compound (XXVII) with a compound (VI) or its salt.

The compound (XXVI) is also prepared by reacting a compound (XVII) and a compound (IX) or its reactive derivative to prepare a compound of the following formula (XXVIII),

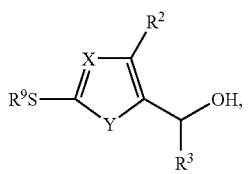
(XXVIII)

wherein the above symbols are the same as defined above, and then by oxidizing the compound (XXVIII).

[Method D]

The compound (I) is also prepared by reacting a dihalogeno compound (XI) and a compound of the following formula (XXIX), $R^3$—CHO     (XXIX)

wherein $R^3$ is the same as defined above, to prepare a compound of the following formula (XXX),

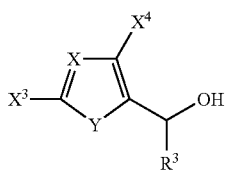
(XXX)

wherein the above symbols are the same as defined above, and by oxidizing the compound (XXX) to prepare a compound of the following formula (XXXI),

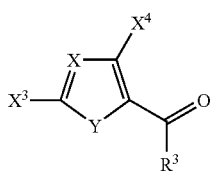
(XXXI)

wherein the above symbols are the same as defined above, and by reacting the compound (XXXI) with a compound (III) to prepare a compound of the following formula (XXXII),

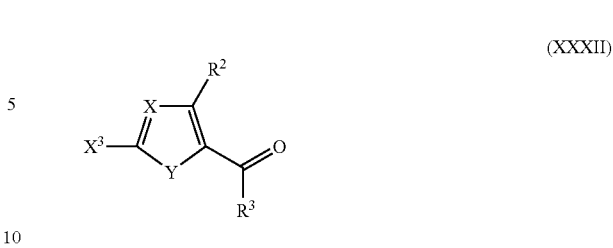
(XXXII)

wherein the above symbols are the same as defined above, and by reacting the compound (XXXII) with a compound (VI) or its salt.

The compound (XXXII) is also prepared by reacting a compound (XXX) and a compound (III) to prepare a compound of the following formula (XXXIII),

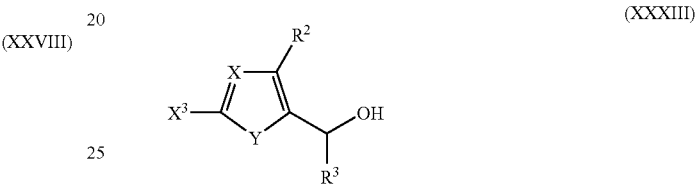
(XXXIII)

wherein the above symbols are the same as defined above, and then by oxidizing the compound (XXXIII).

[Method E]

Among the compounds (I) of the present invention, a compound of the following formula (I-b),

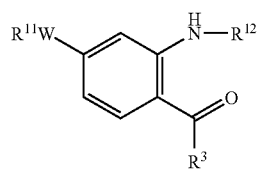
(I-b)

wherein W is immino group or an oxygen atom, $R^{11}$ is a lower alkyl group which is optionally substituted, $R^{12}$ is an aryl-substituted lower alkyl group which is optionally substituted or a lower alkyl group substituted by an aromatic heterocycle containing N atom(s), and $R^3$ is the same as defined above, is also prepared by reacting a compound of the following formula (XXXIV),

(XXXIV)

wherein $R^{13}$ is a protective group of hydroxy group or a protective group of an amino group, with ammonia to prepare a compound of the following formula (XXXV),

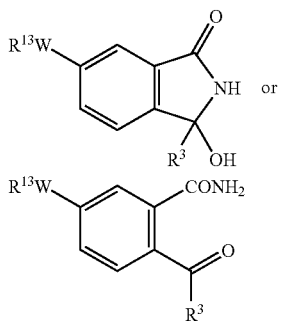
(XXXV)

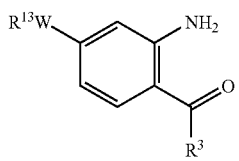

wherein the above symbols are the same as defined above, and by subjecting the compound (XXXV) to Hofmann rearrangement to prepare an aniline compound of the following formula (XXXVI),

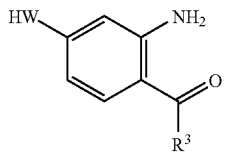
(XXXVI)

wherein the above symbols are the same as defined above, and by deprotecting the protective group $R^{13}$ to prepare a compound of the following formula (XXXVII),

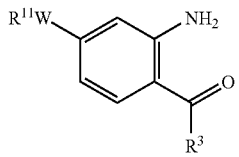
(XXXVII)

wherein the above symbols are the same as defined above, and by reacting the compound (XXXVII) with a compound of the following formula (XXXVIII), $R^{11}-X^5$  (XXXVIII)

wherein $X^5$ is a leaving group and $R^{11}$ is the same as defined above, to prepare a compound of the following formula (XXXIX), (XXXIX)

wherein the above symbols are the same as defined above, and further, by reacting the compound (XXXIX) with a compound of the following formula (XL), $R^{12}-X^6$  (XL)

wherein $X^6$ is a leaving group and $R^{12}$ is the same as defined above.

The compound (I-b) of the present invention is also prepared by reacting a compound (XXXVI) with a compound (XL) to prepare a compound of the following formula (XLI),

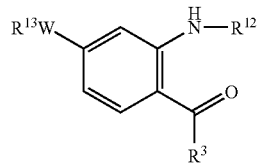
(XLI)

wherein the above symbols are the same as defined above, and by deprotecting the protective group $R^{13}$ of the compound (XLI) to prepare a compound of the following formula (XLII),

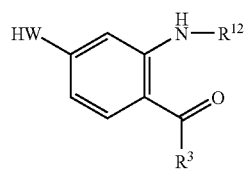
(XLII)

wherein the above symbols are the same as defined above, and by reacting the compound (XLII) with a compound (XXXVIII).

[Process F]

Among compounds (I) of the present invention, a compound of the following formula (I-c)

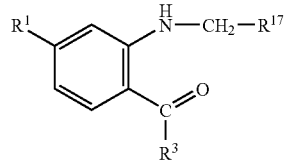
(I-c)

wherein $R^{17}$ is an aryl group which is optionally substituted and other symbols are the same as defined above, is also prepared by reacting a compound of the following formula (XLIII),

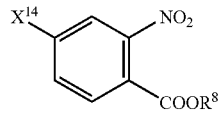
(XLIII)

wherein $X^{14}$ is a halogen atom and $R^8$ is the same as defined above, with a compound (VI) to prepare a compound of the following formula (XLIV),

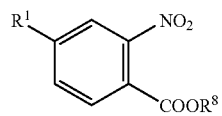
(XLIV)

wherein the above symbols are the same as defined above, and by reducing the compound (XLIV) to prepare a compound of the following formula (XLV),

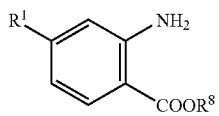
(XLV)

wherein the above symbols are the same as defined above, and by reacting the compound (XLV) with a compound of the following formula (XLVI), $$R^{17}-CHO \quad (XLVI)$$

wherein the above symbols are the same as defined above, to prepare a compound of the following formula (XLVII),

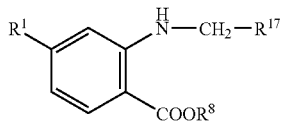
(XLVII)

wherein the above symbols are the same as defined above, and by deprotecting the protective group ($R^8$) of the compound (XLVII), and then by reacting the deprotected compound with a compound (IX) or its reactive derivative.

Furthermore, according to the present invention, a compound (I) wherein Y is

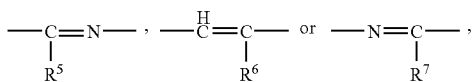

(in which the above symbols are the same as defined above), namely a compound of the following formula (I-d),

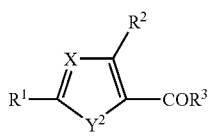
(I-d)

wherein $Y^2$ is

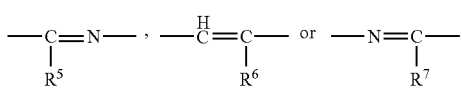

(in which the above symbols are the same as defined above), is prepared by the following methods G to I.

[Method G]

A compound (I-d) of the present invention is prepared by treating a compound of the following formula (XLVIII),

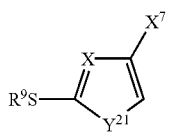
(XLVIII)

wherein $Y^{21}$ is

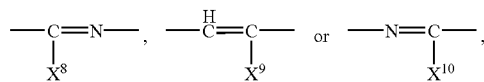

(in which $X^7$, $X^8$, $X^9$ and $X^{10}$ are a halogen atom), and other symbols are the same as define above, with carbon dioxide to prepare a compound of the following formula (XLIX),

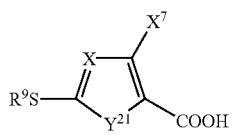
(XLIX)

wherein the above symbols are the same as defined above, and by reacting the compound (XLIX) with a compound (III) to prepare a compound of the following formula (L),

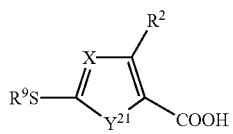
(L)

wherein the above symbols are the same as defined above, and if necessary, hogenating the compound (L) and then by reacting the compound (L) with a compound (IX) or its reactive derivative to prepare a compound of the following formula (LI),

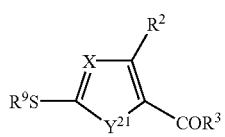
(LI)

wherein the above symbols are the same as defined above, and by reacting the compound (LI) with a compound of the following formula (LII), $$H-R^{5-7} \quad (LII)$$

wherein $R^{5-7}$ is $R^5$, $R^6$ or $R^7$, to prepare a compound of the following formula (LIII),

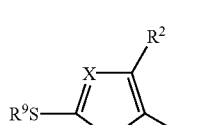
(LIII)

wherein the above symbols are the same as defined above, and by oxidizing the compound (LIII), and then by reacting the oxidized compound with a compound (VI).

$R^3$ of a compound (LIII) of the present invention may be converted, if necessary after protecting the carboxyl group of a compound (L). As said protective group, one used in a liquid phase and a usual solid phase carrier such as a merrifield resin may be used. The addition-reaction of the compound (LII) is carried, if desired.

[Method H]

A compound (I-d) of the present invention is prepared by reacting a compound of the following formula (LIV),

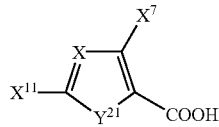
(LIV)

wherein $X^{11}$ is a halogen atom and other symbols are the same as defined above, and a compound (III), and then by reacting the reactant with a compound (IX) or its reactive derivative to prepare a compound of the following formula (LV),

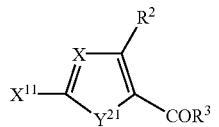
(LV)

wherein the above symbols are the same as defined above, and by reacting the compound (LV) with a compound of the following formula (LVI), $R^9SH$ (LVI)

wherein $R^9$ is the same as defined above, to prepare a compound of the following formula (LVII),

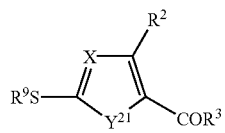
(LVII)

wherein the above symbols are the same as defined above, and by reacting the compound (LVII) with a compound (LII) to prepare a compound (LIII) and by oxidizing the compound (LIII), and then by reacting the oxidized compound with a compound (VI).

The compound (I-d) is also prepared, after reacting a compound (LV) with a compound (LII), by reacting the reactant with a compound (VI), or by reacting the reactant with a compound (LII) after reacting a compound (LV) and a compound (VI).

[Method I]

A compound (I-d) of the present invention is prepared by treating a compound of the following formula (LVIII),

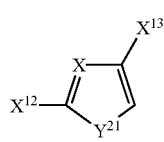
(LVIII)

wherein $X^{12}$ and $X^{13}$ are a halogen atom, and other symbols are the same as defined above, with carbon dioxide to prepare a compound of the following formula (LIX),

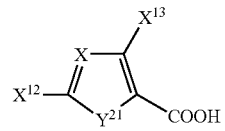
(LIX)

wherein the above symbols are the same as defined above, and by reacting the compound (LIX) with a compound (LVI), and then by reacting the reactant with a compound (IX) or its reactive derivative to prepare a compound of the following formula (LX),

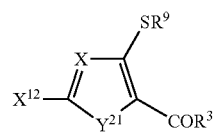
(LX)

wherein the above symbols are the same as defined above, and by reacting the compound (LX) with a compound (LII) to prepare a compound of the following formula (LXI),

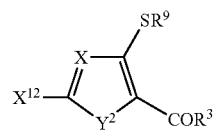
(LXI)

wherein the above symbols are the same as defined above, and by reacting the compound (LXI) with a compound (VI) or its salt and by oxidizing the reactant and then by reacting the oxidized compound with a compound (III).

According to the present invention, the compound (I) wherein Y is —NH—, —NR$^4$—, —S— or —O—, and $R^2$ is a lower alkylamino group which is optionally substituted by an aryl group which is optionally substituted, namely a compound of the following formula (I-e),

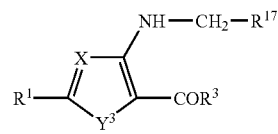
(I-e)

wherein $Y^3$ is —NH—, —NR$^4$—, —S— or —O—, and $R^{17}$ is an aryl group which is optionally substituted, and other symbols are the same as defined above, is prepared by the following Method J

[Method J]

A compound (I-e) of the present invention is prepared by protecting a compound of the following formula (LXII)

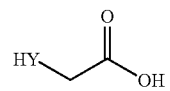
(LXII)

wherein the above symbols are the same as defined above, to prepare a compound of the formula (LXIII),

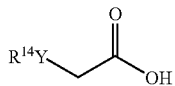
(LXIII)

wherein $R^{14}$ is a protective group, and Y is the same as defined above, and then, by reacting the compound (LXIII) with a compound (IX) or its reactive derivative to prepare a compound of the following formula (LXIV)

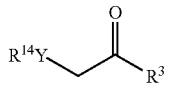
(LXIV)

wherein the above symbols are the same as defined above, and then by deprotecting the compound (LXIV) to prepare a compound of the following formula (LXV),

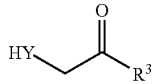
(LXV)

wherein the above symbols are the same as defined above, and then, by reacting the compound (LXV) with a compound of the following formula (LXVI),

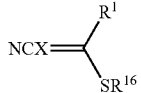
(LXVI)

wherein $R^{16}$ is a lower alkyl group which is optionally substituted or an aryl group which is optionally substituted, and other symbols are the same as defined above, to prepare a compound of the following formula (LXVII),

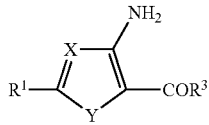
(LXVII)

wherein the above symbols are the same as defined above, and by reacting the compound (LXVII) with a compound (XLVI).

Furthermore, according to the present invention, the compound (I) is also prepared by appropriately combining each step in the above methods, and $R^1$ of the compound (I) is changed, if desired.

The above methods A–J are practiced as follows:

[Method A]

The reaction of a compound (II) and a compound (III) is carried out in a solvent in the presence or absence of an acid scavenger.

As an acid scavenger, is preferably used such as an organic base, such as N,N-diisopropylethylamine, N-methylmorpholine, triethylamine or pyridine, etc., or an inorganic base, such as sodium hydride, sodium carbonate, potassium carbonate or sodium hydrogen carbonate, etc. As a solvent, is preferably used a solvent which does not disturb the reaction, such as dimethyl sulfoxide, tetrahydrofuran, toluene, ethylacetate, chloroform, dimethoxyethane, xylene, N,N-dimethylformamide, acetonitrile, N-methylpyrrolidone, N,N-dimethylacetamide, or dioxane, etc. The reaction of a compound (II) and a compound (III) which are poor in reactivity is preferably carried out in catalyst of a copper reagent such as copper bromide, etc. The reaction preferably proceeds at −10° C. to room temperature, especially at 0° C. to room temperature.

The oxidation reaction of the compound (IV) to give the compound (V) can be carried out in the presence of an oxidizing agent in a solvent. As an oxidizing agent, is preferably used a peracid, such as m-chloro perbenzoic acid, or peracetic acid, or an inorganic oxidizing agent such as manganese dioxide, sodium periodide, hydrogen peroxide, dinitrogen tetroxide, halogen, hydroperoxide, iodobenzene acetate, tert-butyl hypochlorite, surfuryl chloride, or potassium peroxymonosulfate, etc. As a solvent, is preferably used a solvent which does not disturb the reaction, such as chloroform, methylene chloride, dichloroethane, or acetic acid, etc. The reaction is preferably carried out at −78° C. to 50° C., especially −10° C. to 10° C.

The reaction of a compound (V) and a compound (VI) or its salt is carried out in a solvent in the presence or absence of an acid scavenger. As an acid scavenger, is preferably used such as an organic base such as N,N-diisopropylethylamine, N-methylmorpholine, triethylamine, or pyridine, etc., or an inorganic base, such as sodium hydride, sodium carbonate, potassium carbonate, cesium carbonate or sodium hydrogen carbonate, etc. As a salt of a compound (VI), is preferably used an alkali metal salt, such as a sodium salt, or potassium salt, etc. As a solvent, is preferably used a solvent which does not disturb the reaction, such as N,N-dimethylformamide, tetrahydrofuran, dimethoxyethane, dimethyl sulfoxide, acetonitrile, N-methylpyrrolidone, N,N-dimethylacetamide, dioxane, diglyme or dimethoxyethane, etc. The reaction of a compound (V) and a compound (VI) which are poor in reactivity is preferably carried out by addition of palladium(0) catalyst and phosphine ligand. Trisdibenzylidene acetone dipalladium is preferably used as catalyst and 2,2'-bisdiphenylphosphino-1,1'-binaphtyl, etc., as phosphine ligand, respectively. The reaction preferably proceeds at 0° C. to 250° C., especially at room temperature to 200° C.

In order to prepare a compound (VIII) from a compound (VII) by deprotecting the protective group (Re) of the carboxyl group thereof, the conventional method depending on a kind of the protective groups (e.g. hydrolysis, catalytic reduction, etc.) is properly utilized. In case of deprotection of the protective group by hydrolysis, for example the hydrolysis is carried out in a solvent in the presence of a base. As a base, is preferably used such as an alkali metal hydroxide, such as sodium hydroxide, potassium hydroxide, or lithium hydroxide, etc., or an alkali metal carbonate, such as sodium carbonate, or potassium carbonate, etc. As a solvent, water or a mixture of water and methanol, ethanol, tetrahydrofuran, dioxane, N,N-dimethylformamide, or dimethyl sulfoxide, etc., is properly used. The reaction is preferably carried out at 0° C. to 80° C., especially 5° C. to 60° C. As a protective group ($R^8$) of the carboxyl group, is used a conventional protective group, such as a lower alkyl group or benzyl group, etc.

The reaction of a compound (VIII) and a compound (IX) or its reactive derivative is carried out in a solvent in the presence or absence of a condensing agent, a base or an activating agent. As a reactive derivative of a compound (IX), is preferably used a halogenated compound or a salt of the compound (IX). As a condensing agent, is preferably used dicyclohexylcarbodiimido, 1-ethyl-3-(3-dimethylaminopropyl)carbodiimido, diphenylphospholylazido, or diethylcyanophosphonate, etc., which is usually used in the peptide synthesis. As a base, is preferably used an organic base, such as triethylamine or N-methylmorpholine, etc., and as an activating agent, is preferably used 1-hydroxybenzotriazole, etc. As a solvent, is preferablly used a solvents which does not disturb the reaction, such as methylene chloride, tetrahydrofuran, N,N-dimethylformamide, acetonitrile, N,N-dimethylacetamide, ethyl acetate, etc. The reaction is carried out at $-30°$ C. to $50°$ C., especially $-10°$ C. to $10°$ C.

The reaction of a compound (IX) or its reactive derivative with a compound (X), which is prepared from a compound (VIII) as another method, is carried out as follows: first a compound (VIII) is reacted with a hologenating agent in the presence or absence of an activating agent by a conventional method to prepare the compound (X), and then the compound (X) is reacted with the compound (IX). The reaction of the compound (VIII) and a halogenating agent is carried out in a solvent or without a solvent. As a halogenating agent, is preferably used thionyl chloride, oxalyl chloride or phosphorus pentachloride, etc. As an activating agent, is preferably used an amide compound such as N,N-dimethylformamide, or diethylaniline, etc. As a solvent is preferably used a solvent which does not disturb the reaction, such as methylene chloride, chloroform, tetrahydrofuran, benzene, toluene, or dioxane, etc. The reaction is preferably carried out at $-30°$ C. to $100°$ C., especially $5°$ C. to $10°$ C.

The subsequent reaction of a compound (X) and a compound (IX) is carried out in a solvent in the presence of an acid scavenger. As an acid scavenger, is preferably used an organic base, such as N,N-diisopropylethylamine, N-methylmorpholine, triethylamine, pyridine, dimethylaminopyridine, etc., or an inorganic base, such as sodium hydroxide, sodium carbonate, potassium carbonate, sodium hydrogen carbonate, etc. As a solvent is preferably used a solvent which does not disturb the reaction, such as tetrahydrofuran, methylene chloride, chloroform, N,N-dimethylacetamide, toluene, benzene, dioxane, or ethyl acetate, etc. The reaction is preferably carried out at $-30°$ C. to $100°$ C., especially $5°$ C. to $10°$ C.

Further, the reaction to prepare a compound (XII) from a dihalogeno compound (XI) by treating it with carbon dioxide is carried out in a solvent with a base. As a base, is preferably used such as an alkali metal salt of an organic base, such as lithium diisopropylamide, or lithium 2,2,6,6-tetramethylpiperizide, etc. As a solvent, is preferably used a solvent which does not disturb the reaction, such as tetrahydrofuran, 1,2-dimethoxyethane, or diethyl ether, etc. The reaction is preferably carried out at $-100°$ C. to $-30°$ C., especially $-100°$ C. to $-70°$ C.

The reaction to prepare a compound (XIII) by protecting the carboxyl group of a compound (XII) is carried out by a conventional method. In case that the protective group is a lower alkyl group, the reaction is carried out in the presence of a base and a solvent by adding an alkylating agent to the compound (XII). As an alkylating agent, is preferably used a lower alkyl halide such as methyl iodide. As a base, is preferably used an alkali metal hydrogen carbonate such as sodium hydrogen carbonate, and as a solvent, is preferably used a solvent which does not disturb the reaction, such as N,N-dimethylformamide or tetrahydrofuran, etc. The reaction is preferably carried out at $0°$ C. to $100°$ C., especially room temperature to $70°$ C.

The reaction to prepare a compound (XIV) by reacting a compound (XIII) and a compound (III) is carried out in the same manner as the reaction of the compound (II) and the compound (III).

The reaction to prepare a compound (VII) by reacting a compound (XIV) and a compound (VI) is carried out in the same manner as the reaction of the compound (V) and the compound (VI).

The reaction to prepare a compound (XV) from a compound (V) by hydrolyzing it is carried out in a solvent in the presence of a base. As a base, is preferably used such as an alkali metal hydroxide, such as sodium hydroxide, potassium hydroxide, or lithium hydroxide, etc., or an alkali metal carbonate, such as sodium carbonate, or potassium carbonate, etc. As a solvent, is properly used water or a mixture of water and methanol, ethanol, tetrahydrofuran, dioxane, N,N-dimethylformamide, dimethyl sulfoxide, etc. The reaction is preferably carried out at $-20°$ C. to $80°$ C., especially $5°$ C. to $60°$ C.

The reaction to prepare a compound (XIV) by halogenating a compound (XV) is carried out in the same manner as the reaction to prepare the compound (X) by halogenating the compound (VIII) with a halogenating agent.

[Method B]

The reduction of the a compound (IV) to give the compound (XVI) can be carried out in the presence of a reducing agent in a suitable solvent. As a reducing agent, is preferably used such as an alkali metal alminium hydrate, such as lithium alminium hydrate, or an alkali metal borohydrate, such as lithium borohydrate. As a solvent, is preferably used such as a solvent which does not disturb the reaction, such as tetrahydrofuran, dioxane, diethyl ether, or dimethoxyethane, etc. The reaction is preferably carried out at $-78°$ C. to a boiling point of the solvent, especially $-10°$ C. to room temperature.

The oxidation of the compound (XVI) to give the compound (XVII) can be carried out in the presence of an oxidation agent in a solvent. There is no limitation as long as the oxidizing agent leads an alcohol compound into a carbonyl compound, but is preferably used manganese dioxide, barium per manganate, potassium permanganate, 2,3-dichloro-5,6-dicyano-1,4-benzoquinone, pyridinium chlorochromate, or pyridinium dichromate, etc. As a solvent, is preferably used a solvent which does not disturb the reaction, such as chloroform, toluene, ethyl acetate, 1,2-dichloroethane, methylene chloride, or tetrahydrofuran, etc. The reaction is preferably carried out at $0°$ C. to $100°$ C., especially room temperature to $70°$ C.

The reaction to prepare a compound (XVIII) by oxidizing a compound (XVII) is carried out in the same manner as the reaction to prepare the compound (V) by oxidizing the compound (IV).

The reaction to prepare a compound (XIX) by reacting a compound (XVIII) and a compound (VI) is carried out in the same manner as the reaction of the compound (V) with a compound (VI).

The reaction to prepare a compound (XX) by reacting a compound (XIX) and a compound (IX) or its reactive derivative is carried out in an appropriate solvent. As a solvent, is preferably used a solvent which does not disturb the reaction, such as tetrahydrofuran, dioxane, diethyl ether, or dimethoxyethane, etc. The reaction is preferably carried out at $-78°$ C. to room temperature.

The reaction to prepare the compound (I) by oxidizing a compound (XX) is carried out in the same manner as the reaction to prepare the compound (XVII) by oxidizing the compound (XVI).

Further, the reaction of a compound (XIX) and a Grignard reagent (XXI) is carried out in an appropriate solvent. As a solvent, is preferably used a solvent which does not disturb the reaction, such as tetrahydrofuran, dioxane, or diethyl ether, etc. The reaction is preferably carried out at −78° C. to 60° C., especially −78° C. to room temperature.

The reaction to prepare a compound (XXIII) by oxidizing a compound (XXII) is carried out in the same manner as the reaction to prepare the compound (XVII) by oxidizing the compound (XVI).

The reaction to prepare a compound (I-a) in which $R^{10}$ is morpholino by reacting a compound (XXIII) with a compound (XXIV) in which $R^{10}$ is morpholino group, is carried out in an appropriate solvent in the presence or absence of a base. As a base, is preferably used such as an organic base, such as N,N-diisopropylethylamine, N-methylmorpholine, triethylamine, pyridine, etc., or an inorganic base, such as sodium hydride, sodium carbonate, potassium carbonate, or sodium hydrogen carbonate, etc. As a solvent, is preferably used ethanol, N,N-dimethylformamide, tetrahydrofuran, dimethoxyethane, dimethyl sulfoxide, etc. The reaction is preferably carried out at 0° C. to 150° C., especially room temperature to 60° C.

On the other hand, the reaction to prepare a compound (I-a) in which $R^{10}$ is a lower alkoxy group by reacting a compound (XXIII) with a compound (XXIV) in which $R^{10}$ is a lower alkoxy group, is carried out in the presence of an acid in a solvent or without a solvent. As an acid, is preferably used an inorganic acid such as sulfuric acid, or an organic acid, such as methane sulfonic acid, camphor sulfonic acid, toluene sulfonic acid or benzene sulfonic acid, etc. As a solvent, is preferably used diethyl ether, toluene, benzene, N,N-dimethylformamide, dimethoxyethane, or dimethyl sulfoxide, etc. The reaction is preferably carried out at 0° C. to 150° C., especially room temperature to 60° C.

[Method C]

The reaction of removing the protective group ($R^8$) of the carboxyl group of a compound (IV) to give the compound (XXV) is carried out in the same manner as in the reaction of obtaining the compound (VIII) by removinig the protective group ($R^8$) from the carboxyl group of the compound (VII).

The reaction to prepare a compound (XXVI) by reacting a compound (XXV) with a compound (IX) or its reactive derivative is carried out in the same manner as the reaction of the compound (VIII) with the compound (IX) or its reactive derivative.

The reaction to prepare a compound (XXVII) by oxidizing a compound (XXVI) is carried out in the same manner as the reaction to prepare the compound (V) by oxidizing the compound (IV).

The reaction to prepare the compound (I) of the present invention by reacting a compound (XXVII) with a compound (VI) is carried out in the same manner as the reaction of the compound (V) with the compound (VI).

The reaction to prepare a compound (XXVIII) by reacting a compound (XVII) with a compound (IX) or its reactive derivative is carried out in the same manner as the reaction of the compound (XIX) with the compound (IX) or its reactive derivative.

The reaction to prepare a compound (XXVI) by oxidizing a compound (XXVIII) is carried out in the same manner as the reaction to prepare the compound (XVII) by oxidizing the compound (XVI).

[Method D]

The reaction to prepare a compound (XXX) by reacting a compound (XI) with a compound (XXIX) is carried out in an appropriate solvent in the presence of a base. As a base, is preferably used such as an alkali metal salt of an organic base, such as lithium diisopropylamide, or lithium 2,2,6,6-tetramethylpiperizide, etc. As a solvent, is preferably used a solvent which does not disturb the reaction, such as tetrahydrofuran, 1,2-dimethoxyethane, or diethyl ether. The reaction is preferably carried out at −100° C. to −30° C., especially −100° C. to −70° C.

The reaction to prepare a compound (XXXI) by oxidizing a compound (XXX) is carried out in the same manner as the reaction to prepare the compound (XVII) by oxidizing the compound (XVI).

The reaction to prepare a compound (XXXII) by reacting a compound (XXXI) with a compound (III) is carried out in the same manner as the reaction of the compound (II) with the compound (III).

Further, the reaction to prepare the compound (I) of the present invention by reacting a compound (XXXII) with a compound (VI) or its salt is carried out in the same manner as the reaction of the compound (V) with the compound (VI).

The reaction to prepare a compound (XXXIII) by reacting a compound (XXX) with a compound (III) is carried out in the same manner as the reaction of the compound (II) with the compound (III). The reaction to prepare a compound (XXXII) by oxidizing a compound (XXXIII) is carried out in the same manner as the reaction to prepare the compound (XVII) by oxidizing the compound (XVI).

[Method E]

The reaction to prepare a compound (XXXV) by reacting a compound (XXXIV) with ammonia is carried out in a presence of a condensing agent in a solvent. Ammonia can be used in an aqueous solution. As a condensing agent, is preferably used a condensing agent used in a conventional peptide synthesis, such as dicyclohexylcarbodiimide, 1-ethyl-3-(3-dimethylaminopropyl)carbodiimide, or diisopropylcarbodiimide, etc. As a solvent, is preferably used a solvent which does not disturb the reaction, such as N,N-dimethylformamide, methylene chloride, chloroform, tetrahydrofuran, etc. The reaction is carried out at −30° C. to 50° C., especially 0° C. to room temperature.

The reaction to lead a compound (XXXV) into a compound (XXXVI) by subjecting it to Hofmann reaction is carried out in the presence of a base in a solvent with an alkali metal hypohalogenite. As a base, is preferably used sodium hydroxide or potassium hydroxide, etc., and as a solvent, is preferably used a solvent which does not disturb the reaction, such as dioxane, tetrahydrofuran, methylene chloride, acetonitrile, tert-butanol, methanol, ethanol, etc. As an alkali metal hypohalogenite, is preferably used sodium hypochlorite, sodium hypobromite, potassium hypobromite, potassium hypochlorite. The reaction is carried out at −20° C. to 100° C., especially 10° C. to 60° C.

The reaction to prepare a compound (XXXVII) by deprotecting a compound (XXXVI), or to prepare a compound (XLII) by deprotecting a compound (XLI) is carried out according to the conventional deprotecting method used in the protective group for an amino group or a hydroxyl group. As a protective group for an amino group or a hydroxyl group, is illustrated formyl group, an alkanoyl group (acetyl group, propionyl group, chloroacetyl group, etc.), an aroyl group (benzoyl group, 4-methoxybenzoyl group, etc.), an alkoxycarbonyl group (methoxycarbonyl group, tert-butoxycarbonyl group, etc.), trialkylsilyl group (trimethylsilyl group, tert-butyldimethylsilyl group, etc.), an arylalkoxycarbonyl group (benzyloxycarbonyl group, etc,), an arylalkyl group (benzyl group, 4-methoxybenzyl group, etc.), or tetrahydropyranyl group.

The removal of the protective group of an amino group or a hydroxyl group is carried out by hydrolysis with an acid (e.g. hydrochloric acid, sulfuric acid, phosphoric acid, p-toluensulfonic acid, trifluoroacetic acid, acetic acid, hydrogen fluoride, hydrogen bromide, aluminum chloride, trimethylsilyliodide, trifluoroborate, etc.) or a base (e.g. sodium hydroxide, potassium hydroxide, potassium carbonate, sodium carbonate, potassium hydrogen carbonate, sodium hydrogen carbonate, ammonia, hydrazine, etc.), by reduction (hydrogen-palladium C, formic acid-palladium C, zinc-acetic acid, metallic sodium-liquid ammonia, etc.), or by oxidation (2,3-dichloro-5,6-dicyano-1,4-benzoquinone (DDQ), hydrogen peroxide, mercury acetate, etc.).

The reaction of a compound (XXXVII) with a compound (XXXVIII) is carried out in the presence of an acid scavenger in a solvent. As an acid scavenger, is preferably used an inorganic base, such as sodium hydroxide, potassium tert-butoxide, potassium carbonate, sodium carbonate, cesium carbonate, potassium hydroxide, sodium hydroxide, sodium methoxide, sodium ethoxide, potassium amide, a lithium amide (e.g. lithium diisoprpylamide), etc., an organic base such as N,N-diisopropylethylamine, N-methylmorpholine, triethylamine, pyridine, etc. As a solvent, is preferably used a solvent which does not disturb the reaction, such as tetrahydrofuran, ethanol, methanol, dimethoxyethane, dimethylformamide, toluene, xylene, dimethyl suifoxide, dimethylacetamide, dioxane, etc. The reaction preferably proceeds at −50° C. to boiling point of the solvent, especially at 0° C. to 100° C.

The reaction to prepare a compound (I-b) by reacting a compound (XXXIX) with a compound (XL), the reaction to prepare a compound (XLI) by reacting a compound (XXXVI) with a compound (XL), or the reaction to prepare a compound (I-b) by reacting a compound (XLII) with a compound (XXXVIII) is carried out in the same manner as the reaction of the compound (XXXVII) with the compound (XXXVIII).

[Method F]

The reaction of a compound (XLIII) with a compound (VI) is carried out in the same manner as the reaction of the compound (V) with the compound (VI).

The reduction of a compound (XLIV) is carried out by the conventional method, for example, preferably by catalytic reduction. The catalytic reduction is carried out for example, at atomospheric pressure under hydrogen gas in a solvent in the presence of catalyst. As catalyst is preferably used palladium-carbon. As a solvent is preferably used ethanol. The reaction proceeds preferably at room temperature.

The reaction of a compound (XLVI) with a compound (XLVI) is carried out in the presence of a reducing agent in a solvent in the presence or absence of an acid, etc. As a reducing agent, is preferably used a sodium triacyloxyborohydride, such as sodium triacetoxyborohydride. As an acid, is an organic acid, such as acetic acid, propionic acid, etc. As a solvent, is preferably used a solvent which does not disturb the reaction, such as dichloro ethane, methylene chloride, tetrahydrofuran, etc. The reaction preferably proceeds at −50° C. to 100° C., especially at −10° C. to room temperature.

The removal of the protective group ($R^8$) of the carboxyl group of a compound (XLVII) is carried out in the same manner as the removal of the protective group ($R^8$) of the carboxyl group of a compound (VII).

The subsequent reaction of the deprotected compound and a compound (IX) or its reactive derivative is carried out in the same manner as the reaction of a compound(VIII) and a compound (IX) or its reactive derivative.

[Method G]

The reaction to prepare a compound (XLIX) by treating a compound (XLVIII) with carbon dioxide is the same manner as the reaction to prepare a compound (XII) by treating a compound (XI) with carbon dioxide.

The reaction to prepare a compound (L) by reacting a compound (XLIX) with a compound (III) is carried out in the same manner as the reaction to prepare a compound (IV) by reacting the compound (II) with the compound (III).

The reaction to prepare a compound (LI) by reacting a compound (L) with a compound (IX), its salt or its reactive derivative is carried out in the same manner as the reaction to prepare a compound (I-a) by reacting the compound (VIII) with the compound (IX) or its reactive derivative. The halogenation of the compound (L) is carried out by the conventional method.

The reaction to prepare a compound (LIII) by reacting a compound (LI) with a compound (LII) is carried out in the same manner as the reaction to prepare the compound (IV) by reacting the compound (II) with the compound (III).

The reaction to prepare a compound (I) by reacting a compound (VI) or its salt after oxidation of a compound (LIII) is carried out in the same manner as the reaction to prepare a compound (I) by reacting the compound (VI) or its salt and the compound (V) prepared by oxidation of the compound (IV).

The protection of the carboxyl group of a compound (L) is carried out in the same manner as the reaction to prepare the compound (XIII) by protecting the carboxy group of the compound (XII). As a solid support, is used a halogenated resin, such as benzylated and phenacylhologenated resin, etc., as well as merrifield resin.

[Method H]

The reaction of a compound (LIV) and a compound (III) is carried out in the same manner as the reaction of the compound (II) and the compound (III). The subsequent reaction of a compound (IX) or its reactive derivative is carried out in the same manner as the reaction of the compound (VIII) and a compound (IX) or its reactive derivative.

The reaction to prepare a compound (LVII) by reacting a compound (LV) and a compound (LVI) is carried out in a solvent in the presence or absence of an acid scavenger.

As an acid scavenger, is preferably used an organic base, such as N,N-diisopropylethylamine, N-methylmorpholine, triethylamine, pyridine, N,N-dimethylaminopyridine, etc., an inorganic base, such as sodium hydroxide, sodium carbonate, potassium carbonate, sodium hydrogen carbonate, cesium carbonate, sodium hydride, etc. As a solvent, is preferably used a solvent which does not disturb the reaction, such as xylene, N,N-dimethylformamide, tetrahydrofuran, dimethoxyethane, dimethyl sulfoxide, toluene, etc. The reaction preferably proceeds at −10° C. to room temperature, especially at 0° C. to room temperature.

The reaction to prepare a compound (LIII) by reacting a compound (LVII) with a compound (LII) is carried out in the same manner as the reaction to prepare the compound (IV) by reacting the compound (II) with the compound (III).

The reaction with a compound (VI) after oxidation of a compound (LIII) is carried out in the same manner as the reaction to prepare the compound (I) by reacting the compound (VI) or its salt and the compound (V) prepared by oxidation of the compound (IV).

The reaction with a compound (VI) after reacting a compound (LV) and a compound (LII) is carried out in the same manner as the reaction of the compound (LI) with the compound (LII), and the reaction of the compound (V) with the compound (VI).

The reaction with a compound (LII) after reacting a compound (LV) and a compound (VI) is carried out in the same manner as the reaction of the compound (V) with the compound (VI), and the reaction of the compound (LI) with the compound (LII).

[Method I]

The reaction to prepare a compound (LIX) by treating a compound (LVIII) with carbon dioxide is the same manner as the reaction to prepare the compound (XII) by treating the compound (XI) with carbon dioxide.

The reaction of a compound (LIX) and a compound (LVI) is carried out in the same manner as the reaction to prepare the compound (LVII) by reacting the compound (LV) with the compound (LVI).

The reaction to prepare a compound (LX) by reacting a compound (IX) or its salt is carried out in the same manner as the reaction to prepare the compound (I) by reacting the compound (VIII) with the compound (IX).

The reaction to prepare a compound (LXI) by reacting a compound (LX) and a compound (LII) is carried out in the same manner as the reaction to prepare the compound (LIII) by reacting the compound (LI) with the compound (LII).

The reaction of a compound (LXI) and a compound (VI) or its salt is carried out in the same manner as the reaction to prepare the compound (VII) by reacting the compound (V) with the compound (VI).

The subsequent oxidation of the compound thus prepared is carried out in the same manner as the oxidation of the compound (IV).

The subsequent reaction to prepare a compound (I-d) by reacting the compound thus obtained with a compound (III) is carried out in the same manner as the reaction to prepare the compound (VII) by reacting the compound (V) and the compound (VI).

[Method J]

The reaction to prepare a compound (LXIII) by protection of a compound (LXII) is carried out in the same manner as the reaction to prepare the compound (IV) by reacting the compound (II) with the compound (III). As a protective group, is used, for example a lower alkyl group which is optionally substituted.

The reaction to prepare a compound (LXIV) by reacting a compound (LXIII) and a compound (IX) or its reactive derivative is carried out in the same manner as the reaction to prepare the compound (I) by reacting the compound (VIII) with the compound (IX) or its reactive derivative.

The reaction to prepare a compound (LXV) by deprotecting a compound (LXIV) is carried out in the same manner as the reaction to prepare the compound (XXXVII) by deprotecting the compound (XXXVI).

The reaction to prepare a compound (LXVII) by reacting a compound (LXV) and a compound (LXVI) is carried out in the presence or absence of a base in a solvent. As a base, is preferably used an organic base, such as N,N-diisopropylethylamine, N-methylmorpholine, triethylamine, pyridine, N,N-dimethylaminopyridine, etc., an inorganic base, such as sodium hydroxide, sodium carbonate, potassium carbonate, sodium hydrogen carbonate, etc. As a solvent, is preferably used a solvent which does not disturb the reaction, such as methanol, ethanol, acetone, N,N-dimethylformamide, tetrahydrofuran, etc. The reaction preferably proceeds at −10° C. to 100° C., especially at 60° C. to 70° C.

The reaction of a compound (LXVII) and a compound (XLVI) is carried out in the same manner as the reaction of the compound (XLV) with the compound (XLVI).

Thus obtained compound (I) is optionally, formed into its pharmacologically acceptable salt.

The starting material (II) is prepared in accordance with the method described in Journal of American Chemical Society Vol. 65, page 350 (1943)

EXAMPLE

Examples of the compound (I) of the present invention which is prepared by the above illustrated methods are illustrated as follows, but thereby the present invention should not be limited.

Example 1

(1) A 1.6 M solution of n-butyl lithium in hexane (96.5 ml, 2.3 mol) is added to a solution of diisopropylamine (15.62 g, 2.3 mol) in tetrahydrofuran (400 ml) over a period of 10 minutes to on a dry ice-acetone bath, and the reaction mixture is stirred for 30 minutes. A solution of 2,4-dichloropyrimidine (10.00 g, 1 mol) in tetrahydrofuran (350 ml) is added thereto over a period of 2 hours, and the mixture is stirred for additional 1 hour. A solution of 3,4,5-trimethoxybenzaldehyde (19.75 g, 1.5 mol) in tetrahydrofuran (100 ml) is added thereto over a period of 1 hour and the mixture is further stirred for 1 hour.

The reaction mixture is poured through a cannula into a mixture (ca. 1.5 L) of ice and 10% hydrochloric acid (1.5 L) and the mixture is extracted twice with each 500 ml of ethyl acetate. The organic layer is collected, washed with 10% hydrochloric acid, water and an aqueous saturated sodium chloride solution, dried over anhydrous sodium sulfate, and condensed in vacuo. The residue is separated by silica gel chromatography (solvent; chloroform: hexane: ethyl acetate=5:5:2→hexane:ethyl acetate=3:1→2:1). The desired fraction is collected to condensed in vacuo and the residue is separated by silica gel chromatography (solvent; chloroform: ethyl acetate=30:1→15:1) to be crystallized from n-hexane to give 2,4-dichloro-5-[hydroxy-(3,4,5-trimethoxyphenyl)methyl]pyrimidine 10.83 g (yield 47%) as a slightly greenish brown crystalline powder. mp 115–118° C.

(2) A mixture of the compound prepared in above (1) 10.83 g, manganese dioxide 15 g and chloroform 200 ml is stirred for 16 hours at room temperature. Further manganese dioxide 35 g and chloroform 60 ml are added thereto and the mixture is stirred for 24 hours at room temperature.

After removal of insoluble materials by Celite, the filtrate is concentrated in vacuo. The residue is purified by silica gel chromatography (solvent; hexane:ethyl acetate=3:1) to be concentrated in vacuo to give 2,4-dichloro-5-(3,4,5-trimethoxyphenylcarbonyl)pyrimidine, 9.30 g (yield 86%) as a yellow prism. mp 140–141° C.

(3) To a suspension of the compound prepared in above (2) 15 g in anhydrous toluene 200 ml is added triethylamine 6.63 g. A solution of 3-chloro-4-methoxybenzylamine 7.5 g in toluene 50 ml is added thereto over a period of 20 minutes at 0° C. When the greater part of the amine is added, a white powderish solid precipitates. The mixture is further stirred at room temperature for 1 hour.

After stirring the reaction mixture for 2 hours, 3-chloro-4-methoxybenzylamine 0.75 g is further added thereto. The mixture is stirred for additional 1 hour and is filtrated to give a white substance like cake, followed by washing with toluene. The substance like cake consists of a mixture of the desired product and triethylamine hydrochloride. The white cake is dissolved in toluene, and treated with ethyl acetate, tetrahydrofuran and then water and sodium carbonate. The organic layer is washed with an aqueous sodium chloride solution and brine, in order. The solution is dried over anhydrous sodium sulfate and is concentrated.

The residue is dissolved in chloroform, filtered and concentrated in vacuo. The residue is recrystallized from a mixture of chloroform and ether, respectively about 100 ml, and the crystals are filtered. Th resulting cake like substances are well washed with ether and dried on air to give 2-chloro-5-(3,4,5-trimethoxyphenylcarbonyl)-4-(3-chloro-4-methoxybenzylamino)pyrimidine 20.21 g (yield 97%). mp 165° C.

(4) To a solution of 2-(hydroxymethyl)pyridine 68 mg in tetrahydrofuran 3 ml is added sodium hydride 25 mg (60% suspension in oil), and the mixture is stirred for 30 minutes to give a white suspension. A solution of the compound prepared in above (3) 45 mg in tetrahydrofuran 3 ml is added to the white suspension. During addition color of the suspension is changed to yellow from white. After the mixture is stirred for 1 hour, the reaction mixture is concentrated in vacuo. The residue is poured into ice-water and the mixture is extracted with ethyl acetate. The organic layer is washed with water and brine in order, dried over anhydrous sodium sulfate, and concentrated in vacuo and dried. The residue ispurified by silica gel chromatography (solvent; chloroform:methanol=50:1) to give a single spot on a thin-layer chromatograph.

The desired fraction is evaporated to dryness and the residue is triturated with ethyl acetate-hexane-diisopropyl ether to give 2-(2-pyridylmethoxy)-5-(3,4,5-trimethoxyphenylcarbonyl)-4-(3-chloro-4-methoxybenzylamino)pyrimidine 56.0 mg as white crystals. mp 129° C.

Example 2

A solution of 2-methylaminoethanol 100 mg in dimethylformamide 1 ml is added at room temperature to a solution of 2-chloro-5-(3,4,5-trimethoxyphenylcarbonyl)-4-(3-chloro-4-methoxybenzylamino)pyrimidine (120 mg) prepared in above Example 1-(3) in dimethylformamide (1 ml). The mixture is stirred at room temperature for 1 hour and thereto is added water 50 ml. The mixture is extracted with ethyl acetate-chloroform and the extract is subjected to silica gel chromatography (solvent: chloroform-methanol 5%) to give 2-(N-methyl-N-(2-hydroxyethyl)amino)-5-(3,4,5-trimethoxyphenylcarbonyl)-4-(3-chloro-4-methoxybenzylamino)pyrimidine 110 mg as white crystals. mp 166.5–168° C.

Example 3

A mixture of 101 mg of 2-chloro-5-(3,4,5-trimethoxyphenylcarbonyl)-4-(3-chloro-4-methoxybenzylamino)pyrimidine prepared in above Example 1-(3), potassium cyanide 27.5 mg and palladium chloride triphenylphosphine 3 mg in dimethylformamide 3 ml is stirred at 120° C. for 7 hours. To the reaction mixture is added 4-hydroxypiperidine, and the mixture is stirred at room temperature for 1 hour. The reaction mixture is poured into water and is twice extracted with ethyl acetate. The extract is washed with water and brine in order, dried over anhydrous sodium sulfate and evaporated to dryness to give 2-cyano-5-(3,4,5-trimethoxyphenylcarbonyl)-4-(3-chloro-4-methoxybenzylamino)pyrimidine as a yellow solid, 7.5 mg. mp 140–143° C.

Examples 4–45

A compound prepared in Example 1-(3) and the corresponding starting material is treated in the same manner as Example 1-(4) or Example 2 to prepare compounds illustrated in the following Table 1.

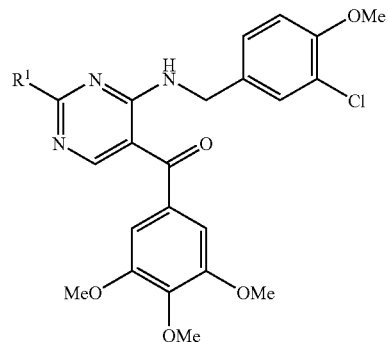

TABLE 1

| Example No. | R¹ | Physical Property, etc. |
|---|---|---|
| 4 | MeO-C₆H₃(Cl)-CH₂-NH- | mp 98° C. |
| 5 | 2-pyridyl-CH₂CH₂-O-CH₃ | mp 112–114° C. |
| 6 | 2-pyridyl-CH₂CH₂CH₂-O-CH₃ | mp 98° C. |
| 7 | 2-pyridyl-CH₂-NH- | mp 166–168° C. |
| 8 | imidazolyl- | mp 210–201° C. |
| 9 | 4-hydroxy-1-piperidinyl | mp 132–133° C. |

TABLE 1-continued

| Example No. | R¹ | Physical Property, etc. |
|---|---|---|
| 10 | 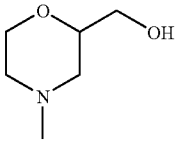 | mp 175–176° C. |
| 11 | 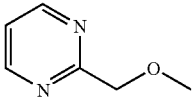 | mp 169–170° C. |
| 12 | 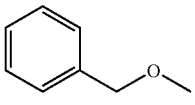 | mp 129° C. |
| 13 | 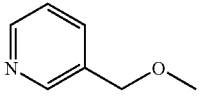 | mp 164–165° C. |
| 14 | 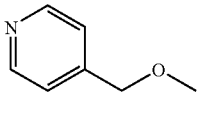 | mp 183–184° C. |
| 15 | 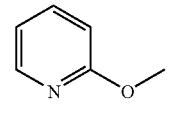 | Foam<br>IR(nujol): 1622, 3284 cm⁻¹<br>MS(m/z): 537(M + H)⁺ |
| 16 | 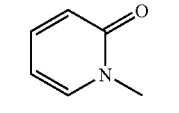 | Foam<br>IR(nujol): 1626, 1675, 3289 cm⁻¹<br>MS(m/z): 537(M + H)⁺ |
| 17 | 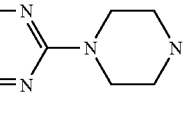 | mp 210–201° C. |
| 18 | MeO— | mp 136–138° C. |
| 19 | Me₂N— | mp 127° C. |
| 20 | 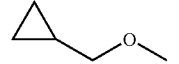 | mp 98–100° C. |
| 21 | 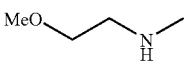 | mp 166–168° C. |
| 22 | 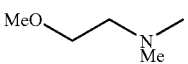 | mp 121–123° C. |
| 23* | 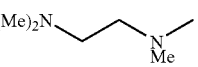 | Powder<br>IR(nujol): 1640 cm⁻¹<br>MS(m/z): 544(M + H)⁺ |
| 24 | 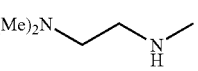 | mp 112–114° C. |
| 25 | 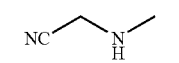 | mp 234–236° C. |

TABLE 1-continued

| Example No. | R¹ | Physical Property, etc. |
|---|---|---|
| 26 | 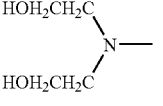 | mp 127–129.5° C. |
| 27** | 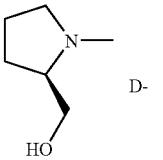 D- | Powder<br>IR(nujol): 1637 cm⁻¹<br>MS(m/z): 543(M + H)⁺ |
| 28** | 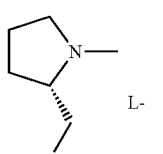 L- | Powder<br>IR(nujol): 1636 cm⁻¹<br>MS(m/z): 543(M + H)⁺ |
| 29 | 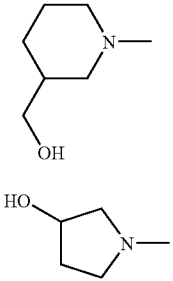 | mp 139–140° C. |
| 30 | | mp 140–142° C. |
| 31 | | mp 191° C. |
| 32 | | mp 176–177° C. |
| 33 | | mp 155–156° C. |
| 34 | | mp 155–156° C. |
| 35 | | mp 176–178° C. |
| 36 | | mp 154–157° C. |
| 37 | | mp 139–142° C. |

TABLE 1-continued

| Example No. | R¹ | Physical Property, etc. |
|---|---|---|
| 38 | Me-pyridine-CH₂-O-Me | mp 128–131° C. |
| 39 | pyridine(3-OMe)-CH₂-O-Me | mp 153–156° C. |
| 40 | MeN-piperidine-O-Me | Powder IR(nujol): 1645 cm⁻¹ MS(m/z): 557(M + H)⁺ |
| 41 | MeO-pyrimidine-CH₂-O-Me | mp 128° C. |
| 42 | MeO-CH₂CH₂-O-Me | mp 113–115° C. |
| 43 | HO-CH₂CH₂-O-Me | mp 175–176° C. |
| 44 | Me₂N-CH₂CH₂-O-Me | Foam IR(nujol): 1619, 3304 cm⁻¹ MS(m/z): 531(M + H)⁺ |
| 45 | morpholine-CH₂-O-Me | Foam IR(nujol): 3314, 1619 cm⁻¹ MS(m/z): 559(M + H)⁺ |

*trihydrochloride
**dihydrochloride

Examples 46–63

A compound prepared in Example 1-(2) and the corresponding starting material is treated in the same manner of Example 1-(3) and Example 1-(4) to prepare compounds illustrated in the following Table 2.

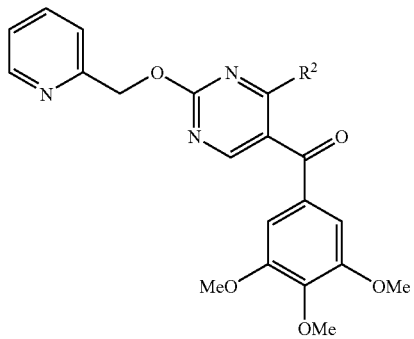

TABLE 2

| Example No. | R² | Physical Property etc. |
|---|---|---|
| 46 | —NH—CH₂—C₆H₄—Cl (3-Cl) | mp 120–122° C. |
| 47 | —NH—CH₂—C₆H₃(OMe)(NH₂) | mp 97–99° C. |
| 48 | —NH—CH₂—C₆H₃(OMe)(NHMe) | mp 149–151° C. |
| 49 | —NH—CH₂—C₆H₃(OMe)(NMe₂) | Amorphous IR(nujol): 1621 cm⁻¹ MS(m/z): 560(M + H)⁺ |
| 50 | —NH—CH₂—C₆H₃(OMe)(NO₂) | mp 124–127° C. |
| 51 | —NH—CH(Me)—C₆H₃(OMe)(Cl) | Amorphous IR(nujol): 1621 cm⁻¹ MS(m/z): 565(M + H)⁺ |
| 52 | —NH—CH₂—(1-naphthyl) | mp 136–136.5° C. |
| 53 | —NH—CH₂—C₆H₄—OMe (4-OMe) | mp 91–91.5° C. |
| 54 | —NH—CH₂—(2-naphthyl) | Oil IR(neat): 3301, 1620 cm⁻¹ MS(m/z): 537(M + H)⁺ |
| 55 | —NH—CH₂—C₆H₃(OMe)₂ (3,5-diOMe) | mp 134–135° C. |
| 56 | —NH—CH₂—(5-indolyl) | mp 189–191° C. |

TABLE 2-continued

| Example No. | R² | Physical Property etc. |
|---|---|---|
| 57 | indanyl-NH- | Oil<br>IR(neat):<br>3288, 1621 cm⁻¹<br>MS(m/z): 513(M + H)⁺ |
| 58 | -NH-CH₂-C₆H₄-CF₃ | Oil<br>IR(neat):<br>3301, 1619 cm⁻¹<br>MS(m/z): 555(M + H)⁺ |
| 59 | -NH-CH₂-C₆H₄-F | mp 130–131° C. |
| 60 | methylenedioxybenzyl-NH- | mp 147–148° C. |
| 61 | benzyl-NH- | mp 119–119.5° C. |
| 62 | 3,4-dimethoxybenzyl-NH- | mp 121–122° C. |
| 63 | 2-pyridylmethoxy- | mp 153.5–154° C. |

Example 64

A mixture of 2-(2-pyridylmethoxy)-5-(3,4,5-trimethoxyphenylcarbonyl)-4-(3-amino-4-methoxybenzylamino)pyrimidine 53 mg prepared in Example 47, acetic acid anhydride 8.6 mg, pyridine 16 mg and methylene chloride 3 ml is stirred at room temperature for 2 hours. To the reaction mixture is further added acetic acid anhydride 8 mg and the mixture is stirred for 1.5 hours. To the reaction mixture are added ethyl acetate, water and an aqueous saturated sodium hydrogen carbonate solution in order. The organic layer is separated, washed with brine and dried over anhydrous sodium sulfate.

After filtration of sodium sulfate, the filtrate is concentrated in vacuo. The residue is purified by being subjected to silica gel chromatography (solvent: ethyl acetate→chloroform:methanol=20:1) and triturated with diethyl ether to give 2-(2-pyridylmethoxy)-5-(3,4,5-trimethoxyphenylcarbonyl)-4-(3-acetylamino-4-methoxybenzylamino)pyrimidine as colorless crystals, 55 mg.

mp 193.5–195.5° C.

Example 65

To a solution of 2-(2-pyridylmethoxy)-5-(3,4,5-trimethoxyphenyl-carbonyl)-4-(3-metylamino-4-methoxybenzylamino)pyrimidine (prepared in Example 48) 42 mg in methylene chloride 3 ml are added mesyl chloride 48 mg and triethylamine 69 mg, for three times at one hour intervals. The reaction mixture is stirred for 1 hour at room temperature. Ethyl acetate and an aqueous saturated sodium hydrogen carbonate solution is added thereto. The organic layer is separated, washed with brine and dried over anhydrous sodium sulfate. After filtration of sodium sulfate the filtrate is concentrated in vacuo and the residue is purified by preparative thin-layer chromatograph (2 plates, solvent: ethyl acetate) to give 2-(2-pyridylmethoxy)-5-(3,4,5-trimethoxyphenylcarbonyl)-4-[4-methoxy-3-(N-methylmethansulfonylamino)benzylamino]pyrimidine as a colorless amorphous 20 mg.

IR (Nujol): 1621,1584 cm⁻¹ MS (m/z): 624 (M+H)⁺

Example 66

A mixture of 2,4-dichloro-5-(3,4,5-trimethoxyphenylcarbonyl)pyrimidine (prepared in Example 1-(2)) 150 mg and 3-chloro-4-methoxyphenylmethanol 79.2 mg in tetrahydrofuran 3 ml are treated with sodium hydride 19.2 mg (suspension in 60% oil) at 0° C. for 30 minutes. To the reaction mixture are added 2-pyridylmethanol 47.7 mg and sodium hydride 17.5 mg (suspension in 60% oil) in order at 0° C. After stirring for 30 minutes, an aqueous sodium hydrogen carbonate solution is added thereto. The mixture is extracted with ethyl acetate and the extract is subjected to preparative thin-layer chromatography to give following compounds:

(A) 2-(3-Chloro-4-methoxybenzyloxy)-5-(3,4,5-trimethoxyphenylcarbonyl)-4-(2-pyridylmethoxy)pyrimidine, 40.1 mg, mp 172–173° C.

(B) 2-(2-Pyridylmethoxy)-5-(3,4,5-trimethoxyphenyl carbonyl)-4-(3-chloro-4-methoxybenzyloxy)pyrimidine, 51.9 mg, mp 108–109° C.

(C) 2,4-Bis(3-chloro-4-methoxybenzyloxy)-5-(3,4,5-trimethoxyphenylcarbonyl)pyrimidine, 85.7 mg, mp 138–139° C.

Example 67

(1) A mixture of 2-methylthio-4-chloro-5-ethoxycarbonylpyrimidine 1.0 g, (3-chloro-4-methoxyphenyl)methylamine 0.81 g, triethylamine 0.66 ml and tetrahydrofuran 12 ml is stirred for 4 hours at room temperature. The reaction mixture is diluted with an aqueous 10% citric acid solution and the mixture is extracted twice with ethyl acetate. The combined organic layer is washed with water and an aqueous saturated sodium chloride solution, dried over anhydrous sodium sulfate and concentrated in vacuo. The residue is purified by silica gel chromatography (solvent; hexane: ethyl acetate=5:1) and concentrated in vacuo to give a colorless oil. The oil is left overnight at room temperature to give 2-methylthio-5-ethoxycarbonyl-4-(3-chloro-4-methoxybenzylamino)pyrimidine as crystals, 1.58 g. mp 82–83° C.

(2) To a solution of 2-methylthio-5-ethoxycarbonyl-4-(3-chloro-4-methoxybenzylamino)pyrimidine (prepared in above (1)) 300 mg in chloroform 5 ml is added under ice cooling m-chloroperbenzoic acid (80%) 369 mg. The mixture is stirred at room temperature for 5 hours. Further m-chloroperbenzoic acid (80%) 106 mg and chloroform 6 ml are added thereto and the mixture is stirred at room temperature for 2 hours.

The reaction mixture is diluted with an aqueous saturated sodium hydrogen carbonate solution and the water layer is extracted with chloroform. The combined organic layer is washed with water and an aqueous saturated sodium chloride solution, dried over anhydrous sodium sulfate and concentrated in vacuo. The residue is separated with silica gel chromatography (solvent; hexane:ethyl acetate=3:1→3:

2) to give 2-methylsulfonyl-5-ethoxycarbonyl-4-(3-chloro-4-methoxybenzylamino)pyrimidine as a colorless caramel, 133 mg.

IR(CHCl$_3$)cm$^{-1}$: 3333, 1695, 1593, 1572, 1503 MS(m/z): 400(M+H)$^+$ (3) A mixture of 2-hydroxymethylpyridine 32 mg and sodium hydride (suspension in 60% oil) 11.8 mg in tetrahydrofuran 2.5 ml is stirred at room temperature for 5 minutes. To the mixture is added at room temperature a solution of 2-methylsulfonyl-5-ethoxycarbonyl-4-(3-chloro-4-methoxybenzylamino)pyrimidine (prepared in the above (2)) 118 mg in tetrahydrofuran 2.5 ml, and the mixture is stirred for 30 minutes at room temperature. The reaction mixture is diluted with an aqueous 10% citric acid solution and extracted twice with ethyl acetate. The combined organic layer is washed with water and an aqueous saturated sodium chloride solution, dried over anhydrous sodium sulfate and concentrated in vacuo. The residue is purified by silica gel chromatography (solvent; chloroform:ethyl acetate=4:1→1:2) and concentrated in vacuo to give 2-(2-pyridylmethoxy)-5-ethoxycarbonyl-4-(3-chloro-4-methoxybenzylamino)pyrimidine as a colorless caramel, 106 mg.

IR(CHCl$_3$)cm$^{-1}$: 3337, 1685, 1591, 1502, 1451, 1440, 1421 MS(m/z): 429(M+H)$^+$

Example 68

(1) To a solution of 2-methylthio-5-ethoxycarbonyl-4-(3-chloro-4-methoxybenzylamino)pyrimidine (prepared in Example 67-(1)) 500 mg in chloroform 5 ml is dropped a solution of m-chloroperbenzoic acid (80%) 323 mg in chloroform 4 ml over a period of 30 minutes under ice cooling. The mixture is stirred at the same temperature for 1 hour.

The reaction mixture is diluted with an aqueous saturated sodium hydrogen carbonate solution. The chloroform layer is separated, washed with water and an aqueous saturated sodium chloride solution, dried over anhydrous sodium sulfate and then concentrated in vacuo to give 2-methylsulfinyl-5-ethoxycarbonyl-4-(3-chloro-4-methoxybenzylamino)pyrimidine as a colorless caramel, 545 mg.

IR(neat)cm$^{-1}$: 3333, 1694, 1588, 1574, 1503, 1463, 1440 MS(m/z): 384(M+H)$^+$ (2)-i) A mixture of 2-hydroxymethylpyridine 1,46 g, sodium hydride (suspension in 60% oil) 0.521 g and tetrahydrofuran 20 ml is stirred at room temperature for 20 minutes to prepare a suspension. The resulting suspension is dropped to a solution of the compound (prepared in the above (1)) 4.90 g in tetrahydrofuran 25 ml over a period of 10 minutes under ice cooling and the mixture is stirred at the same temperature for 1 hour.

The reaction mixture is diluted with an aqueous 10% citric acid solution in ice and the solution is extracted twice with ethyl acetate. The combined organic layer is washed with a 10% aqueous citric acid solution, water and an aqueous saturated sodium chloride solution, dried over anhydrous sodium sulfate and concentrated in vacuo. The residue is separated by silica gel chromatography (solvent; chloroform:ethyl acetate=2:1→3:2, then chloroform: methanol=10:1) and the first fraction is concentrated in vacuo to give 2-(2-pyridylmethoxy)-5-ethoxycarbonyl-4-(3-chloro-4-methoxybenzylamino)pyrimidine as a slightly yellowish caramel (which is the same compound prepared in Example 67-(3)), 2.25 g.

(2)-ii) The second fraction separated by the above silica gel chromatography is concentrated in vacuo, and the residue is subjected to silica gel chromatography (solvent; chloroform:ethyl acetate=10:1, chloroform: methanol=10:1) to be divided into the third fraction and the forth fraction.

The third fraction is concentrated in vacuo, and crystallized from isopropyl ether to give 2-(2-pyridylmethoxy)-5-(2-pyridylmethoxycarbonyl)-4-(3-chloro-4-methoxybenzylamino)pyrimidine as a colorless crystalline powder, 234 mg. mp 115–120° C.

(2)-iii) The above forth fraction is concentrated in vacuo to give 2-hydroxy-5-ethoxycarbonyl-4-(3-chloro-4-methoxybenzylamino)pyrimidine as a colorless crystalline powder, 2.06 g. mp 117–122° C.

(3) To a mixture of the compound (prepared in the above (2)-i)) 4.48 g in ethanol 80 ml and water 40 ml is added an aqueous 2N sodium hydroxide solution 52 ml under ice cooling, and the reaction mixture is stirred at room temperature for 13 hours. The reaction mixture is neutralized under ice cooling with 10% hydrochloric acid and 10% citric acid, and concentrated in vacuo. The resulting suspension is diluted with water 100 ml and left under ice cooling for 30 minutes. The precipitate is collected by filtration and washed with water, isopropyl alcohol, diisopropyl ether and n-hexane, and dried in vacuo at 70° C. to give 2-(2-pyridylmethoxy)-5-carboxy-4-(3-chloro-4-methoxybenzylamino) pyrimidine as a colorless crystalline powder, 3.84 g. mp 201–203° C.

(4) To a solution of the compound (prepared in the above (3)) 51 mg in methylene chloride 5 ml is added thionyl chloride 10 drops and the mixture is stirred at room temperature for 1 hour, and volatile substances are removed by vacuum distillation. The residue is dissolved in methylene chloride 3 ml and thereto are added 4-hydroxypyperidine 64 mg and triethylamine 89 µl. The mixture is stirred at room temperature for 30 minuets.

The reaction mixture is diluted with water and the solution is extracted twice with ethyl acetate. The combined organic layer is washed with an aqueous saturated sodium hydrogen carbonate solution, water and an aqueous saturated sodium chloride solution, dried over anhydrous sodium sulfate and then concentrated in vacuo. The residue is separated by preparative thin-layer chromatography (solvent; chloroform:methanol=10:1 to give the following three compounds:

(A) 2-(2-Pyridylmethoxy)-5-(4-hydroxypiperidylcarbonyl-4-(3-chloro-4-methoxybenzylamino)pyrimidine as a colorless amorphous, 27 mg.

IR(neat)cm$^{-1}$: 3334, 1621, 1614, 1583, 1575, 1503, 1442, 1412 MS(m/z): 484(M+H)$^+$ (B) 2-(2-Pyridylmethoxy)-5-(4-chlorosulfinyloxypiperidyl carbonyl)-4-(3-chloro-4-methoxybenzylamino)pyrimidine as a colorless amorphous, 18 mg.

IR(nujol)cm$^{-1}$: 3333, 1619, 1582, 1501, 1458, 1411 MS(m/z): 466(M+H)$^+$ (C) 2-(2-Pyridylmethoxy)-5-[4-(4-piperidyloxysulfinyloxyl)piperidylcarbonyl]-4-(3-chloro-4-methoxybenzylamino)pyrimidine as a colorless amorphous, 3 mg.

MS (m/z): 631 (M+H)$^+$

Example 69

A mixture of 2-(2-pyridylmethoxy)-5-carboxy-4-(3-chloro-4-methoxybenzylamino)pyrimidine (prepared in Example 68-(3)) 100 mg, 2-hydroxymethylpyrimidine 30 mg, 1-(3-dimethylaminopropyl)-3-ethylcarbodiimido hydrochloride 53 mg and dimethylaminopyridine 33 mg in dimethylformamide 3 ml is stirred at room temperature for 2 hours. The reaction mixture is poured into water and extracted with ethyl acetate. The organic layer is washed with brine, dried over anhydrous sodium sulfate and concentrated in vacuo. The residue is purified with preparative thin-layer chromatography (solvent; chloroform:methanol=25:1) and triturated with diethyl ether to give 2-(2-pyridylmethoxy)-5-(2-pyrimidinylmethoxycarbonyl-4-(3-chloro-4-methoxybenzylamino) pyrimidine 60 mg. mp 137–139° C.

Example 70

(1) A mixture of 2-(2-pyridylmethoxy)-5-carboxy-4-(3-chloro-4-methoxybenzylamino)pyrimidine (prepared in Example 68-(3)) 130 mg, methylene chloride 6 ml and thionyl chloride 0.10 ml is stirred at room temperature for 1 hour. The volatile substances are removed in vacuo and further azeotropic separation thereof is carried out in vacuo by addition of methylene chloride. The residue is diluted with methylene chloride 3 ml.

The suspension is divided in two parts, and one part is diluted with methylene chloride 1 ml and the mixture is added to methanol 1 ml under ice cooling. The reaction mixture is diluted with an aqueous saturated sodium carbonate solution and extracted twice with ethyl acetate. The combined organic layer is washed with an aqueous saturated sodium hydrogen carbonate solution, water and an aqueous saturated sodium chloride solution, dried over anhydrous sodium sulfate and concentrated in vacuo. The residue is purified with silica gel chromatography (solvent; chloroform:ethyl acetate=2:1→1:1) and concentrated in vacuo. The resulting residue is triturated with isopropyl ether to give 2-(2-pyridylmethoxy)-5-(methoxycarbonyl)-4-(3-chloro-4-methoxybenzylamino)pyrimidine as a colorless crystalline powder, 37 mg. mp 135–136° C.

(2) On the other hand a mixture of the residual part of the above suspension (other part), methylene chloride 3 ml and ammonium hydroxide 2 ml is stirred under ice cooling for 1 hour. The reaction mixture is diluted with water and extracted twice with ethyl acetate. The combined organic layer is washed with an aqueous 10% sodium hydroxide solution, water and an aqueous saturated sodium chloride solution, dried over anhydrous sodium sulfate and then concentrated in vacuo. The residue is purified with silica gel chromatography (solvent; chloroform:methanol=20:1→10:1), concentrated in vacuo, and triturated with isopropyl ether to give 2-(2-pyridylmethoxy)-5-(aminocarbonyl)-4-(3-chloro-4-methoxybenzylamino)pyrimidine as a colorless crystalline powder, 45 mg. mp 208–209° C.

Example 71

To a solution of 2-(2-pyridylmethoxy)-5-carboxy-4-(3-chloro-4-methoxybenzylamino)pyrimidine (prepared in Example 68-(3)) 100 mg in methylene chloride 3.5 ml is added at room temperature thionyl chloride 0.02 ml, and the mixture is stirred at room temperature for 1 hour. The volatile substances are removed in vacuo and further azeotropic separation thereof is carried out in vacuo by addition of methylene chloride. The residue is suspended in methylene chloride 8 ml. The suspension is added under ice cooling under stirring to a mixture of N-methylmethoxyamine hydrochloride 29 mg and an aqueous saturated sodium hydrogen carbonate solution 3 ml. The mixture is stirred at room temperature for 1 hour.

The reaction mixture is diluted with water and extracted twice with ethyl acetate. The combined organic layer is washed with an aqueous saturated sodium hydrogen carbon-ate solution, water and an aqueous saturated sodium chloride solution, dried over anhydrous sodium sulfate and then concentrated in vacuo. The residue is purified with silica gel chromatography (solvent; ethyl acetate) and concentrated in vacuo to give 2-(2-pyridylmethoxy)-5-(N-methyl-N-methoxyaminocarbonyl)-4-(3-chloro-4-methoxybenzylamino) pyrimidine as a colorless caramel, 81 mg.

IR(neat)cm$^{-1}$: 3331, 1621, 1581, 1502, 1439, 1410
MS(m/z): 444(M+H)$^+$

Examples 72–75

A compound prepared in Example 68-(3) and the corresponding starting material is treated in the same manner as Example 69 and Example 70 to prepare compounds illustrated in the following Table 3.

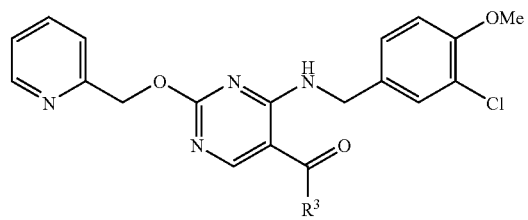

TABLE 3

| Example No. | R$^3$ | Physical property etc. |
|---|---|---|
| 72 | —O—CH$_2$CH$_2$—NMe$_2$ | Amorphous<br>IR: 1688 cm$^{-1}$<br>MS(m/z): 472(M + H)$^+$ |
| 73 | —NH—CH$_2$-(2-pyridyl) | mp 100–102° C. |
| 74 | —NH—CH$_2$CH$_2$-(2-pyridyl) | mp 140–142° C. |
| 75 | —N(piperazinyl)—CH$_3$ | mp 128–129° C. |

Example 76

A mixture of 2-(2-pyridylmethoxy)-5-(3,4,5-trimethoxyphenylcarbonyl)-4-(3-chloro-4-methoxybenzylamino)pyrimidine (prepared in Example 1-(4)) 10.0 mg, methyl chlorocarbonylacetate 24 µl and anhydrous toluene 2 ml is reacted for 6 hours at room temperature and for 1 hour at refluxing temperature. The reaction mixture is cooled and thereto are added ethyl acetate and water. The organic layer is separated and washed with water, an aqueous saturated sodium hydrogen carbonate solution and brine in order, dried over anhydrous sodium sulfate and then subjected to silica gel chromatography (solvent; chloroform:ethyl acetate=1:1→ethyl acetate) to give 2-hydroxy-5-(3,4,5-trimethoxyphenylcarbonyl)-4-(3-chloro-4-methoxybenzylamino)pyrimidineas a partial crystalline oil, 6.9 mg.

MS(m/z): 458(M–H)$^-$

Example 77

The compound prepared in Example 68-(1) is dissolved in tetrahydrofuran 40 ml, and to the solution are added a mixture of L-prolinol 1.50 g and triethylamine 1.60 g in tetrahydrofuran 10 ml at room temperature. The mixture is stirred overnight and is diluted with ethyl acetate. After washing with an aqueous saturated sodium hydrogen carbonate solution and brine, the organic layer is dried over anhydrous sodium sulfate and the solvent is removed in vacuo. The residue is purified with silica gel chromatography (solvent; chloroform) and crystallized from ether-n-hexane to give (S)-4-(3-chloro-4-methoxybenzylamino)-5-ethoxycarbonyl-2-(2-hydroxymethyl-1-pyrrolidinyl) pyrimidine, 4.72 g. mp 88–90° C. MS(m/z): 421(M+H)$^+$

Example 78

2-Methylthio-4-(3-nitro-4-methoxybenzylamino)-5-ethoxycarbonylpyrimidine as pale yellow crystals, 3.15 g (mp 99–100.5° C.) is obtained by treating 2-methylthio-4-chloro-5-ethoxycarbonylpyrimidine 2.0 g and 3-nitro-4-methoxybenzylamine 1.72 g in the same manner as Example 67-(1).

Example 79

2-Methylthio-4-(3-chloro-4-methoxybenzylamino)-5-ethoxycarbonylpyrimidine (prepared in Example 67-(1)) 2.00 g is suspended in dimethyl sulfoxide 10 ml, and the suspension is treated with a 10% aqueous sodium hydroxide solution 10 ml. The reaction mixture is still in suspension even 6 hours later. After addition of dimethyl sulfoxide 5 ml the mixture is stirred at room temperature over night. The resulting clear reaction solution is acidified with citric acid. The excess water (about 50 ml) is added thereto and resulting precipitate is filtered, washed with isopropylalcohol and then isopropyl ether, and concentrated in vacuo to give 2-methylthio-4-(3-chloro-4-methoxybenzylamino)-5-carboxypyrimidine as a pale yellow impalpable powder, 1.864 g. mp 238–240° C. (decomposition)

Example 80

2-Methylthio-4-(3-chloro-4-methoxybenzylamino)-5-carboxypyrimidine (prepared in Example 79) 0.500 g, 2-pyridylmethylamine 0.1749 g, 1-hydroxybenzotriazole 0.1987 g, 1,2-dichloroethane hydrochloride 0.3102 g and anhydrous dimethylformamide 5 ml are mixed together and stirred at 0° C. overnight and triturated with ethyl acetate-isopropyl ether to give 2-methylthio-4-(3-chloro-4-methoxybenzylamino)-5-[N-(2-pyridylmethyl)carbamoyl]pyrimidine as a colorless powder, 0.5966 g. mp 143–144.5° C.

Example 81

A mixture of 2-methylthio-4-(3-chloro-4-methoxybenzylamino)-5-carboxypyrimidine (prepared in Example 79) 0.100 g and triethylamine 82 µl in tetrahydrofuran 2.0 ml is treated under room temperature with 2,4,6-trichlorobenzoyl chloride 51 µl and then dimethylaminopyridine about 1 mg is added thereto, followed by stirring for 10 minutes. After addition of 2-pyridinemethanol 31 µl, the mixture is stirred for 12 hours. Ethyl acetate and water are added thereto and the organic layer is separated, washed with sodium hydrogen carbonate solution, brine. The organic layer is dried over anhydrous sodium sulfate and in vacuo. The residue is purified with silica gel chromatography (solvent; chloroform:ethyl acetate=5:1–2:1) and recrystallized from ethyl acetate-isopropyl ether to give 2-methylthio-4-(3-chloro-4-methoxybenzylamino)-5-(2-pyridylmethoxycarbonyl)pyrimidine as a colorless needle, 0.5183 g. mp117–118° C.

Example 82

(1) A solution of 2-methylthio-4-(3-chloro-4-methoxybenzylamino)-5-[N-(2-pyridylmethyl)carbamoyl]pyrimidine (prepared in Example 80) 150.0 mg in chloroform 5.0 ml is treated with m-chloroperbenzoic acid (80%) 85.6 mg at 0° C. for 30 minites. Piperazine 0.263 g is added thereto and the mixture is stirred at room temperature overnight. To the reaction mixture is added ethyl acetate and an aqueous saturated sodium hydrogen carbonate solution, and the organic layer is separated. The organic layer is washed with an aqueous saturated sodium hydrogen carbonate solution, water and a saturated brine, dried over anhydrous sodium sulfate, filtered and then concentrated in vacuo. The residue is purified with silica gel chromatography (solvent; ethyl acetate) to give 2-(1-pyperazinyl)-4-(3-chloro-4-methoxybenzylamino)-5-[N-(2-pyridylmethyl)carbamoyl]pyrimidine as a colorless amorphous solid, 128.4 mg.

MS(m/z): 468(M+H)$^+$ (2) The compound prepared in the above (1) is treated with hydrochloric acid in methanol to give a crystalline powder, which is triturated with methanol-isopropyl ether to give 2-(1-pyperazinyl)-4-(3-chloro-4-methoxybenzylamino)-5-[N-(2-pyridylmethyl)carbamoyl]pyrimidine hydrochloride as a colorless crystalline solid, 84.2 mg. mp 252–253° C.(decomposition)

Example 83

2-Methylthio-4-(3-chloro-4-methoxybenzylamino)-5-(2-pyridylmethoxycarbonyl]pyrimidine (prepared in Example 81) 0.1500 g is treated with m-chloroperbenzoic acid (80%) 78.9 mg at 0° C. for 15 minutes. Piperazine 0.2398 g is added thereto. The reaction mixture is treated in the same manner as Example 82-(1). The resulting residue is purified with silica gel chromatography (solvent; ethyl acetate sole—ethyl acetate:methanol=1:1) and recrystallized from ethyl acetate: isopropyl ether (1:1) to give 2-(1-pyperazinyl)-4-(3-chloro-4-methoxybenzylamino)-5-(2-pyridylmethoxycarbonyl)pyrimidine as a colorless powder, 75.1 mg. mp 101–103° C.

Example 84

(1) To a suspension of lithium aluminium hydride 4.15 g in tetrahydrofuran 150 ml is added a solution of 2-methylthio-4-(3-chloro-4-methoxybenzylamino)-5-ethoxycarbonylpyrimidine (prepared in Example 67-(1)) 38.32 g in tetrahydrofuran 100 ml at 5–10° C. under ice cooling over a period of 1 hour. After addition the mixture is stirred for a hour without an ice bath. Water 4.15 ml is added under ice cooling thereto, followed by addition of 3N aqueous sodium hydroxide solution 4.15 ml. To the mixture is added water 4.15 ml three times and the mixture is stirred at room temperature for 1 hour. After treating with magnesium sulfate and filtration, the resulting cake-like substances are washed with terahydrofuran. The filtrate is concentrated in vacuo and triturated with ethyl acetate-isopropyl ether. The resulting crystals are filtered and washed well with isopropyl-ether to give 2-methylthio-4-(3-chloro-4-methoxybenzylamino)-5-hydroxymethylpyrimidine as a pale yellow crystalline powder.

The first product; yield 25.10 g, mp 162–163° C.

The second product; yield 2.32 g, mp 159–160° C.

Further the above cake-like substances are again washed with isopropyl ether, and the filtrate is concentrated in vacuo to give colorless crystals. The crystals are suspended in isopropyl ether, and filtered. The precipitates are washed well isopropyl ether and hexane to give 2-methylthio-4-(3-chloro-4-methoxybenzylamino)-5-hydroxymethylpyrimidine as colorless crystals, 4.26 g. mp 161–162° C.

(2) To a suspension of 2-methylthio-4-(3-chloro-4-methoxybenzylamino)-5-hydroxymethylpyrimidine (prepared in the above (1)) 25.10 g in chloroform 150 ml is a manganese dioxide powder 37.6 g (one and a half of the starting material) and the mixture is vigorously stirred at room temperature for a day. Further the mixture is treated with a manganese dioxide powder 12.6 g (a half of the starting material) and the mixture is stirred for three nights. The insoluble materials are filtered off with Celite and the filtrate is concentrated in vacuo. The residue is suspended in ethyl acetate-isopropyl ether. The precipitate is filtered and washed with isopropyl ether and hexane in order, to give 2-methylthio-4-(3-chloro-4-methoxybenzylamino)-5-formylpyrimidine as colorless crystals, 22.43 g. mp 124–125° C.

Example 85

(1) To a solution of dimethylmethylphosphonate (1.92 g) in tetrahydrofuran (10 ml) is added a 1.6M solution of n-butyl lithium in hexane (8.69 ml) at −78° C. over a period of 10 minutes, and the mixture is stirred at the same temperature for 30 minutes. A solution of 2-methylthio-4-(3-chloro-4-methoxybenzylamino)-5-formylpyrimidine (prepared in Example 84-(2)) 1.00 g in tetrahydrofuran 10 ml is dropped by a syringe at −78° C. to the reaction mixture to give a yellow suspension. The suspension is stirred for 30 minutes. After removal of a dry ice-acetone bath the reaction mixture is stirred for a while and poured into an aqueous saturated sodium hydrogen carbonate solution. The mixture is stirred and extracted with ethyl acetate. The organic layer is separated, washed with water and brine in order, dried over anhydrous sulfate and concentrated in vacuo to give crude 2-methylthio-4-(3-chloro-4-methoxybenzylamino)-5-[(1-hydroxy-2-dimethoxyphosphoryl)ethyl]pyrimidine as a colorless foam, 1.33 g.

(2) A mixture of crude 2-methylthio-4-(3-chloro-4-methoxybenzylamino)-5-[(1-hydroxy-2-dimethoxyphosphoryl)ethyl]pyrimidine (prepared in the above) 1.32 g, manganese dioxide 3.96 g and chloroform 20 ml is vigorously stirred at room temperature overnight. The insoluble manganese dioxide is filtered off and the filtrate is concentrated in vacuo to give a pale yellow foam. The residue is purified with silica gel chromatography (solvent; ethyl acetate sole—ethyl acetate:methanol=10:1). The purified fraction is collected and concentrated in vacuo to give a colorless foam, 1.18 g. The compound is crystallized from ethyl acetate-isopropyl ether to give 2-methylthio-4-(3-chloro-4-methoxybenzylamino)-5-(dimethoxyphosphorylacetyl)pyrimidine as colorless crystals, 1.14 g. mp 104–105° C.

Example 86

(1) To a 1.6M solution of n-butyl lithium in hexane 2.0 ml is dropped a solution of 3-bromopyridine 530 mg in diethyl ether 2 ml by a syringe in a dry ice-acetone bath. A white solid immediately occurs. The reaction mixture is stirred at −78° C. for 10 minutes. To the reaction mixture is added by a syringe a solution of 2-methyltio-4-(3-chloro-4-methoxybenzylamino)-5-formylpyrimidine 208 mg in tetrahydrofuran 2 ml. The mixture is irradiated with ultrasonic wave for several seconds. The reaction mixture is stirred at −78° C. for 5 minutes, and an aqueous saturated sodium hydrogen carbonate solution is added thereto. The mixture is extracted with ethyl acetate and the organic layer is washed with water and brine in order, dried over sodium sulfate and concentrated in vacuo to give a yellow oil. The crude compound is purified with silica gel chromatography (silica gel 20 g, solvent; ethyl acetate sole—ethyl acetate:methanol=20:1) to give 2-methylthio-4-(3-chloro-4-methoxybenzylamino)-5-[(hydroxy)(3-pyridyl)methyl]pyrimidine as a yellow foam, 155 mg.

MS(m/z): 403(M+H)$^+$ (2) A mixture of 2-methylthio-4-(3-chloro-4-methoxybenzylamino)-5-[(hydroxy)(3-pyridyl)methyl]pyrimidine (prepared in the above) 149 mg and manganese dioxide 450 mg in chloroform 3 ml is stirred at room temperature overnight. After removal of insoluble substances by filtration, the filtrate is concentrated in vacuo to give a slightly yellowish solid 140 mg. The solid is suspended in ethyl acetate-isopropyl ether and filtered. The resulting cake-like substances are well washed with hexane to give 2-methylthio-4-(3-chloro-4-methoxybenzylamino)-5-(3-pyridylcarbonyl)pyrimidine as colorless crystals, 127 mg. mp 141–142° C. MS(m/z): 401(M+H)$^+$ Example 87

A solution of 2-methylthio-4-(3-chloro-4-methoxybenzylamino)-5-formylpyrimidine (prepared in Example 84-(2)) 2.057 g in chloroform 20 ml is treated at 0° C. for 30 minutes with m-chloroperbenzoic acid (80%) 1.468 g. L-(S)-Prolinol 0.901 g and then triethylamine 1.33 ml are added thereto. The reaction is carried out at 0° C. for 1 hour. The reaction mixture is elevated to room temperature, diluted with ethyl acetate, washed with an aqueous sodium hydrogen carbonate solution, water and a saturated sodium chloride solution, and dried over anhydrous sodium sulfate. The precipitate is filtered off and the filtrate is concentrated in vacuo to give (S)-2-(2-hydroxymethyl-1-pyrrolidinyl)-4-(3-chloro-4-methoxybenzylamino)-5-formylpyrimidine as a colorless amorphous, 1.9990 g.

MS(m/z): 377(M+H)$^+$

Example 88

A solution of 4-(3-chloro-4-methoxybenzylamino)-5-formyl-2-methylthiopyrimidine 0.5 g in tetrahydrofuran 20 ml is reacted at −78° C. with lithium salt of 1-methylimidazole 0.394 ml in the same manner as Example 86 to give 4-(3-chloro-4-methoxybenzylamino)-5-[(hydroxy)(1-methyl-2-imidazolyl)methyl]-2-methylthiopyrimidine. Thus obtained compound is oxidized at room temperature with manganese dioxide in chloroform and then the oxidized compound is post-treated in the same manner as Example 86 to give 4-(3-chloro-4-methoxybenzylamino)-5-(1-methyl-2-imidazolylcarbonyl-2-methylthiopyrimidine 0.5913 g. mp 158–159° C.

Example 89

A solution of the compound (prepared in Example 88) 124.0 mg in chloroform 3.0 ml is treated under stirring under ice cooling for 15 minutes with 80% m-chloroperbenzoic acid 69.5 mg in the same manner as Example 87. To the mixture are added L-prolinol 60.6 μl and triethylamine 86 μl, and the mixture is stirred under room temperature overnight and post-treated in the same manner as Example 87, to give (S)-4-(3-chloro-4-methoxybenzylamino)-2-(2-hydroxymethyl-1-pyrrolidinyl)5-(1-methyl-2-imidazolylcarbonyl)pyrimidine 121.2 mg.

IR(CHCl$_3$)cm$^{-1}$: 3291, 1591, 1527, 1456, 1417, 1409, 1269,1063, 805 MS(m/z): 457(M+H)$^+$

Example 90

(1) To a 1.6 M solution of n-butyl lithium in hexane 19.3 ml is dropped over a period of 10 minutes a solution of diisopropylamine 3.1 g in tetrahydrofuran 80 ml in a dry ice-acetone bath and the mixture is stirred for 30 minutes. To the mixture is dropped over a period of 2.5 hours a solution of 2,4-dichloropyrimidine 2 g in tetrahydrofuran 70 ml and the mixture is stirred at the same temperature for 1 hour. To the mixture is dropped pyridine-2-aldehyde 2.2 g in tetrahydrofuran 20 ml over a period of 50 minutes, and the mixture is stirred at the same temperature for 1 hour. The reaction mixture is poured into a 10% aqueous citric acid solution and the organic layer is separated, washed with water and brine, dried over sodium sulfate and concentrated in vacuo. The residue is purified with silica gel chromatography (solvent; chloroform:methanol=10:1, hexane:ethyl acetate=3:2, hexane:ethyl acetate=2:1) to give crude 2,4-dichloro-5-[(hydroxy)(2-pyridyl)methyl]pyrimidine 480 mg.

(2) A mixture of the crude compound (prepared in the above (1)) 104 mg, triethylamine 71 mg and 3-chloro-4-methoxybenzylamine 44 mg in toluene 2 ml is stirred for 12 hours at room temperature. The reaction mixture is poured into water and extracted with ethyl acetate. The organic layer is washed with brine, dried over anhydrous sodium sulfate and concentrated in vacuo. The residue is purified with preparative thin-layer chromatography (solvent; chloroform:methanol=22:1) to give 2-chloro-4-(3-chloro-4-methoxybenzylamino)-5-[(hydroxy)(2-pyridyl)methyl]pyrimidine as an amorphous 53 mg. MS(m/z): 391(M+H)$^+$ (3) A mixture of 2-chloro-4-(3-chloro-4-methoxybenzylamino)-5-[(hydroxy)(2-pyridyl)methyl]pyrimidine (prepared in the above (2)) 46 mg, manganese dioxide 230 mg and chloroform 2.3 ml is stirred at room temperature for 3 hours. After removal of insoluble substances by filtration, the filtrate is concentrated in vacuo to give 2-chloro-4-(3-chloro-4-methoxybenzylamino)-5-(2-pyridylcarbonyl)pyrimidine 39 mg. mp 117–119° C. (recrystalization from diethyl ether), MS(m/z): 389(M+H)$^+$

Example 91

A mixture of 2-chloro-4-(3-chloro-4-methoxybenzylamino)-5-(2-pyridylcarbonyl)pyrimidine (prepared in Example 90-(3)) 110 mg, 2-pyridinemethanol 34 mg, 10% sodium hydride 12 mg and tetrahydrofuran 3 ml is stirred at room temperature for 5 minutes. The reaction mixture is poured into water and extracted with ethyl acetate. The organic layer is washed with brine, dried over anhydrous sodium sulfate and concentrated in vacuo. The residue is purified by silica gel chromatography (solvent: ethyl acetate) and triturated with ethyl ether to give 2-(2-pyridylmethoxy)-4-(3-chloro-4-methoxybenzylamino)-5-(2-pyridylcarbonyl) pyrimidine, 104 mg. mp 81–84° C., MS(m/z): 462(M+H)$^+$

Example 92

To a solution of a whole amount of 2-methylsulfinyl-4-(3-chloro-4-methoxybenzylamino)-5-ethoxycarbonylpyrimidine (prepared in Example 68-(1)) in tetrahydrofuran 6 ml is dropped 2N aqueous sodium hydroxide solution 1.32 ml under ice cooling over a 2 minite period and the reaction mixture is stirred at the same temperature for 30 minutes. Further tetrahydrofuran 8 ml and N,N-dimethylacetamide 6 ml are added thereto and the mixture is stirred under ice cooling for 30 minites. Thereto are added water 5 ml and N,N-dimethylacetamide 2 ml and the mixture is stirred under ice cooling for one hour. The reaction mixture is acidified with an aqueous 10% citric acid solution and diluted with water, extracted twice with ethyl acetate. The combined organic layer is washed with water and an aqueous saturated sodium chloride solution, dried over anhydrous sodium sulfate and concentrated in vacuo. The residue is separated by silica gel chromatography (silica gel 20 g, solvent; chloroform:ethyl acetate=5:1→chloroform:isopropanol=30:1) to give 2-hydroxy-4-(3-chloro-4-methoxybenzylamino)-5-ethoxycarbonylpyrimidine as a slightly yellowish crystalline powder, 618 mg. mp 195–197° C.

Example 93

To a solution of 2-methylsulfinyl-4-(3-chloro-4-methoxybenzylamino)-5-ethoxycarbonylpyrimidine (prepared in Example 68-(1)) 200 mg in tetrahydrofuran 4 ml is added under ice cooling potassium tert-butoxide 58 mg, and the reaction mixture is stirred at the same temperature for 1 hour. The reaction mixture is diluted with an aqueous citric acid solution, extracted twice with ethyl acetate. The combined organic layer is washed with water and an aqueous saturated sodium chloride solution, dried over anhydrous sodium sulfate and concentrated in vacuo. The residue is purified by silica gel chromatography (silica gel 10 g, solvent; chloroform sole→chloroform:methanol=20:1) to give the following two fractions.

The first fraction is concentrated in vacuo to give 2-methylthio-4-(3-chloro-4-methoxybenzylamino)-5-ethoxycarbonylpyrimidine as a slightly brawn oil, 33 mg.

The second fraction is concentrated in vacuo to give 2-hydroxy-4-(3-chloro-4-methoxybenzylamino)-5-ethoxycarbonylpyrimidine as a slightly brawn crystalline powder, 132 mg. mp 195–197° C.

Example 94

A mixture of 2-hydroxymethylpyrimidine 1M tetrahydrofuran 0.29 ml, sodium hydride (60%) 11 mg in tetrahydrofuran 1.5 ml is stirred at room temperature for 10 minutes. To the mixture is added 2-methylsulfinyl-4-(3-chloro-4-methoxybenzylamino)-5-ethoxycarbonylpyrimidine (prepared in Example 68-(1)) 100 mg in tetrahydrofuran 2 ml, and the mixture is stirred at room temperature for 30 minutes. To the reaction mixture are added water 2 ml, ethanol 2 m and 2N aqueous sodium hydroxide solution 3 ml, and the mixture is stirred at room temperature overnight.

The reaction mixture is neutralized wish a 10% aqueous citric acid solution, and tetrahydrofuran and ethanol are removed in vacuo. The precipitate is collected, washed with water to give a colorless powder. The powder is dissolved in a mixture of 10% aqueous sodium hydroxide solution and ethyl acetate and the water layer is separated and washed with ethyl acetate. The water layer is neutralized with 10% hydrochloric acid and a 10% aqueous citric acid solution. The resulting precipitate is collected and washed with water to give 2-(2-pyridylmethoxy)-4-(3-chloro-4-methoxybenzylamino)-5-carboxypyrimidine as a colorless powder, 28 mg. mp 204–206° C.

On the other hand, the combined organic layer after removal of the water layer from the above reaction mixture, is washed with 10% aqueous sodium hydroxide solution, water and an aqueous saturated sodium chloride solution, dried over anhydrous sodium sulfate and concentrated in vacuo to give 2-hydroxy-4-(3-chloro-4-methoxybenzylamino)-5-ethoxycarbonylpyrimidine as a colorless crystalline powder, 17 mg. mp 195–197° C., MS(m/z): 338(M+H)$^+$ Example 95

A mixture of 2-hydroxy-4-(3-chloro-4-methoxybenzylamino)-5-ethoxycarbonylpyrimidine (prepared in Example 92) 500 mg, diethylaniline 2 ml and phosphoryl chloride 4 ml is stirred at 80° C. for 30 minutes and then at 100° C. for 5 hours. After cooling, the reaction solution is poured into water in ice and the mixture is stirred at room temperature for 30 minutes. The product is extracted with ethyl acetate and the organic layer is washed with water and an aqueous saturated sodium chloride solution, dried over anhydrous sodium sulfate and concentrated in vacuo. The residue is purified by silica gel chromatography (silica gel 7 g, solvent; chloroform) to give 2-chloro-4-(3-chloro-4-methoxybenzylamino)-5-ethoxycarbonylpyrimidine as a slightly yellow crystalline powder, 375 mg. mp 114–115° C. MS(m/z): 356(M+H)$^+$ Example 96

To a solution of 2-chloro-4-(3-chloro-4-methoxybenzylamino)-5-ethoxycarbonylpyrimidine (prepared in Example 95) 356 mg and 2-hydroxymethylpyridine 109 mg in anhydrous tetrahydrofuran 4.5 ml is added potassium tert-butoxide 112 mg under ice cooling, and the mixture is stirred for 30 minutes. The reaction mixture is diluted with water, extracted twice with ethyl acetate. The combined organic layer is washed with water and an aqueous saturated sodium chloride solution, dried over anhydrous sodium sulfate and concentrated in vacuo. The residue is purified by silica gel chromatography (silica gel 10 g, solvent; chloroform:ethyl acetate=5:1→2:1) and concentrated in vacuo to give 2-(2-pyridylmethoxy)-4-(3-chloro-4-methoxybenzylamino)-5-ethoxycarbonylpyrimidine (the compound prepared in Example 67-(3)) as a colorless caramel, 338 mg, which is crystallized on standing at room temperature overnight. mp 90–92° C.

Example 97

A mixture of 2-chloro-4-(3-chloro-4-methoxybenzylamino)-5-ethoxycarbonylpyrimidine (prepared in Example 95) 285 mg, 5,6,7,8-tetrahydroimidazo[1,2-a]pyrazine 197 mg, triethylamine 0.22 ml and chloroform 3 ml is stirred at room temperature for 2,5 hours, followed by stirring at 60° C. for 2,5 hours. The mixture is diluted with ethyl acetate, and washed with water. The water layer is extracted with ethyl acetate, and the organic layer is washed with water and an aqueous saturated sodium chloride solution, dried over anhydrous sodium sulfate and concentrated in vacuo. The residue is purified with silica gel chromatography (silica gel 10 g, solvent; chloroform:methanol=50:1) and concentrated in vacuo and triturated with isopropyl ether to give 2-(5,6,7,8-tetrahydroimidazo[1,2-a]pyrazin-7-yl)-4-(3-chloro-4-methoxybenzylamino)-5-ethoxycarbonylpyrimidine as a colorless crystalline powder, 290 mg. mp 179–182° C., MS(m/z): 443(M+H)$^+$ Example 98

2-(5,6,7,8-Tetrahydroimidazo[1,2-a]pyrazin-7-yl)-4-(3-chloro-4-methoxybenzylamino)-5-ethoxycarbonylpyrimidine (prepared in Example 97) 290 mg and 2N aqueous sodium hydroxide solution 1.64 ml are suspended in dimethyl sulfoxide-water (5 ml:1 ml) and stirred at room temperature for 1 hour. Tetrahydrofuran 5 ml is added thereto and the mixture is stirred at room temperature for 13 hours. After removal of tetrahydrofuran in vacuo, the residue is diluted with water and neutralized with a 10% aqueous citric acid solution. The precipitate is collected, washed with water, methanol and isopropyl ether to give 2-(5,6,7,8-tetrahydroimidazo[1,2-a]pyrazin-7-yl)-4-(3-chloro-4-methoxybenzylamino)-5-carboxypyrimidine as a colorless crystalline powder, 187 mg. mp 223–226° C.(decomposition), MS(m/z): 413 (M–H)$^-$ Example 99–273

The corresponding starting material is treated in the same manner to prepare compounds illustrated in the following Table 5.

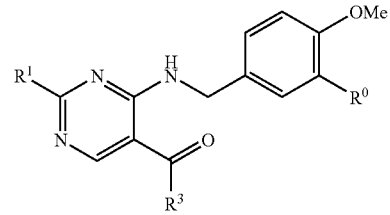

TABLE 5

| Example No. | R$^1$ | R$^0$ | R$^3$ | Physical property etc. |
|---|---|---|---|---|
| 99 | ![tetrahydroisoquinoline-N-] | Cl | ![2,3,4-trimethoxyphenyl] | mp 123–124° C. |

TABLE 5-continued

| Example No. | R¹ | R⁰ | R³ | Physical property etc. |
|---|---|---|---|---|
| 100 | 1H,2H-pyrazol-3(4H)-one fused with N-methyl tetrahydropyridine | Cl | 3,4,5-trimethoxyphenyl (OMe, OMe, OMe) | mp 159–162° C. |
| 101 | 7-methyl-5,6,7,8-tetrahydro-1,7-naphthyridine | Cl | —O—CH₂CH₃ | mp 181.5–183° C. |
| 102 | 7-methyl-5,6,7,8-tetrahydroimidazo[1,2-a]pyrazine | CN | 3,4,5-trimethoxyphenyl (OMe, OMe, OMe) | mp 226–228° C. |
| 103 | 1-methylpiperidin-4-one | Cl | 3,4,5-trimethoxyphenyl (OMe, OMe, OMe) | mp 158–160° C. |
| 104 | 7-methyl-5,6,7,8-tetrahydro-1,7-naphthyridine | Cl | —NH—CH₂CH₂CH₂—OH | mp 158–160° C. |
| 105 | 2-(methoxymethyl)pyridine | Cl | 2,3,4-trimethoxyphenyl (MeO, OMe, OMe) | Foam MS(m/z): 511(M + H)⁺ |
| 106 | 2-methyl-2,3-dihydro-1H-pyrrolo[3,4-b]pyridine | Cl | —NH—CH₂CH₂CH₂—OH | Amorphous MS(m/z): 469(M + H)⁺ |
| 107 | 6-methyl-5,6,7,8-tetrahydro-2,6-naphthyridine | Cl | —O—CH₂CH₃ | mp 122–125° C. |
| 108 | 2-(methoxymethyl)pyridine | Cl | 4-(pyrimidin-2-yl)piperidin-4-yloxy | Amorphous MS(m/z): 562(M + H)⁺ |
| 109 | 2-(methoxymethyl)pyridine | Cl | trans-4-(pyrimidin-2-yloxy)cyclohexyl-methylamino | mp 174–175° C. |
| 110 | 7-methyl-5,6,7,8-tetrahydropyrido[3,4-d]pyrimidine | Cl | —O—CH₂CH₃ | mp 129–133° C. |

TABLE 5-continued
| Example No. | R¹ | R⁰ | R³ | Physical property etc. |
|---|---|---|---|---|
| 111 | 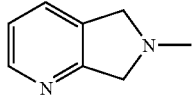 | CN | —O—CH$_2$CH$_3$ | mp 200–203° C. |
| 112 | 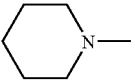 | Cl | 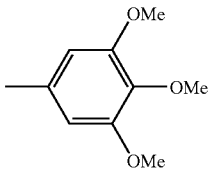 | mp 142–143° C. |
| 113 | 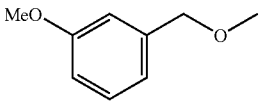 | Cl | 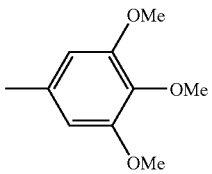 | mp 122–124° C. |
| 114 | 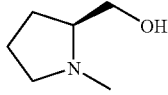 | Cl | 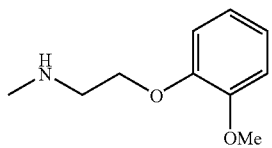 | Caramel MS(m/z): 542(M + H)⁺ |
| 115 | 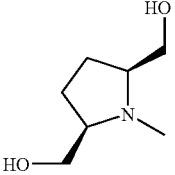 | Cl | 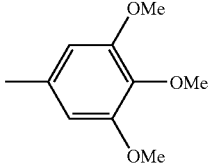 | Amorphous MS(m/z): 573(M + H)⁺ |
| 116 | 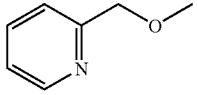 | Cl | 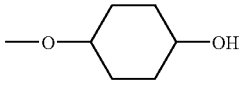 | Amorphous MS(m/z): 499(M + H)⁺ |
| 117 | 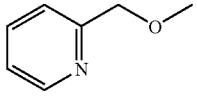 | Cl | 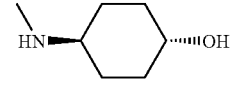 | mp 139–140° C. |
| 118 | 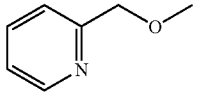 | Cl | 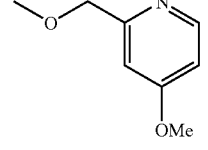 | mp 99–102° C. |
| 119 | 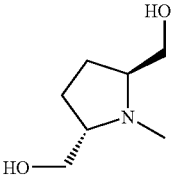 | Cl | 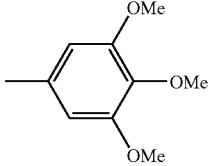 | Amorphous MS(m/z): 573(M + H)⁺ |
| 120 | 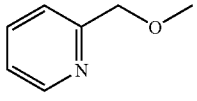 | Cl | 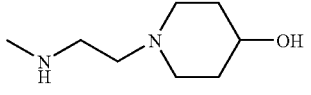 | Amorphous MS(m/z): 527(M + H)⁺ |

TABLE 5-continued
| Example No. | R¹ | R⁰ | R³ | Physical property etc. |
|---|---|---|---|---|
| 121 | 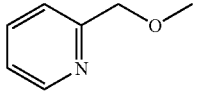 | Cl | 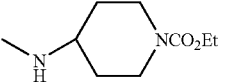 | Amorphous MS(m/z): 555(M + H)⁺ |
| 122 | 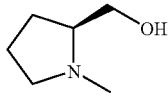 | Cl | 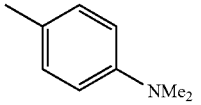 | mp 92–94° C. |
| 123 | 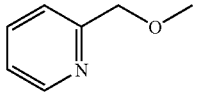 | CN | 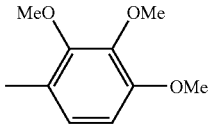 | mp 107–108° C. |
| 124 | 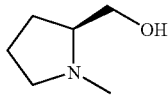 | CN | 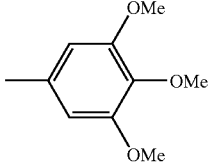 | mp 171° C. |
| 125 | 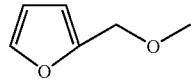 | Cl | 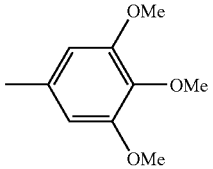 | mp 130–132° C. |
| 126 | 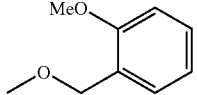 | Cl | 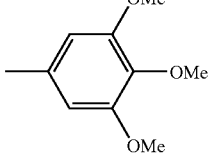 | mp 122–125° C. |
| 127 | 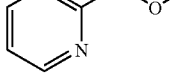 | Cl | 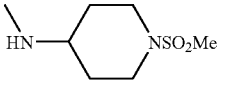 | mp 202–203° C. |
| 128 | 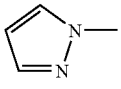 | Cl | 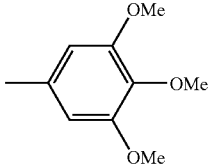 | Amorphous MS(m/z): 510(M + H)⁺ |
| 129 | 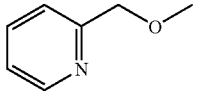 | Cl | 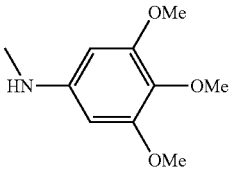 | mp 140–141° C. |
| 130 | 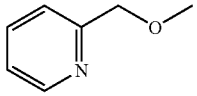 | Cl | 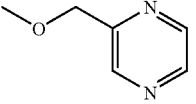 | mp 118–119° C. |

TABLE 5-continued
| Example No. | R¹ | R⁰ | R³ | Physical property etc. |
|---|---|---|---|---|
| 131 | 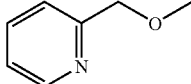 | Cl | 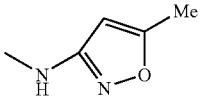 | Amorphous MS(m/z): 481(M + H)⁺ |
| 132 | 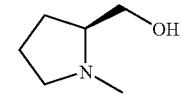 | Cl | 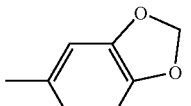 | mp 150–152° C. |
| 133* | 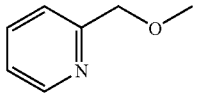 | Cl | 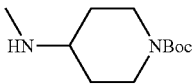 | Amorphous MS(m/z): 583(M + H)⁺ |
| 134 | 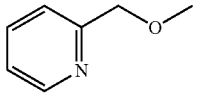 | Cl |  | mp 74–75° C. |
| 135 | 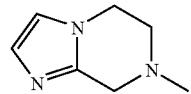 | Cl | 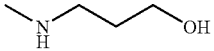 | Amorphous MS(m/z): 472(M + H)⁺ |
| 136 | 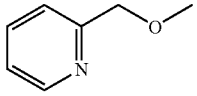 | Cl | 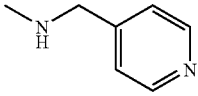 | mp 160–161° C. |
| 137 | 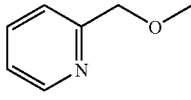 | Cl | 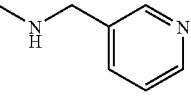 | mp 133–135° C. |
| 138 | 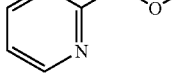 | Cl | 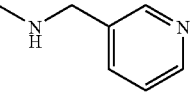 | MsOH salt mp 98–103° C. (decom.) |
| 139 | 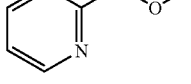 | Cl | 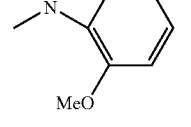 | mp 123–124° C. |
| 140 | 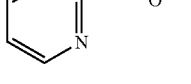 | Cl | 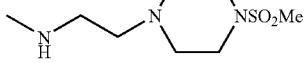 | Amorphous MS(m/z): 590(M + H)⁺ |
| 141 | 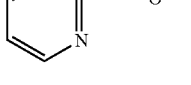 | Cl | 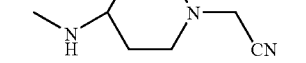 | mp 173° C. |
| 142 | 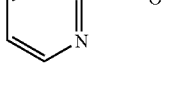 | Cl | 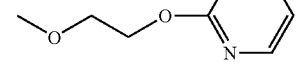 | mp 104–109° C. |
| 143 | 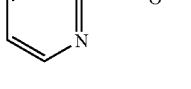 | Cl | 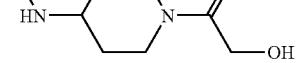 | Amorphous MS(m/z): 541(M + H)⁺ |

TABLE 5-continued
| Example No. | R¹ | R⁰ | R³ | Physical property etc. |
|---|---|---|---|---|
| 144 | 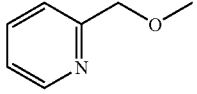 | Cl | 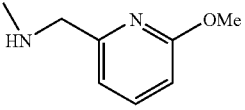 | mp 131–134° C. |
| 145 | 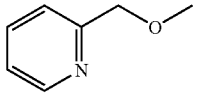 | Cl | 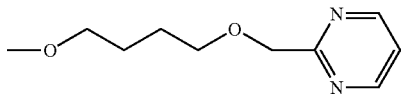 | Caramel MS(m/z): 565(M + H)⁺ |
| 146 | 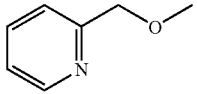 | CN | 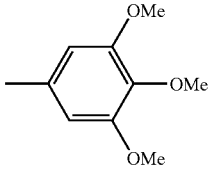 | mp 158–161° C. |
| 147 | 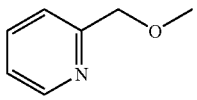 | Cl | 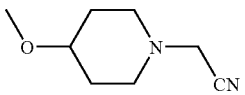 | mp 109–111° C. |
| 148 | 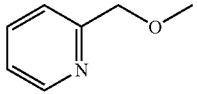 | Cl | 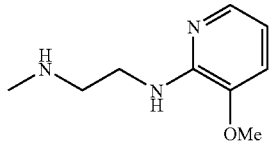 | mp 150–151° C. |
| 149 | 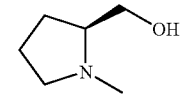 | Cl | 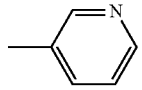 | mp 164–165° C. |
| 150 | 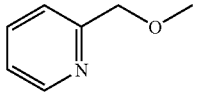 | Cl | 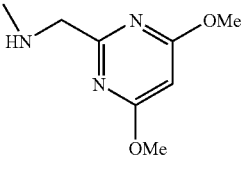 | mp 129–130° C. |
| 151 | 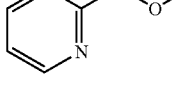 | Cl | 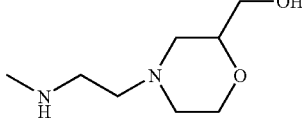 | Amorphous MS(m/z): 543(M + H)⁺ |
| 152 | 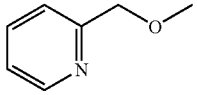 | Cl | 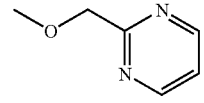 | mp 137–139° C. |
| 153 | 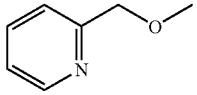 | Cl | 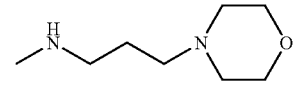 | Amorphous MS(m/z): 527(M + H)⁺ |
| 154 | 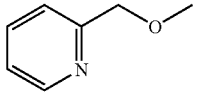 | Cl | 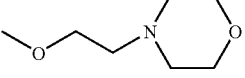 | mp 77–79° C. |

TABLE 5-continued
| Example No. | R¹ | R⁰ | R³ | Physical property etc. |
|---|---|---|---|---|
| 155 |  | Cl |  | mp 166–167° C. |
| 156 |  | Cl | —O—CH$_2$CH$_3$ | mp 129–132° C. |
| 157 |  | Cl |  | Amorphous MS(m/z): 497(M + H)⁺ |
| 158 |  | Cl |  | mp 81–84° C. |
| 159 |  | Cl |  | Oil MS(m/z): 515(M + H)⁺ |
| 160 |  | Cl |  | mp 102–103° C. |
| 161 |  | Cl |  | Amorphous MS(m/z): 513(M + H)⁺ |
| 162 |  | Cl | —O—CH$_2$CH$_3$ | Amorphous MS(m/z): 453(M + H)⁺ |
| 163 |  | Cl |  | mp 219–221° C. |
| 164 |  | Cl |  | mp 166–167° C. |
| 165 |  | Cl |  | mp 192–194° C. |
| 166 |  | Cl |  | Amorphous MS(m/z): 455(M + H)⁺ |

TABLE 5-continued

| Example No. | R¹ | R⁰ | R³ | Physical property etc. |
|---|---|---|---|---|
| 167 | 1-methylpyrrolidine-2,5-diyl-bis(methanol) | CN | 3,4,5-trimethoxyphenyl (methyl-linked) | mp 163–164° C. |
| 168 | (1-methylpyrrolidin-2-yl)methanol | Cl | -NH-CH₂CH₂CH₂-OH (N-methyl) | Amorphous MS(m/z): 450(M + H)⁺ |
| 169 | pyridin-2-ylmethoxy | Cl | 1-(methoxyacetyl)piperidin-4-yl-NH- | mp 60–65° C. |
| 170 | pyridin-2-ylmethoxy | Cl | MeO-CH₂CH₂-OMe | mp 103.5–104° C. |
| 171 | 6-methyl-5,6,7,8-tetrahydropyrido[4,3-d]pyrimidine | Cl | —O—CH₂CH₃ | mp 166–169.5° C. |
| 172 | pyridin-2-ylmethoxy | Cl | N-(2-methoxyethyl)isonicotinamide | Amorphous MS(m/z): 549(M + H)⁺ |
| 173 | pyridin-2-ylmethoxy | F | 3,4,5-trimethoxyphenyl | mp 118–121° C. |
| 174 | pyridin-2-ylmethoxy | Cl | 1-ethyl-1H-pyrazol-5-yl-NH- | Amorphous MS(m/z): 494(M + H)⁺ |
| 175 | pyridin-2-ylmethoxy | Cl | (tetrahydrofuran-2-yl)methyl-NH- | mp 116–117° C. |
| 176 | pyridin-2-ylmethoxy | Cl | pyrimidin-5-yl-NH- | mp 210–212° C. |
| 177 | 2,3-dihydro-1H-inden-2-yl-NH- | Cl | pyridin-2-ylmethyl-NH- | mp 184–184.5° C. |

TABLE 5-continued
| Example No. | R¹ | R⁰ | R³ | Physical property etc. |
|---|---|---|---|---|
| 178 | 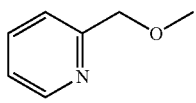 | Cl | 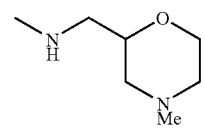 | Amorphous MS(m/z): 513(M + H)⁺ |
| 179 | 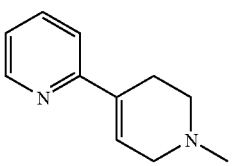 | Cl | —O—CH$_2$CH$_3$ | mp 132–134° C. |
| 180 | 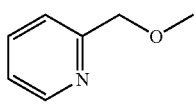 | Cl | 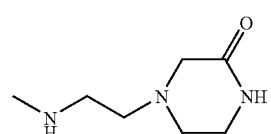 | Amorphous MS(m/z): 526(M + H)⁺ |
| 181 | 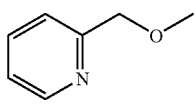 | Cl | 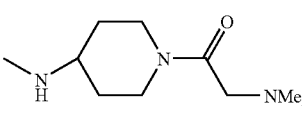 | Amorphous MS(m/z): 568(M + H)⁺ |
| 182 | 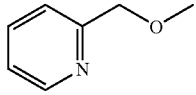 | Cl | 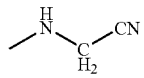 | mp 166–168° C. |
| 183 | 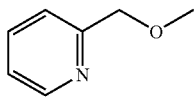 | Cl | 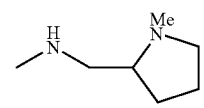 | Amorphous MS(m/z): 497(M + H)⁺ |
| 184 | 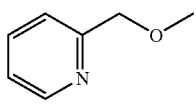 | Cl | 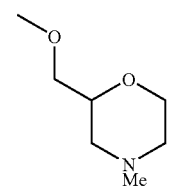 | Amorphous MS(m/z): 514(M + H)⁺ |
| 185 | 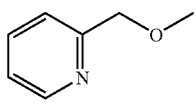 | Cl | 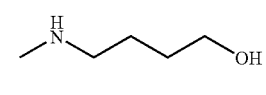 | mp 124–125° C. |
| 186 | 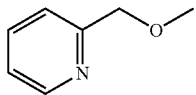 | Cl | 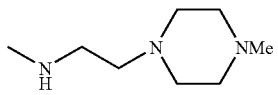 | mp 96–98° C. |
| 187 | 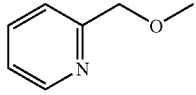 | Cl | 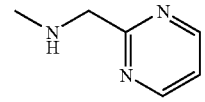 | mp 133–136° C. |
| 188 | 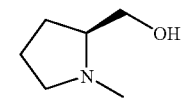 | Cl | 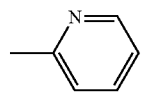 | Amorphous MS(m/z): 454(M + H)⁺ |

TABLE 5-continued

| Example No. | R¹ | R⁰ | R³ | Physical property etc. |
|---|---|---|---|---|
| 189 | MeO−CH₂CH₂−O− (methoxyethoxy) | CN | 2,3,4-trimethoxyphenyl (MeO, OMe, OMe) | mp 82–85° C. |
| 190 | (pyridin-2-yl)methoxy | Cl | −NH−CH₂CH₂CH₂−OH (methylamino propanol) | mp 155–156° C. |
| 191 | 5-methyl-4,5,6,7-tetrahydroisoxazolo[4,5-c]pyridinyl | Cl | −NH−CH₂CH₂CH₂−OH | Amorphous MS(m/z): 473(M + H)⁺ |
| 192 | 7-methyl-3,4,5,6,7,8-hexahydropyrido[3,4-d]pyrimidin-4-one | Cl | −O−CH₂CH₃ | mp 220–223° C. |
| 193 | (pyridin-2-yl)methoxy | Cl | 4-(cyanomethyl)-morpholin-2-yl-methylamino | Amorphous MS(m/z): 538(M + H)⁺ |
| 194 | (pyridin-2-yl)methoxy | Cl | 3-methoxy-2-hydroxypropan-1-ol | mp 146–147° C. |
| 195 | (pyridin-2-yl)methoxy | NO₂ | trans-4-hydroxycyclohexyl-methylamino | Amorphous MS(m/z): 509(M + H)⁺ |
| 196 | (pyridin-2-yl)methoxy | Cl | −NH−CH₂CH₂−OMe | mp 124–126° C. |
| 197 | (pyridin-2-yl)methoxy | Cl | −NH−CH₂CH₂CH₂−OMe | mp 158–159° C. |
| 198 | 7-methyl-3,4,5,6,7,8-hexahydropyrido[3,4-d]pyrimidin-4-one | Cl | −O−CH₂CH₃ | mp 280–282° C. |
| 199 | (2S,5S)-2,5-bis(hydroxymethyl)-1-methylpyrrolidinyl | CN | 3,4,5-trimethoxyphenyl (OMe, OMe, OMe) | mp 176–177° C. |

TABLE 5-continued
| Example No. | R¹ | R⁰ | R³ | Physical property etc. |
|---|---|---|---|---|
| 200 | 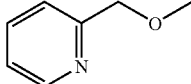 | Cl | 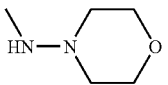 | mp 174–175° C. |
| 201 | 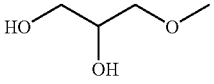 | Cl | 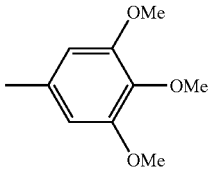 | mp 144–147° C. |
| 202 | 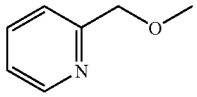 | Cl | 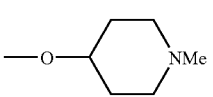 | mp 110–112° C. |
| 203 | 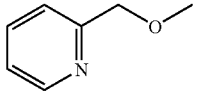 | Cl | 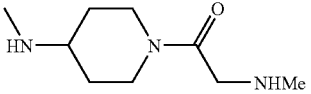 | Amorphous MS(m/z): 554(M + H)⁺ |
| 204 | 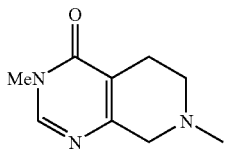 | Cl | —O—CH$_2$CH$_3$ | mp 217–220° C. |
| 205 | 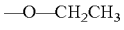 | Cl | 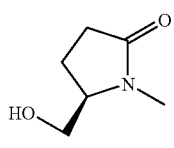 | Amorphous MS(m/z): 504(M + H)⁺ |
| 206 |  | Cl | —O—CH$_2$CH$_3$ | mp 123–124.5° C. |
| 207 | 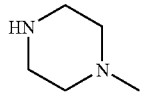 | CN | 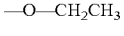 | mp 130–132° C. |
| 208 | 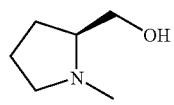 | Cl | —O—CH$_2$CH$_3$ | mp 139–142° C. |
| 209 | 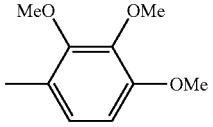 | Cl | —O—CH$_2$CH$_3$ | mp 236–239° C. |
| 210 | 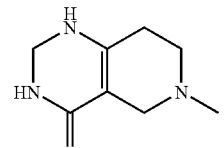 | Cl | 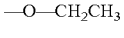 | Amorphous MS(m/z): 497(M + H)⁺ |

TABLE 5-continued

| Example No. | R¹ | R⁰ | R³ | Physical property etc. |
|---|---|---|---|---|
| 211 | HOCH₂-CH(OH)-CH₂-NHMe | Cl | 3,4,5-tri-OMe-phenyl | Powder(HCl) MS(m/z): 533(M + H)⁺ |
| 212 | pyrimidin-2-yl-CH₂-O- | CN | 3,4,5-tri-OMe-phenyl | mp 175–176° C. |
| 213 | MeO— | CH₂OH | 3,4,5-tri-OMe-phenyl | mp 158–161° C. |
| 214 | HOCH₂-CH(NHMe)-CH₂OH | Cl | 3,4,5-tri-OMe-phenyl | Powder(HCl) MS(m/z): 533(M + H)⁺ |
| 215 | 5-methyl-4,5,6,7-tetrahydrothiazolo[5,4-c]pyridine | Cl | MeNH-CH₂CH₂CH₂-OH | Amorphous MS(m/z): 489(M + H)⁺ |
| 216 | pyridin-2-yl-CH₂-N(Me)-CH₂CH₂-OH | Cl | trans-HN(Me)-cyclohexyl-OH | Amorphous MS(m/z): 541(M + H)⁺ |
| 217 | 1-methyl-1H-imidazo[4,5-b]pyridine | Cl | —O—CH₂CH₃ | mp 118–220° C. |
| 218 | pyridin-2-yl-CH₂-O- | NHCHO | 3,4,5-tri-OMe-phenyl | mp 171–173° C. |
| 219 | Ph-CH(NHMe)-CH₂OH | Cl | pyridin-2-yl-CH₂-NHMe | Amorphous MS(m/z): 519(M + H)⁺ |

TABLE 5-continued

| Example No. | R¹ | R⁰ | R³ | Physical property etc. |
|---|---|---|---|---|
| 220 | HO-CH₂CH₂-N(Me)-CH₂CH₂-OH | Cl | -NH-CH₂-(2-pyridyl) | Powder(HCl) MS(m/z): 487(M + H)⁺ |
| 221 | 2-pyridyl-CH₂-OMe | Cl | Et-P(=O)(OMe)(OMe) | Oil MS(m/z): 507(M + H)⁺ |
| 222 | HOCH₂-C(=O)-N(piperazine)N-Me | Cl | trans-HN-cyclohexyl-OH | Amorphous MS(m/z): 535(M + H)⁺ |
| 223 | MeN-piperazine-N- | Cl | MeO-CH₂-(2-pyridyl) | mp 146–147° C. |
| 224 | (S)-1-methyl-2-carbamoyl-pyrrolidin-2-yl | Cl | -NH-CH₂-(2-pyridyl) | Amorphous MS(m/z): 496(M + H)⁺ |
| 225 | HO-CH₂CH₂-N(Me)(Me) | Cl | -NH-CH₂-(2-pyridyl) | mp 217–219° C. |
| 226 | MeN-piperazine-N- | Cl | -NH-C₆H₄-OMe | mp 162–163° C. |
| 227 | 2-pyridyl-CH₂-OMe | Cl | -NH-CH₂-CH(OH)-CH₂-OH | mp 153–155° C. |
| 228 | 2-pyridyl-CH₂-OMe | Cl | -NMe₂ | mp 129–130° C. |
| 229 | HO-CH₂-(4-methylmorpholin-2-yl) | CN | 3,4,5-triOMe-C₆H₂- | mp 186–188° C. |
| 230 | 2-pyridyl-CH₂-OMe | Cl | HN(Me)-Me | mp 164–165° C. |
| 231 | 4-MeO-C₆H₄-CH₂-O- | Cl | 3,4,5-triOMe-C₆H₂- | mp 114–119° C. |

TABLE 5-continued

| Example No. | R¹ | R⁰ | R³ | Physical property etc. |
|---|---|---|---|---|
| 232 | 4-(2-pyridyl)-4-hydroxy-1-methylpiperidine | Cl | —O—CH₂CH₃ | Amorphous MS(m/z): 498(M + H)⁺ |
| 233 | 2-(methoxymethyl)pyridine | Cl | HN(Me)CH(CH₂OH)₂ | mp 175–176° C. |
| 234 | 2-(methoxymethyl)pyridine | CH₂O—Ac | 3,4,5-trimethoxybenzyl | Amorphous MS(m/z): 589(M + H)⁺ |
| 235 | AcOCH₂C(O)-(4-methylpiperazin-1-yl) | Cl | trans-4-(methylamino)cyclohexanol | Amorphous MS(m/z): 575(M + H)⁺ |
| 236 | 2-(methoxymethyl)pyridine | Cl | MeHN(CH₂)₃NMe₂ | mp 84–86° C. |
| 237 | EtO— | CN | 3,4,5-trimethoxybenzyl | mp 165° C. |
| 238 | N-methyl-N-benzyl | Cl | N-methyl-(2-pyridylmethyl)amino | mp 132–134° C. |
| 239 | N-benzyl | Cl | N-methyl-(2-pyridylmethyl)amino | mp 195–197° C. |
| 240 | 3-chloro-4-methoxybenzyl[N-(5-ethoxycarbonyl-1-methyl-2-oxo-1,2-dihydropyrimidin-4-yl)]amine | Cl | —O—CH₂CH₃ | mp 105–108° C. |
| 241 | 6,7-dimethoxy-2-methyl-1,2,3,4-tetrahydroisoquinoline | Cl | N-methyl-(2-pyridylmethyl)amino | Powder(HCl) MS(m/z): 575(M + H)⁺ |
| 242 | 1,4-dimethylpiperazine | Cl | trans-4-(methylamino)cyclohexanol | mp 158–159° C. |

TABLE 5-continued
| Example No. | R¹ | R⁰ | R³ | Physical property etc. |
|---|---|---|---|---|
| 243 | 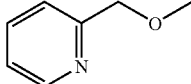 | Cl | 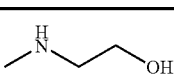 | mp 162–163° C. |
| 244 | 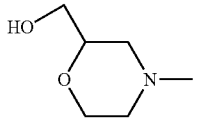 | CN | 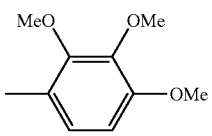 | mp 104–108° C. |
| 245 | 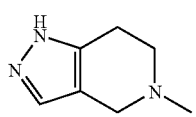 | Cl | 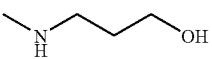 | mp 113–117° C. |
| 246 | 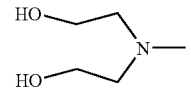 | CN | 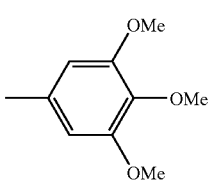 | mp 165–167° C. |
| 247 | 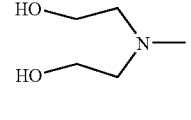 | CN | 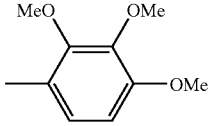 | mp 108–110° C. |
| 248 | 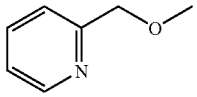 | Cl | 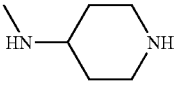 | mp 119–121° C. |
| 249 | 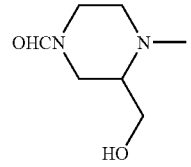 | Cl |  | Amorphous |
| 250 | 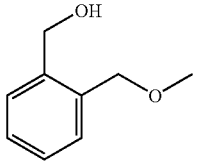 | Cl | 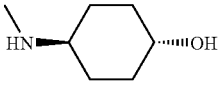 | mp 115–120° C. |
| 251 | 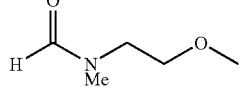 | Cl | 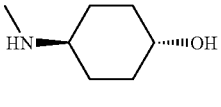 | Amorphous MS(m/z): 492(M + H)⁺ |
| 252 | 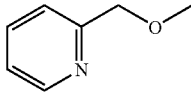 | Cl | 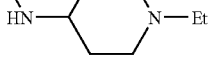 | mp 124–126° C. |
| 253 | 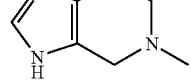 | Cl |  | Amorphous MS(m/z): 472(M + H)⁺ |

TABLE 5-continued
| Example No. | R¹ | R⁰ | R³ | Physical property etc. |
|---|---|---|---|---|
| 254 | 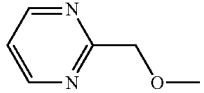 | Cl |  | mp 135–137° C. |
| 255 | 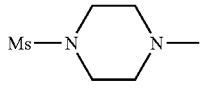 | Cl |  | mp 158–161° C. |
| 256 | 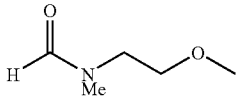 | Cl |  | Amorphous MS(m/z): 520(M + H)⁺ |
| 257 | 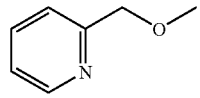 | Cl | 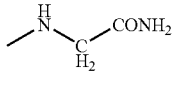 | mp 187–188° C. |
| 258 | 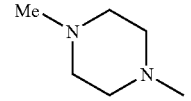 | Cl | —O—CH₂CH₃ | mp 136.5–137° C. |
| 259 | 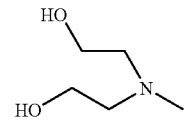 | Cl |  | mp 149–151° C. |
| 260 | 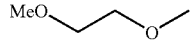 | Cl |  | mp 170–172° C. |
| 261 | 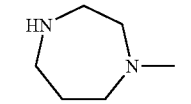 | Cl | 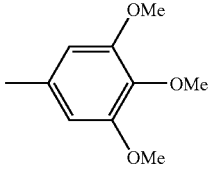 | Powder(HCl) MS(m/z): 542(M + H)⁺ |
| 262 | 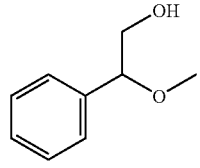 | Cl |  | Amorphous MS(m/z): 527(M + H)⁺ |
| 263 | 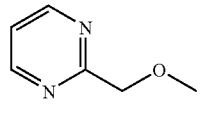 | CN | 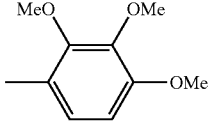 | mp 164–166° C. |
| 264 | 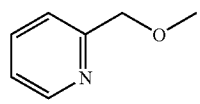 | SOMe | 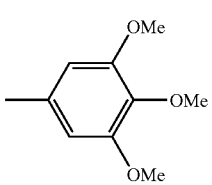 | Amorphous MS(m/z): 579(M + H)⁺ |

TABLE 5-continued
| Example No. | R¹ | R⁰ | R³ | Physical property etc. |
|---|---|---|---|---|
| 265 | 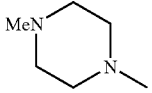 | Cl | 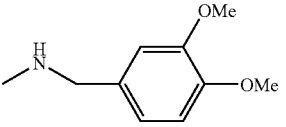 | Amorphous MS(m/z): 541(M + H)⁺ |
| 266 | Me₂N | Cl |  | mp 87–89° C. |
| 267 | Me₂N | Cl | 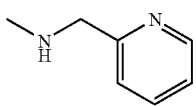 | mp 162–163° C. |
| 268 | 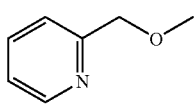 | NO₂ | 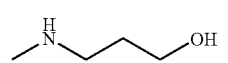 | mp 173–176° C. |
| 269 | 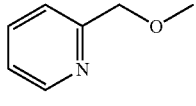 | Cl | 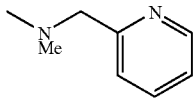 | Amorphous MS(m/z): 505(M + H)⁺ |
| 270 | 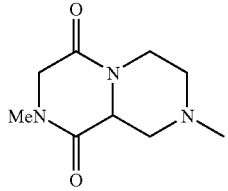 | Cl | —O—CH₂CH₃ | mp 165–167° C. |
| 271 | 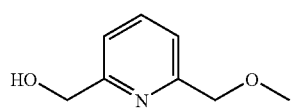 | Cl |  | Oil MS(m/z): 528(M + H)⁺ |
| 272 | 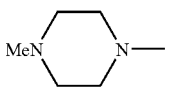 | Cl | 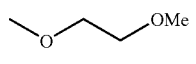 | mp 112.5–113° C. |
| 273 | MeO— | CN | 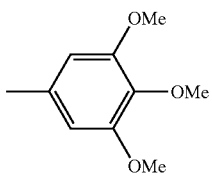 | mp 174–175° C. |
*Boc = t-butoxycarbonyl Example 74–286

The corresponding starting material is treated in the same manner to prepare compounds illustrated in the following Table 6.

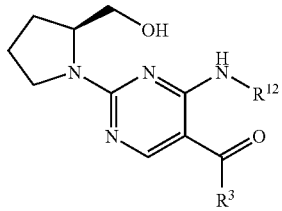

TABLE 6

| Example No. | R[12] | R[3] | Physical property etc. |
|---|---|---|---|
| 274 | Et-phenyl(OMe)(OMe) | —OEt | mp 92.5–93.5° C. |
| 275 | Et-phenyl(OMe)(OMe) | —NH-CH2-pyrimidine | Powder MS(m/z): 480(M + H)+ |
| 276 | Me-phenyl(OMe)(Cl) | —NH-CH2-pyrimidine | Powder MS(m/z): 470(M + H)+ |
| 277 | Et-pyrimidine | —NH-CH2-phenyl(OMe)(Cl) | Powder MS(m/z): 484(M + H)+ |
| 278 | Et-benzofuran | —NH-CH2-pyrimidine | Powder MS(m/z): 460(M + H)+ |
| 279 | Et-phenyl(Cl) | —NH-CH2-pyrimidine | Powder MS(m/z): 454(M + H)+ |
| 280 | Et-phenyl(Cl)(OiPr) | —NH-CH2-pyrimidine | Amorphous MS(m/z): 512(M + H)+ |
| 281 | Et-pyrazine-Me | —NH-CH2-pyrimidine | Powder MS(m/z): 436(M + H)+ |

TABLE 6-continued

| Example No. | R¹² | R³ | Physical property etc. |
|---|---|---|---|
| 282 | ethyl-phenyl with OMe and NH₂ substituents | -NH-CH₂-pyrimidin-2-yl (N-methyl) | Powder MS(m/z): 465(M + H)⁺ |
| 283 | ethyl-phenyl with OH and NH₂ substituents | -NH-CH₂-pyrimidin-2-yl (N-methyl) | Powder MS(m/z): 451(M + H)⁺ |
| 284 | 5-ethyl-2,3-dihydrobenzofuran | -NH-CH₂-pyrimidin-2-yl (N-methyl) | Powder MS(m/z): 462(M + H)⁺ |
| 285 | 5-ethyl-benzoxazol-2(3H)-one | -NH-CH₂-pyrimidin-2-yl (N-methyl) | Powder MS(m/z): 475(M + H)⁺ |
| 286 | 5-ethyl-1H-benzimidazole | -NH-CH₂-pyrimidin-2-yl (N-methyl) | Powder MS(m/z): 460(M + H)⁺ |

Example 287

(1) 98% Formic acid 1.44 ml is dropped to acetic anhydride 2.86 ml under ice cooling and the mixture is stirred at 60° C. for 1 hour. After ice cooling the reaction mixture is diluted with tetrahydrofuran 15 ml, and thereto is added under ice cooling a solution of 3-chloro-4-methoxybenzylamine 2.00 g in tetrahydrofuran 16 ml. The reaction mixture is stirred at room temperature for 1 hour.

Tetrahydrofuran is removed in vacuo at 35° C. and the residue is made alkaline with an aqueous saturated sodium hydrogen carbonate solution. The mixture is extracted twice with ethyl acetate and the combined organic layer is washed with water and an aqueous saturated sodium hydrogen carbonate solution, dried over sodium sulfate and concentrated in vacuo. The residue is separated with silica gel chromatography (silica gel 30 g, solvent; chloroform:ethyl acetate=1:1) and concentrated in vacuo to give a compound as a colorless crystalline powder 2.05 g. mp 82–85° C., MS(m/z): 200(M+H)⁺

(2) To a solution of the compound (prepared in the above (1)) 2.02 g in tetrahydrofuran 38 ml is dropped 10M boron-methyl sulfide complex(BH₃.Me₂S) 4.55 ml over a period of 5 minutes under ice cooling. The mixture is stirred on an ice bath for 30 minutes and then refluxed for 2 hours. After ice cooling methanol 10 ml is dropped thereto and the reaction mixture is stirred at room temperature for 30 minutes. To the mixture is added 4.9N hydrochloric acid in methanol 20 ml and the mixture is refluxed for 30 minutes. The solvent is removed in vacuo and the residue is diluted with water and the mixture is washed with isopropyl ether-ethyl acetate (1:1) and the organic layer is extracted with 10% hydrochloric acid. The combined water layer is washed with isopropyl ether-ethyl acetate (2:1), is made alkaline with a 10% aqueous sodium hydroxide solution and the solution is extracted twice with ethyl acetate. The combined organic layer is washed with a 10% aqueous sodium hydroxide solution, water, and an aqueous saturated sodium chloride solution, dried over sodium sulfate and concentrated in vacuo to give N-methyl-(3-chloro-4-methoxy)benzylamine 1.62 g as a pale brown oil. MS(m/z): 186(M+H)⁺

(3) A mixture of 2,4-dichloro-5-(3,4,5-trimethoxyphenylcarbonyl)pyrimidine 120 mg, the compound (prepared in the above (2)) 68 mg, triethylamine 37 mg and anhydrous dimethylformamide 3 ml is stirred for 1 hour under ice cooling and is diluted with a 10% aqueous citric acid solution. The solution is extracted twice with ethyl acetate and the combined organic layer is washed with water and an aqueous saturated sodium chloride solution, dried over sodium sulfate and concentrated in vacuo. The residue is separated with silica gel chromatography (silica gel 10 g, solvent; chloroform:ethyl acetate=100:1→50:1).

The first fraction is concentrated in vacuo and crystallized from a mixture of diisopropyl ether and hexane to give 4-chloro-5-(3,4,5-trimethoxyphenylcarbonyl)-2-[N-methyl-N-(3-chloro-4-metoxybenzyl)amino]pyrimidine as a colorless crystalline powder 30 mg. mp 103–104° C., MS(m/z): 492(M+H)⁺

The second fraction is concentrated in vacuo to give 2-chloro-5-(3,4,5-trimethoxyphenylcarbonyl)-4-[N-methyl-N-(3-chloro-4-methoxybenzyl)amino]pyrimidine as a colorless foam 109 mg. MS(m/z): 492(M+H)⁺

(4) 2-Chloro-5-(3,4,5-trimethoxyphenylcarbonyl)-4-[N-methyl-N-(3-chloro-4-methoxybenzyl)amino]pyrimidine (prepared in the above (3)) is treated in the same manner as Example 1-(4) to give 2-(2-pyridylmethoxy)-5-(3,4,5-trimethoxyphenylcarbonyl)-4-[N-methyl-N-(3-chloro-4-metoxybenzyl)amino]pyrimidine as a colorless crystalline powder 74 mg. mp 154–157° C., MS(m/z): 565(M+H)⁺

Examples 288–290

The corresponding starting compounds are treated in the same manner as Example 287 to give the compounds listed in the following Table 7.

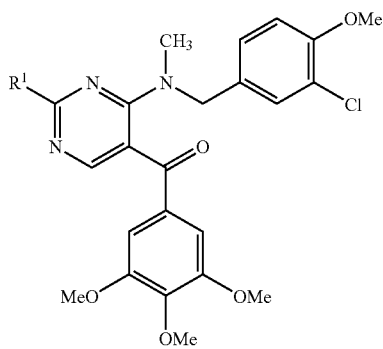

TABLE 7

| Example No. | R[1] | Physical property etc. |
|---|---|---|
| 288 | ![pyrrolidine-CH2OH, N-Me] | Powder(HCl) MS(m/z): 557(M + H)[+] |
| 289 | MeN-piperazine-N— | Powder(HCl) MS(m/z): 556(M + H)[+] |
| 290 | HO-CH2CH2-N(-CH2CH2-OH)— | Powder(HCl) MS(m/z): 561(M + H)[+] |

Example 291

The following compounds are prepared in the same manner from the corresponding starting compounds.

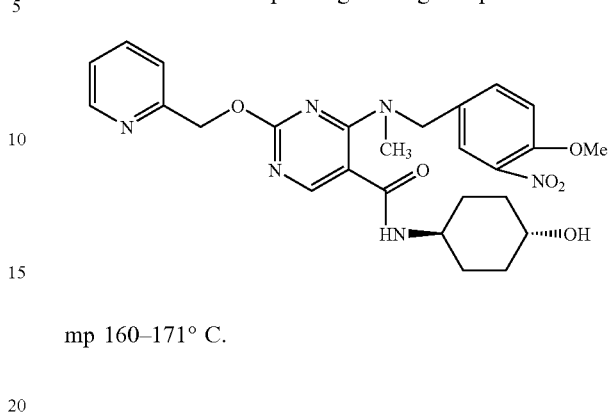

mp 160–171° C.

Examples 292–296

The following compounds are prepared in the same manner from the corresponding starting compounds.

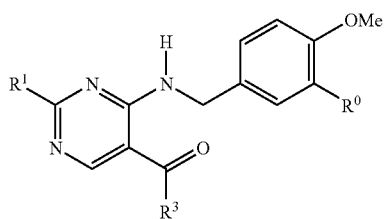

TABLE 8

| Example No. | R[1] | R[0] | R[3] | Physical property etc. |
|---|---|---|---|---|
| 292 | 2-pyridyl-CH2-O- | Cl | HN-piperidine-NCHO (N-Me linker) | mp 181–183° C. |
| 293 | 2-pyridyl-CH2-O- | Cl | -O-CH2CH2-O-CH2CH2-OMe | Oil MS(m/z): 503(M + H)[+] |
| 294 | 2-pyridyl-CH2-O- | Cl | MeNH-CH2CH2-O-(2-OMe-phenyl) | mp 143–145° C. |
| 295 | 2-pyridyl-CH2-O- | Cl | MeO-CH2-piperidine-NMe | mp 111–113° C. |

TABLE 8-continued

| Example No. | R¹ | R⁰ | R³ | Physical property etc. |
|---|---|---|---|---|
| 296 | (pyrrolidine-CH₂OH, N-Me) | CN | —OEt | Amorphous MS(m/z): 412(M + H)⁺ |

Example 297

(1) To a solution of diisopropylamine (0.78 g) in tetrahydrofuran (40 ml) is dropped a 1.6M solution of n-butyl lithium in hexane (4.82 ml) over a period of 3 minutes under cooling on dry ice in acetone bath. The mixture is stirred on the same bath for 30 minutes and thereto is added 2,6-dichloropyrazine 0.50 g in tetrahydrofuran 5 ml at the same temperature over a period of 15 minutes. After stirring for 1 hour, the mixture is poured into dry ice and stirred at room temperature for 1 hour. The mixture is diluted with 10% hydrochloric acid to be adjusted pH about 2 and extracted with ethyl acetate. The combined organic layer is extracted with an aqueous saturated sodium hydrogen carbonate solution. The water extract is washed with ethyl acetate and made acid with a 10% aqueous hydrochloric acid solution and extracted with ethyl acetate. The combined organic layer is washed with water and an aqueous saturated sodium chloride solution, dried over sodium sulfate and concentrated in vacuo. The residue is triturated with chloroform-hexane (1:1) to give 2-carboxy-3,5-dichloropyrazine 234 mg as a slightly brownish crystalline powder. mp 139–141° C., MS(m/z): 191(M−H)⁻

(2) A mixture of 2-carboxy-3,5-dichloropyrazine (prepared in the above (1)) 226 mg, sodium hydrogen carbonate 118 mg, methyl iodide 0.5 ml and dimethylformamide 1.8 ml is stirred at room temperature for 14 hours. The mixture is diluted with a 10% aqueous citric acid solution and extracted with ethyl acetate. The combined organic layer is washed with water and an aqueous saturated sodium chloride solution, dried over sodium sulfate and concentrated in vacuo to give 2-methoxycarbonyl-3,5-dichloropyrazine as a pale brown crystalline powder 245 mg. mp 60–63° C., MS(m/z): 206(M⁺)

(3) A mixture of 2-methoxycarboxy-3,5-dichloropyrazine (prepared in the above (2)) 234 mg, 3-chloro-4-methoxybenzylamine 204 mg, triethylamine 0.17 ml and anhydrous toluene 3 ml is stirred for 7 hours at room temperature. The reaction mixture is diluted with a 10% aqueous citric acid solution and the solution is extracted with ethyl acetate. The extract is washed with water and an aqueous saturated sodium chloride solution, dried over sodium sulfate and concentrated in vacuo. The residue is purified and separated with silica gel chromatography (silica gel 5 mg, solvent; hexane:chloroform=1:1) and then the desired fraction is concentrated in vacuo to give 2-methoxycarbonyl-3-(3-chloro-4-methoxybenzylamino)-5-chloropyrazine as a pale yellow crystalline powder 102 mg.
mp 149–151° C., MS(m/z): 342(M+H)⁺

Example 298

To a mixture of 2-methoxycarbonyl-3-(3-chloro-4-methoxybenzylamino)-5-chloropyrazine (prepared in the above Example 297(3)) 71 mg and 2-hydroxymethylpyridine 25 mg in tetrahydrofuran 3 ml is added potassium tert-butoxide 26 mg under ice cooling. The mixture is stirred for 30 minutes at the same temperature and diluted a 10% aqueous citric acid solution. The solution is extracted with ethyl acetate and the extract is washed with water and an aqueous saturated sodium chloride solution, dried over sodium sulfate and concentrated in vacuo. The residue is purified and separated with silica gel chromatography (silica gel 5 g, solvent; chloroform:ethyl acetate=3:1) and crystallized from isopropyl ether to give 2-methoxycarbonyl-3-(3-chloro-4-methoxybenzylamino)-5-(2-pyridylmethoxy)pyrazine as a pale yellow crystalline powder, 25 mg. mp 132–133° C., MS(m/z): 415(M+H)⁺

Example 299

A mixture of 2-methoxycarbonyl-3-(3-chloro-4-methoxybenzylamino)-5-chloropyrazine (prepared in 297-(3)) 150 mg, 2-hydroxymethylpyrrolidine 88.6 mg and triethylamine 0.12 ml in tetrahydrofuran 5 ml is stirred for 4 hours at room temperature and heated at 50° C. for 2 hours. Then 2-hydroxymethylpyrrolidine 44.3 mg is added thereto and the mixture is heated at 50° C. for 1 hour. After cooling, water is added thereto and the solution is extracted with ethyl acetate. The extract is washed with water and brine, dried over anhydrous sodium sulfate and concentrated in vacuo. The resulting yellowish oil is purified with silica gel frash column chromatography (solvent; chloroform:hexane=1:1) to give (S)-2-methoxycarbonyl-3-(3-chloro-4-methoxybenzylamino)-5-(2-hydroxymethyl-1-pyrrolidinyl)pyrazine as a pale yellowish powder, 123 mg.
MS (m/z): 407 (M+H)⁺

Example 300

A compound listed in Table 9 is prepared from a corresponding starting compound in the same manner as described above.

TABLE 9

| Example No. | R¹ | R³ | Physical property etc. |
|---|---|---|---|
| 300 | 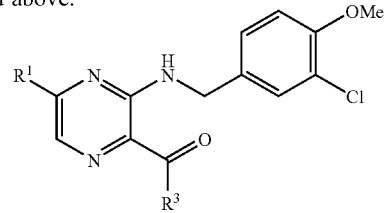 | —OMe | Amorphous MS(m/z): 429(M + H)⁺ |

Example 301

(1) A mixture of 5-benzoyloxy-2-(3,4,5-trimethoxybenzoyl)benzoic acid 50 mg, 14.8M aqueous ammonia 50 μl, 1-ethyl-3-(3-dimethylaminopropyl)carbodiimido hydrochloride 68 mg and 1-hydroxybenzotriazole 15.9 mg is dissolved under ice cooling in N,N-dimethylformamide 2 ml and the mixture is stirred overnight at room temperature. To the reaction mixture is added water. The mixture is extracted with ethyl acetate and the extract is washed with water and dried, followed by removal of the solvent. The residue is purified with silica gel chromatography (solvent: chloroform:ethyl acetate=1:1) and left to be crystallized. The crystals are triturated with diisopropyl ether-ethyl acetate to give 6-benzyloxy-3-hydroxy-3-(3,4,5-trimethoxyphenyl)-2,3-dihydroisoindol-1-one 46.7 mg.

mp 187–189° C.

(2) To a suspension of the compound (prepared in the above (1)) 1.065 g in dioxane 20 ml is added at room temperature 2M aqueous sodium hydroxide solution 10.11 ml. Thereto is added at room temperature a 9% aqueous sodium hypobromite (NaOBr) solution 12.4 ml, and the mixture is stirred overnight. To the mixture is added an aqueous sodium hydrogen carbonate solution and the mixture is extracted with ethyl acetate. The extract is washed, dried and the solvent is removed. The residue is purified with silica gel chromatography (solvent: hexane:ethyl acetate=1:1) and crystallized from diisopropyl ether-ethyl acetate to give 5-benzyloxy-2-(3,4,5-trimethoxybenzoyl)aniline 0.662 mg. mp 79–80° C.

(3) To a solution of the compound (prepared in the above (2)) 1 g in methanol 30 ml is added palladium-carbon 100 mg, and the mixture is stirred for 3 hours under hydrogen atmosphere (1 atm.). After removal of catalyst the filtrate is concentrated to give 5-hydroxy-2-(3,4,5-trimethoxybenzoyl)aniline 847 mg as an amorphous.

(4) To a mixture of the compound (prepared in the above (3)) 300 mg and 2-pycolyl chloride hydrochloride 78 mg in N,N-dimethylformamide 5 ml is added under ice cooling 60% sodium hydride 103 mg, and the mixture is stirred for 1 hour. The reaction mixture is poured into water, extracted with ethyl acetate and the extract is washed with water, dried and removed the solvent. The residue is purified with silica gel chromatography (solvent: chloroform:methanol=80:1) to give 5-(2-pyridylmethoxy)-2-(3,4,5-trimethoxybenzoyl) aniline as an amorphous 238 mg.

(5) A mixture of the compound (prepared in the above (4)) 100 mg, 3-chloro-4-methoxybenzyl chloride 53 mg, 60% sodium hydride and tetrahydrofuran 4 ml is refluxed under heating for 24 hours. After reaction mixture is cooled and poured into water, the solution is extracted with ethyl acetate. The extract is washed with brine, dried over aquous sodium sulfate and concentrated in vacuo. The residue is purified with silica gel chromatography (solvent; chloroform:ethyl acetate=20:1) and triturated with methanol to give 1-(2-pyridylmethoxy)-3-(3-chloro-4-methoxybenzylamino)-4-(3,4,5-trimethoxybenzoyl)benzene 21 mg as yellow crystals. mp 142–144° C., MS(m/z): 549(M+H)$^+$ Example 302

(1) A mixture of 4-chloro-2-nitrobenzoic acid methyl ester 100 mg, prolinol 235 mg and 1-methyl-2-pyrrolidinone 3 ml is stirred at 100° C. for 3 hours. After cooling to room temperature, ethyl acetate and water are added to the mixture. The organic layer is washed with water (twice) and brine, and dried over sodium sulfate. After removal of the sodium sulfate, the filtrate is concentrated in vacuo, and the residue is purified with preparative thin-layer chromatography (two plates, solvent; hexane:ethyl acetate=1:1) to give 4-(2-hydroxymethyl-1-pyrrolidinyl)-2-nitrobenzoic acid methyl ester 20 mg as a yellow oil.

MS(m/z): 281(M+H)$^+$ (2) A mixture of 4-chloro-2-nitrobenzoic acid methyl ester 100 mg, prolinol 56 mg, diisopropylethylamine 90 mg and 1-methyl-2-pyrrolidinone 3 ml is stirred at 100° C. for 13 hours. Ethyl acetate and water are added to the mixture, and the organic layer is washed with water (twice) and brine, and dried over sodium sulfate. After removal of the sodium sulfate, the filtrate is concentrated in vacuo, and the residue is purified with column chromatography (silica gel 100 g, solvent; hexane:ethyl acetate=4:1→2:1→1:1→100% ethyl acetate) to give 4-(2-hydroxymethyl-1-pyrrolidinyl)-2-nitrobenzoic acid methyl ester 1.298 g as a pale yellow viscosity oil. MS(m/z): 285(M+H)$^+$ (3) A mixture of the compound (prepared in the above (1) or (2)) 260 mg, 10% palladium-carbon 25 mg and ethanol 10 ml is subjected to hydrogenation under hydrogen atmosphere at room temperature for 7 hours. After removal of catalyst by filtration the filtrate is concentrated in vacuo. The residue is purified with column chromatography (NH-silica gel 25 g, solvent; hexane:ethyl acetate=1:1→ethyl acetate) to give 4-(2-hydroxymethyl-1-pyrrolidinyl)-2-aminobenzoic acid methyl ester as pale yellow crystals, 185 mg. mp 113–115° C., MS(m/z): 251(M+H)$^+$ (4) To a mixture of the compound (prepared in the above (3)) 50 mg, 3-chloro-4-methoxybenzaldehyde 61 mg, acetic acid 21 mg and 1,2-dichloroethane 2 ml is added at room temperature triacetoxy sodium hydrogen borate 113 mg. The mixture is stirred for 1 hour and thereto are added ethyl acetate and an aqueous saturated sodium hydrogen carbonate solution. The organic layer is washed with water and brine, and dried over sodium sulfate. After removal of sodium sulfate by filtration the filtrate is concentrated in vacuo. The residue is purified with preparative thin-layer chromatography (2 sheets, solvent; hexane:ethyl acetate=1:1) to give a red amorphous compound. The compound is further purified with preparative thin-layer chromatography (2 sheets, solvent; chloroform:methanol=20:1) to give 4-(2-hydroxymethyl-1-pyrrolidinyl)-2-(3-chloro-4-methoxybenzylamino)benzoic acid methyl ester as a red powder, 75 mg. MS(m/z): 405(M+H)$^+$ (5) A mixture of the compound (prepared in the above (4)) 459 mg, a 10% aqueous sodium hydroxide solution 2 ml and dimethyl sulfoxide 4 ml are stirred at room temperature for 4 days. To the mixture are added ethyl acetate and water and then the mixture is neutralized with 10% hydrochloric acid. The organic layer is washed with water (three times) and brine, and dried over sodium sulfate. After removal of sodium sulfate by filtration the filtrate is concentrated in vacuo. The residue is purified with chromatography (silica gel 40 g, solvent; chloroform:methanol=100:3, and then silica gel 40 g, solvent; hexane:ethyl acetate=1:1) and the desired fraction is triturated with diethyl ether to give 4-(2-hydroxymethyl-1-pyrrolidinyl)-2-(3-chloro-4-methoxybenzylamino)benzoic acid 255 mg. mp 132–134° C. (decomposition), MS(m/z): 391(M+H)$^+$ (6) A mixture of the compound (prepared in the above (5)) 80 mg, 1-ethyl-3-(3-dimethylaminopropyl)carbodiimido.hydrochloride 59 mg, 1-hydroxybenzotriazole 42 mg, 2-aminomethylpyrimidine 34 mg and dimethylformamide 3 ml are stirred at room temperature for a day. To the mixture are added 2-aminomethylpirimidine 68 mg and the mixture is stirred at room temperature for 3 days. Ethyl acetate and an aqueous saturated sodium hydrogen carbonate solution are added thereto and the organic layer is washed with water (five times) and brine, and dried over sodium sulfate. After removal of sodium sulfate by filtration the filtrate is concentrated in vacuo. The residue is purified with preparative thin-layer chromatography (2 sheets, solvent; ethyl acetate)

to give pale yellow crystals and the crystals are triturated with a mixture of ethyl acetate and diethyl ether to give 4-(2-hydroxymethyl-1-pyrrolidinyl)-2-(3-chloro-4-methoxybenzylamino)-N-(2-pyrimidinylmethyl)benzamide 37 mg. mp 102–107° C., MS(m/z): 482(M+H)⁺

Example 303

A compound listed in the following Table 10 is prepared by treating a corresponding starting compound in the same manner as Example 302.

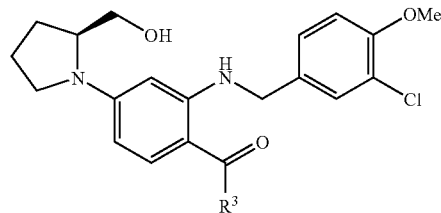

TABLE 10

| Example No. | R³ | Physical property etc. |
|---|---|---|
| 303 | ![structure] | Amorphous MS(m/z): 503(M + H⁺) |

Example 304

(1) A mixture of 4,6-dihydroxynicotinic acid ethyl ester 7.80 g and phosphoryl chloride 48 ml is stirred for 8 hours at 100° C. The excess phosphoryl chloride is removed in vacuo and the residue is poured into ice water. The mixture is made basic with sodium carbonate and extracted with ethyl acetate. The extract is washed with water and brine, and dried over sodium sulfate. After removal of the sodium sulfate, the filtrate is concentrated in vacuo, and the residue is purified with column chromatography (silica gel 10 g, solvent; hexane:ethyl acetate=10:1) to give 4, 6-dichloronicotinic acid ethyl ester 8.50 g as colorless crystals. mp 32–32.5° C., MS(m/z): 220(M+H)⁺

(2) A mixture of the compound (prepared in the above (1)) 1.02 g, 3-chloro-4-methoxybenzylamine 1.02 g, triethylamine 823 mg and acetonitrile 20 ml is stirred at room temperature for 1.5 days and then refluxed for 3 hours. After removal of the solvent the residue is diluted with a mixture of ethyl acetate and an aqueous sodium hydrogen carbonate solution. The organic layer is washed with an aqueous saturated sodium hydrogen carbonate solution, water and brine, and dried over sodium sulfate. After removal of the sodium sulfate, the filtrate is concentrated in vacuo, and the residue is purified with column chromatography (silica gel 25 g, solvent; hexane:ethyl acetate=4:1) and triturated with cooled diethyl ether to give 2-chloro-4-(3-chloro-4-methoxybenzylamino)nicotinic acid ethyl ester 1.17 g as colorless crystals. mp 115.5–117.5° C., MS(m/z): 355(M+H)⁺

(3) A mixture of the compound (prepared in the above (2)) 500 mg, a 10% aqueous sodium hydroxide solution 5 ml and dimethyl sulfoxide 20 ml is stirred for 15 hours at room temperature. The mixture is acidified (pH about 5) with a 10% aqueous hydrochloric acid solution at 0° C. After dropping water thereto, the mixture is stirred at room temperature for 1 hour and the precipitate is filtered and the filtrate is washed with water and concentrated in vacuo to give 2-chloro-4-(3-chloro-4-methoxybenzylamino)nicotinic acid 441 mg. mp 228–230° C., MS(m/z): 325(M–H)⁻

(4) A mixture of the compound (prepared in the above (3)) 100 mg, 1-ethyl-3-(3-dimethylaminopropyl)carbodiimide. hydrochloride 88 mg, 1-hydroxybenzotriazole 62 mg, 2-aminomethylpyrimidine 50 mg and dimethylformamide 3 ml is stirred for 1 day at room temperature. To the mixture are added ethyl acetate and an aqueous sodium hydrogen carbonate solution, and the organic layer is washed with water (four times) and brine and dried over sodium sulfate. After removal of the sodium sulfate, the filtrate is concentrated in vacuo, and the residue is triturated with diethyl ether to give 3-(2-pyrimidinylmethylaminocarbonyl)-6-chloro-4-(3-chloro-4-methoxybenzylamino)pyridine 76 mg as colorless crystals. mp 133.5–136.5° C., MS(m/z): 418 (M+H)⁺

(5) A mixture of the compound (prepared in the above (4)) 66 mg, prolinol 80 mg and 1-methyl-2-pyrrolidinone 3 ml is stirred at 200° C. for 4.5 hours. After the mixture is cooled to room temperature, ethyl acetate and an aqueous sodium hydrogen carbonate solution are added to the mixture and the organic layer is washed with water (five times) and brine, and dried over sodium sulfate. After removal of the sodium sulfate, the filtrate is concentrated in vacuo, and the residue is purified with preparative thin-layer chromatography (3 sheets, solvent; chloroform:methanol=10:1) to give 3-(2-pyrimidinylmethylaminocarbonyl)-6-(2-hydroxymethyl-1-pyrrolidinyl)-4-(3-chloro-4-methoxybenzylamino)pyridine 43 mg as a pale brown powder. MS(m/z): 483(M+H)⁺

Examples 305–306

Each compound listed in the following Table 11 is prepared by treating a corresponding starting compound in the same manner as Example 304.

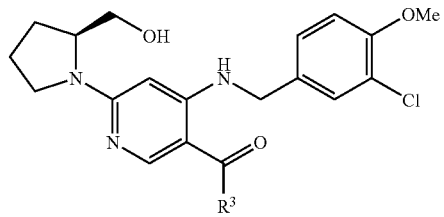

TABLE 11

| Example No. | R³ | Physical property etc. |
|---|---|---|
| 305 | ![structure] | Amorphous MS(m/z): 504(M + H)⁺ |
| 306 | ![structure] | mp: 179.5–182.5° C. |

Example 307

(1) To a solution of diisopropylamine 3.76 g in tetrahydrofuran 25 ml is dropped at −78° C. n-butyllithium (23.2 ml). The mixture is stirred at 0° C. for 10 minutes and thereto is added 2,6-dichloropyridine 5.0 g in tetrahydrofuran 25 ml at −78° C. over a period of 20 minutes. The mixture is stirred at −78° C. for 3 hours. The reaction mixture is poured into powdered dry ice and is left at room temperature overnight. After removal of the solvent the residue is dissolved in a mixture of ethyl acetate and a 10% aqueous sodium hydroxide solution, and the water layer is separated and made acid with concentrated hydrochloric acid. The resulting colorless precipitate is filtered and washed with cold water to give 2,6-dichloronicotinic acid 4.50 g. mp 148–150° C., MS(ESI): 190(M−H)−

(2) A mixture of the compound (prepared in the above (1)) 500 mg, 3-chloro-4-methoxybenzylamine 638 mg, potassium carbonate 817 mg, copper bromide 313 mg and 1-methyl-2-pyrrolidinone 10 ml is stirred at 120° C. for 2.5 hours. After cooling to room temperature thereto are added ethyl acetate and 1N hydrochloric acid. The organic layer is separated, washed with water (twice) and brine, and dried over sodium sulfate. After removal of sodium sulfate, the filtrate is concentrated in vacuo, and the residue is purified with column chromatography (silica gel 30 g, solvent; chloroform→chloroform:methanol=70:1) to give 2-(3-chloro-4-methoxybenzylamino)-6-chloronicotinic acid as colorless crystals, 471 mg. mp 184–185.5° C., MS(m/z): 325(M−H)−

(3) A mixture of the compound (prepared in the above (2)) 200 mg and ethanol 10 ml is saturated with hydrogen chloride gas at 0° C. and is refluxed for 14 hours. The mixture is again saturated with hydrogen chloride and is refluxed for 4 hours. After removal of the solvent the residue is diluted with a mixture of ethyl acetate and an aqueous sodium hydrogen carbonate solution, and the organic layer is purified with column chromatography (silica gel 25 g, solvent; hexane→hexane:ethyl acetate 20:1, then silica gel 25 g, solvent; chloroform:hexane=1:1) to give 2-(3-chloro-4-methoxybenzylamino)-6-chloronicotinic acid ethyl ester as colorless crystals, 84 mg. mp 108–112.5° C., MS(m/z): 355(M+H)+

(4) A mixture of the compound (prepared in the above (2)) 150 mg, 1-ethyl-3-(3-dimethylaminopropyl)carbodiimide. hydrochloride 132 mg, 1-hydroxybenzotriazole 93 mg, 2-aminomethylpyrimidine 75 mg and dimethylformamide 3 ml is stirred for 16 hours at room temperature. To the mixture are added ethyl acetate and an aqueous sodium hydrogen carbonate solution, and the organic layer is washed with water (three times) and brine and dried over sodium sulfate. After removal of the sodium sulfate, the filtrate is concentrated in vacuo, and the residue is purified with column chromatography (silica gel 25 g, solvent; chloroform:methanol=50:1) to give 2-(3-chloro-4-methoxybenzylamino)-6-chloro-3-(2-pyrimidinylmethyl aminocarbonyl)pyridine as a pale yellow amorphous, 179 mg. MS(m/z): 418(M+H)+

(5) A mixture of the compound (prepared in the above (4)) 159 mg, prolinol 192 mg and 1-methyl-2-pyrrolidinone 3 ml is stirred at 200° C. for 2 hours. After the mixture is cooled to room temperature, ethyl acetate and water are added to the mixture and the organic layer is separated, washed with water (five times) and brine, and dried over sodium sulfate. After removal of the sodium sulfate by filtration, the filtrate is concentrated in vacuo, and the residue is purified with preparative thin-layer chromatography (2 sheets, solvent; chloroform:methanol=10:1, and then 2 sheets, solvent; ethyl acetate) to give 2-(3-chloro-4-methoxybenzylamino)-6-(2-hydroxymethyl-1-pyrrolidinyl)-3-(2-pyrimidinylmethylaminocarbonyl)pyridine as a colorless amorphous 119 mg. MS(m/z): 483(M+H)+

Examples 308–309

Each compound listed in the following Table 12 is prepared by treating a corresponding starting compound in the same manner as Example 307.

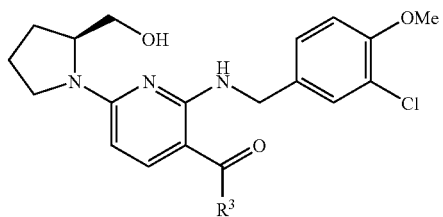

TABLE 12

| Example No. | R³ | Physical property etc. |
|---|---|---|
| 308 | ![structure] | Amorphous MS(m/z): 504(M + H)+ |
| 309 | ![structure] | Amorphous MS(m/z): 489(M + H)+ |

Example 310

(1) To a mixture of 3-ketoglutaric acid dimethyl ester 15.0 g, triethylamine 9.6 g and acetonitrile 300 ml is portionwise added 4-acetylaminobenzensulfonylazide 20.7 g at 0° C. The mixture is stirred at room temperature for 30 minutes. After removal of the precipitate by filtration the filtrate is concentrated in vacuo. The residue is diluted with a mixture of hexane and diethyl ether (1:1). The insoluble materials are removed by filtration and the filtrate is concentrated in vacuo. The residue is purified with column chromatography (silica gel 225 g, solvent; hexane:ethyl acetate=5:1→3:1) to give 2-diazo-3-ketoglutaric acid dimethyl ester as a pale yellow oil, 16.03 g.

(2) A mixture of the compound (prepared in the above (1)) 17.08 g, triphenylphosphine 22.4 g and diethyl ether 170 ml is stirred at room temperature for 15 hours. The solvent is removed in vacuo and the resulting pale yellow solid-like residue is diluted with a mixture of acetic acid 170 ml and water 17 ml, and the mixture is refluxed for 9.5 hours. The solvent is removed in vacuo and the residue is mixed with silica gel 50 g in a mixture of chloroform and methanol (1:1) and purified with column chromatography (silica gel 400 g, solvent; chloroform:methanol=50:1→5:1) and triturated with diethyl ether to give 4,6-dihydroxypyridazine carboxylic acid methyl ester as pale yellow crystals, 8.065 g. mp 216–218° C. (decomposition)

(3) A mixture of the compound (prepared in the above (2)) 8.06 g and phosphoryl chloride 80 ml is stirred at 100° C. for 4 hours. After removal of the excess phosphoryl chloride, the residue is poured into ice-water and extracted with ethyl acetate, washed with water (twice) and brine, and dried over sodium sulfate. After removal of the sodium sulfate, the filtrate is concentrated in vacuo, and the residue is purified with column chromatography (silica gel 200 g, solvent; hexane:ethyl acetate=4:1) to give 3-methoxycarbonyl-4,6-dichloropyridazine as colorless crystals 7.44 g. mp 57–59.5° C.

(4) A mixture of the compound (prepared in the above (3)) 150 g and 3-chloro-4-methoxybenzylamine 1.37 g, triethylamine 1.1 g and toluene 30 ml is stirred at room temperature for 6 hours. Further 3-chloro-4-methoxybenzylamine 250 mg is added thereto and the mixture is stirred at room temperature for additional 17 hours. Ethyl acetate and an aqueous sodium hydrogen carbonate solution are added thereto and the organic layer is washed with water and brine, and dried over sodium sulfate. After removal of the sodium sulfate, the filtrate is concentrated in vacuo, and the residue is triturated with diethyl ether to give a colorless solid 2.34 g. mp159–161° C. The solid is purified with silica gel chromatography (silica gel 100 g, solvent; chloroform) to give 3-methoxycarbonyl-6-chloro-4-(3-chloro-4-methoxybenzylamino)pyridazine 1.89 g. mp 162–163° C., MS(m/z): 342(M+H)+

(5) A mixture of the compound (prepared in the above (4)) 800 mg, prolinol 273 mg, triethylamine 496 mg and 1-methyl-2-pyrrolidinone 10 ml is stirred at 50° C. for 4 hours, and then at 80° C. for 8 hours. After the mixture is cooled to room temperature, ethyl acetate and an aqueous sodium hydrogen carbonate solution are added to the mixture, and the organic layer is washed with water and brine, and dried over sodium sulfate. After removal of the sodium sulfate, the filtrate is concentrated in vacuo, and the residue is purified with column chromatography (silica gel 50 g, solvent; ethyl acetate→ethyl acetate:ethanol=5:1) to give 3-methoxycarbonyl-6-(2-hydroxymethyl-1-pyrrolidinyl)-4-(3-chloro-4-methoxybenzylamino)pyridazine as a colorless powder. MS(m/z): 407(M+H)+

(6) A mixture of the compound (prepared in the above (4)) 500 mg, a 10% aqueous sodium hydroxide solution 5 ml and dimethyl sulfoxide 10 ml is stirred at room temperature for 4 hours. The mixture is acidified (pH about 5) at 0° C. with conc. hydrochloric acid. Water is added thereto and the precipitate is collected, washed with water and dried in vacuo to give 6-chloro-4-(3-chloro-4-methoxybenzylamino)pyridazine-3-carboxylic acid 487 mg. mp 155–157° C.(decomposition) MS(m/z): 326(M–H)−

(7) A mixture of the compound (prepared in the above (6)) 100 mg, 1-ethyl-3-(3-dimethylaminopropyl)carbodiimide. hydrochloride 88 mg, 1-hydroxybenzotriazole 62 mg, 2-aminomethylpyrimidine 50 mg and dimethylformamide 3 ml is stirred for 4 days at room temperature. To the mixture are added ethyl acetate and an aqueous sodium hydrogen carbonate solution, and the organic layer is washed with water (four times) and brine and dried over sodium sulfate. After removal of sodium sulfate, the filtrate is concentrated in vacuo, and the residue is triturated with diethyl ether to give 3-(2-pyrimidinylmethylaminocarbonyl)-6-chloro-4-(3-chloro-4-methoxybenzylamino)pyridazine as a colorless solid, 105 mg. mp 165–180° C.(decomposition), MS(m/z): 418(M+H)+

(8) A mixture of the compound (prepared in the above (7)) 94 mg, prolinol 113 mg and 1-methyl-2-pyrrolidinone 3 ml is stirred at 120° C. for 6 hours. After the mixture is cooled to room temperature, ethyl acetate and water are added to the mixture, and the organic layer is washed with water (five times) and brine, and dried over sodium sulfate. After removal of the sodium sulfate, the filtrate is concentrated in vacuo, and the residue is purified with preparative thin-layer chromatography (3 sheets, solvent; chloroform:methanol=10:1) and triturated with diethyl ether to give 3-(2-pyrimidinylmethylaminocarbonyl)-6-(2-hydroxymethyl-1-pyrrolidinyl-4-(3-chloro-4-methoxybenzylamino)pyridazine as colorless crystals, 51 mg.

mp 168–170.5° C., MS(m/z): 484(M+H)+

Examples 311–312

Each compound listed in the following Table 13 is prepared by treating a corresponding starting compound in the same manner as Example 310.

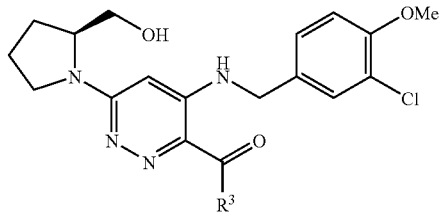

TABLE 13

| Example No. | R³ | Physical property etc. |
|---|---|---|
| 311 | HN–⌬–⌬OH (trans-4-aminocyclohexanol) | mp: 205–207° C. MS (m/z): 490 (M + H)+ |
| 312 | CH₃–NH–CH₂CH₂–N(morpholine) | Amorphous MS (m/z): 505 (M + H)+ |

Example 313

(1) A mixture of 3-methylthio-5-hydroxy-6-ethoxycarbonyl-1,2,4-triazine (see Chem. Ber., 2179–2184, 97 (1964)) 546 mg and thionyl chloride 10 ml is stirred at 60–70° C. for 5 hours. The mixture is concentrated in vacuo, and to the residue is added 3-chloro-4-methoxybenzylamine hydrochloride 634 mg and dimethylformamide 20 ml, and further triethylamine 770 mg in dimethylformamide 20 ml. After stirring for 3 hours at room temperature, the mixture is poured into water and extracted with ethyl acetate. The combined ethyl acetate layer is washed with water and brine, concentrated in vacuo. The residue is purified with silica gel chromatography (solvent; chloroform:methanol=50:1) to give 3-methylthio-5-(3-chloro-4-methoxybenzylamino)-6-ethoxycarbonyl-1,2,4-triazine as a pale yellow solid, 769 mg.

mp 101–105° C. MS(m/z): 369(M+H)+

(2) A solution of m-chloroperbenzoic acid (70–75%) 900 mg in chloroform 10 ml is dropped at 5° C. to the compound (prepared in the above (1)) 1.261 g in chloroform 20 ml. Three hours later thereto are added a solution of L-prolinol 380 mg and triethylamine 400 mg in chloroform 10 ml. The mixture is stirred for 5 hours at room temperature. The chloroform layer is washed with water, an aqueous sodium hydrogen carbonate solution, water and brine in order, and dried in vacuo. The residue is purified with neutral silica gel chromatography (solvent; chloroform:methanol=20:1) to give 3-(2-hydroxymethyl-1-pyrrolidinyl)-5-(3-chloro-4-methoxybenzylamino)-6-ethoxycarbonyl-1,2,4-triazine as a white powder 719 mg.

MS (m/z): 422 (M+H)$^+$ (3) A solution of sodium hydroxide 250 mg in water 4 ml is added to the compound (prepare in the above (2)) 700 mg in dimethyl sulfoxide 20 ml at 10° C. Then the mixture is stirred for 3 hours at room temperature. The mixture is neutralized (pH 6–7) with water 50 ml and a 10% aqueous citric acid solution and extracted with ethyl acetate. The ethyl acetate layer is washed with an aqueous sodium chloride solution, dried and distilled to give crude 3-(2-hydroxymethyl-1-pyrrolidinyl)-5-(3-chloro-4-methoxybenzylamino)-6-carboxy-1,2,4-triazine as a pale brown amorphous, 416 mg. MS(m/z): 392(M+H)$^+$ (4) To a mixture of the compound (prepared in the above (3)) 150 mg, 1-hydroxybenzotriazole 57 mg and 2-aminomethylpyrimidine 65 mg in dimethylformamide is added at 100° C. 1-ethyl-3-(3-dimethylaminopropyl)carbodiimide. hydrochloride 81 mg. The mixture is stirred at room temperature for 20 hours and poured into water containing sodium hydrogen carbonate and extracted with ethyl acetate. The combined ethyl acetate layer is washed with water (four times) and brine, dried over sodium sulfate and concentrated in vacuo. The residue is purified with silica gel chromatography (solvent; chloroform:methanol=50:1→20:1) and the main fraction is crystallized from a mixture of ethyl acetate and hexane to give 3-(2-hydroxymethyl-1-pyrrolidinyl)-5-(3-chloro-4-methoxybenzylamino)-6-(2-pyrimidinylmethylaminocarbonyl)-1,2,4-triazine 85 mg. mp 170–173° C. MS(m/z): 485(M+H)$^+$ Examples 314–315

Each compound listed in the following Table 14 is prepared by treating a corresponding starting compound in the same manner as Example 313.

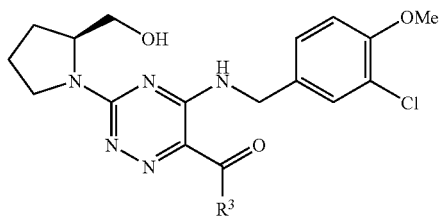

TABLE 14

| Example No. | R$^3$ | Physical property etc. |
|---|---|---|
| 314 | 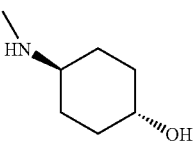 | Powder<br>MS (m/z): 491 (M + H)$^+$ |
| 315 | 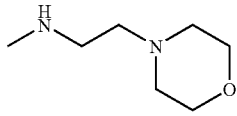 | Powder<br>MS (m/z): 506 (M + H)$^+$ |

Example 316

(1) 3,5-Dibromopyridine 2.37 g is dissolved in methylene chloride 25 ml and thereto is added m-chloroperbenzoic acid 2.96 g at room temperature under stirring. After stirring for 5 hours at room temperature, additional m-chloroperbenzoic acid 246 mg is added thereto and the mixture is stirred. After 15 hours the solvent is removed in vacuo and the residue is purified by silica gel chromatography (solvent; n-hexane: ethyl acetate=1:1) to give 3,5-dibromopyridine N-oxide as colorless crystals, 2.26 g. mp 140–142° C.

(2) A mixture of 3,5-dibromopyridine N-oxide (prepared in the above (1)) 2.26 g, trimethylsilylcyanide 1.06 g and dimethylcarbamic acid chloride 1.15 g in methylene chloride 25 ml is refluxed under heating for 1 day. To the mixture are added trimethylsilylcyanide 443 mg and dimethylcarbamic acid chloride 480 mg, and the mixture is refluxed under heating for 20 hours. An aqueous sodium hydrogen carbonate solution is added to the reaction mixture cooled, and the mixture is extracted with methylene chloride. The combined extract is washed, dried and the solvent is removed in vacuo. The residue is purified by silica gel chromatography (solvent; n-hexane:ethyl acetate=1:1) to give 2-cyano-3,5-dibromopyridine 1.38 g. mp 109–112° C.

(3) 2-Cyano-3,5-dibromopyridine (prepared in the above (2)) 3.27 g is added to a mixture of acetic acid 14 ml, sulfuric acid 14 ml and water 14 ml, and the mixture is refluxed at 140° C. for 4 hours. The reaction mixture is cooled and water is added thereto. The resulting precipitate is filtered and washed with water. The precipitate is dissolved in ether, washed and dried. The solvent is removed in vacuo and crystallized from a mixture of ether and hexane to give 3,5-dibromopyridine-2-carboxylic acid. mp 170–171° C.

(4) In N-methylpyrrolidone 6 ml are suspended 3,5-dibromopyridine-2-carboxylic acid (prepared in the above (3)) 561 mg, 3-chloro-4-methoxybenzylamine 1.71 g, copper bromide 315 mg and potassium carbonate 912 mg, and the suspension is stirred at 120° C. for 17 hours. To the reaction mixture are added 1N hydrochloric acid and ethyl acetate, and the precipitate is filtered and washed with water and aqueous ammonia. On the other hand the filtrate, ethyl acetate layer is also washed with water and aqueous ammonia. The precipitate previously obtained and the ethyl acetate layer are combined and the solvent is removed in vacuo. The residue is purified by NH-silica gel chromatography (solvent; chloroform:methanol=50:1–20:1) to give 5-bromo-3-(3-chloro-4-methoxybenzylamino)pyridine-2-caboxlic acid as a pale yellow powder, 300 mg.

(5) In N,N-dimethylformamide 3 ml are suspended 5-bromo-3-(3-chloro-4-methoxybenzylamino)pyridine-2-caboxlic acid (prepared in the above (4)) 102 mg, diethylcyanophosphonate 67 mg, triethylamine 83 mg and 2-aminomethylpyrimidine 90 mg, and the suspension is stirred at room temperature for 7 hours. To the reaction mixture is added diethylcyanophosphonate 67 mg, and the mixture is stirred at room temperature for 4 hours. Further diethylcyanophosphonate 67 mg and 2-aminomethylpyrimidine 90 mg are added thereto and the mixture is stirred at room temperature for 15 hours. An aqueous sodium hydrogen carbonate solution is added to the reaction mixture, and the mixture is extracted with ethyl acetate. The organic layer is washed and dried, and then the solvent is removed in vacuo. The residue is purified by silica gel chromatography (solvent; chloroform) and crystallized from ether to give 5-bromo-3-(3-chloro-4-methoxybenzylamino)-2-(2-pyrimidinylmethylaminocarbonyl)pyridine as pale yellow crystals 55 mg. mp 179–183° C. (decomposition)

(6) In diglyme 2 ml are suspended 5-bromo-3-(3-chloro-4-methoxybenzylamino)-2-(2-pyrimidinylmethylaminocarbonyl)pyridine (prepared in the above (5)) 20 mg, trisdibenzylidene acetone palladium (0) 22 mg, 2,2'- bisdiphenylphosphino-1,1'-binaphthyl 4 mg, cesium carbonate 43 mg and L-prolinol 88 mg, and the mixture is stirred at 120° C. for 5 hours. An aqueous saturated sodium hydrogen carbonate solution is added to the reaction mixture cooled, and the mixture is extracted with ethyl acetate. The combined organic layer is washed, dried and the solvent is removed in vacuo. The residue is purified by silica gel preparative thin-layer chromatography (developing solution; ethyl acetate) to give (S)-(3-chloro-4-methoxybenzylamino)-5-(2-hydroxymethyl-1-pyrrolidinyl)-2-(2-pyrimidinylmethylaminocarbonyl)pyridine as a pale brown powder 5.2 mg. MS(m/z): 483(M+H)+

Example 317

The following compound is obtained from 5-bromo-3-(3-chloro-4-methoxybenzylamino)pyridine-2-caboxlic acid in the same manner as Example 316 (5) and (6).

3-(3-Chloro-4-methoxybenzylamino)-5-(2-hydroxymethyl-1-pyrrolidinyl)-2-(2-morpholinylethylaminocarbonyl) pyridine.

MS(m/z): 505(M+H)+

Example 318

(1) A mixture of diisopropylamine 2.54 g, a 1.6M solution of n-butyl lithium in hexane 15.7 ml and tetrahydrofuran 100 ml is stirred for 30 minutes on a dry ice-acetone bath. Thereto is added 2,4,6-trichloropyrimidine 2.00 g in tetrahydrofuran 8 ml over a period of 30 minutes, followed by further one hour agitation. The reaction mixture is poured into dry ice, and the mixture is stirred for a hour at room temperature. The reaction mixture is made acidic with 10% hydrochloric acid 20 ml, diluted with an aqueous saturated sodium chloride solution and extracted with ethyl acetate. The organic layer is washed, dried and concentrated in vacuo. The solvent is removed by azeotrope with chloroform and the resulting hemisolid is triturated with hexane to give 5-carboxy-2,4,6-trichloropyrimidine as a crystalline powder, 1.51 g. mp 150–153° C.

(2) To a mixture of 5-carboxy-2,4,6-trichloropyrimidine (prepared in the above (1)) 100 mg, triethylamine 89 mg in dimethylformamide 3 ml is added at room temperature a 1.0M solution of benzylthiol in tetrahydrofuran 0.44 ml, and the mixture is stirred for 1 hour. The reaction mixture is diluted with a 10% aqueous citric acid solution and extracted with ethyl acetate. The organic layer is washed, dried and concentrated in vacuo to give 4-benzylthio-5-carboxy-2,6-dichloropyrimidine as a pale yellow oil.

(3) A mixture of whole amount of 4-benzylthio-5-carboxy-2,6-dichloropyrimidine prepared in the above (2), sodium hydrogen carbonate 55 mg, methyl iodide 0.2 ml, dimethylformamide 3 ml and tetrahydrofuran 1 ml is stirred at room temperature for 1 hour. The reaction mixture is diluted with a 10% aqueous citric acid solution and extracted with ethyl acetate. The organic layer is washed, dried and concentrated in vacuo. The residue is separated with preparative thin-layer chromatography (solvent; hexane:ethyl acetate=10:1) to give a mixture of 4-benzylthio-5-methoxycarbonyl-2,6-dichloropyrimidine and 4,6-dibenzylthio-5-methoxycarbonyl-2-chloropyrimidine as a colorless oil, 123 mg.

(4) A mixture of 4-benzylthio-5-methoxycarbonyl-2,6-dichloropyrimidine and 4,6-dibenzylthio-5-methoxycarbonyl-2-chloropyrimidine (prepared in the above (3)) 97 mg, 4-hydroxypiperidine 29 mg, triethylamine 29 mg and toluene 2.5 mg is stirred at room temperature for 4 hours. Further, 4-hydroxypiperidine 3 mg and triethylamine 3 mg are added thereto, and the mixture is stirred for 30 minutes. The reaction mixture is diluted with a 10% aqueous citric acid solution and extracted with ethyl acetate. The organic layer is washed, dried and concentrated in vacuo to give 4-benzylthio-5-methoxycarbonyl-6-(4-hydroxypiperidine-1-yl)-2-chloropyrimidine as a colorless caramel, 120 mg.

(5) A mixture of 4-benzylthio-5-methoxycarbonyl-6-(4-hydroxypiperidine-1-yl)-2-chloropyrimidine (prepared in the above (4)) 120 mg, 5,6,7,8-tetrahydroimidazo[1,2-a]pyrazine 70 mg, triethylamine 57 mg and N,N-dimethylacetamide 3 ml is stirred at 10° C. for 3 hours. The reaction mixture is diluted with an aqueous citric acid solution and extracted with ethyl acetate. The water layer is made basic with an aqueous sodium hydrogen carbonate solution and extracted with ethyl acetate. The organic layer is washed, dried and concentrated in vacuo to give 4-benzylthio-5-methoxycarbonyl-6-(4-hydroxypiperidin-1-yl)-2-(5,6,7,8-tetrahydroimidazo[1,2-a]pyrazin-7-yl)pyrimidine as a colorless foam, 105 mg.

IR (Neat+CHCl$_3$)cm$^{-1}$: 3050–3600, 1695, 1533, 1503, 1433 APCI-MS(m/z): 481(M+H)+

(6) To a solution of 4-benzylthio-5-methoxycarbonyl-6-(4-hydroxypiperidin-1-yl)-2-(5,6,7,8-tetrahydroimidazo[1,2-a]pyrazin-7-yl)pyrimidine (prepared in the above (5)) 93 mg in chloroform 2.5 ml is dropped a solution of m-chloroperbenzoic acid 44 mg in chloroform 4 ml over a period of 10 minutes on a ice bath, and the mixture is stirred for 1.5 hours. The mixture is diluted with an aqueous sodium hydrogen carbonate solution and extracted with ethyl acetate. The organic layer is washed, dried and concentrated in vacuo to give 4-benzylsulfinyl-5-methoxycarbonyl-6-(4-hydroxypiperidin-1-yl)-2-(5,6,7,8-tetrahydroimidazo[1,2-a]pyrazin-7-yl)pyrimidine as a slightly yellow foam, 83 mg.

(7) A mixture of 4-benzylsulfinyl-5-methoxycarbonyl-6-(4-hydroxypiperidin-1-yl)-2-(5,6,7,8-tetrahydroimidazo[1,2-a]pyrazin-7-yl)pyrimidine (prepared in the above (6)) 83 mg, 3-chloro-4-methoxybenzylamine 86 mg, triethylamine 51 mg and N,N-dimethylacetoamide 3 ml is stirred at 110° C. for 1 hour. The reaction mixture is diluted with ice water and extracted with ethyl acetate. The organic layer is washed, dried and concentrated in vacuo. The residue is separated with silica gel chromatography (solvent; ethyl acetate→ethyl acetate:methanol=15:1→10:1) and crystallized from a mixture of methanol, ethyl acetate and isopropyl ether to give 4-(3-chloro-4-methoxybenzylamino)-5-methoxycarbonyl-6-(4-hydroxypiperidin-1-yl)-2-(5,6,7,8-tetrahydroimidazo[1,2-a]pyrazin-7-yl)pyrimidine as a colorless crystalline powder 43 mg. mp 192–194° C.

IR (Nujol)cm$^{-1}$: 3380, 1664, 1572, 1533, 1433 APCI-MS (m/z): 528(M+H)+

Example 319

(1) A N,N-dimethylformamide solution 6 ml of 3-chloro-4-methoxybenzylamine 1.51 g and triethylamine 2.46 g is dropped over a period of 25 minutes under ice cooling a solution of 5-carboxy-2,4,6-trichloropyrimidine (prepared in Example 318 (1)) 2.00 g in N,N-dimethylformamide 12 ml, and the mixture is further stirred for 90 minutes. The reaction mixture is diluted with a 10% aqueous citric acid solution and extracted with ethyl acetate. The combined extract is washed with water and an aqueous sodium chloride solution, dried over anhydrous sodium sulfate and concentrated in vacuo to give 4-(3-chloro-4-methoxybenzylamino)-2,6-dichloropyrimidine-5-carboxylic acid as a pale brown crystalline powder 2.92 g. mp 144–151° C.

(2) To a mixture of 11 ml of the carboxylic acid (prepared in the above (1)) 2.92 g and sodium hydrogen carbonate 0.744 g in N,N-dimethylformamide is added methyl iodide 1.00 ml, and the mixture is stirred at room temperature for 16 hours. The reaction mixture is diluted with a 10% aqueous citric acid solution and extracted with ethyl acetate. The combined extract is washed with water and an aqueous saturated sodium chloride solution, dried over anhydrous sodium sulfate and concentrated in vacuo. The residue is separated with silica gel chromatography (After effuluence with solvent (hexane:chloroform=2:1), solvent; hexane:chloroform:ethyl acetate=20:10:1) to give 4-(3-chloro-4-methoxybenzylamino)-5-methoxycarbonyl-2,6-dichloropyrimidine as a colorless crystalline powder 2.31 g.

mp 119–121° C. IR (Nujol)cm$^{-1}$: 3320, 1689, 1591, 1573, 1507, 1460 APCI-MS(m/z): 376(M+H)$^{+}$ (3) A mixture of 4-(3-chloro-4-methoxybenzylamino)-5-methoxycarbonyl-2,6-dichloropyrimidine (prepared in the above (2)) 150 mg, a 1.0M solution of benzylthiol in dimethylformamide 0.40 ml, triethylamine 40 mg and dimethylformamide 2.5 ml is stirred at room temperature for 2.5 days. The reaction mixture is diluted with water and extracted with ethyl acetate. The organic layer is washed, dried and concentrated in vacuo. The residue is separated with preparative thin-layer chromatography (solvent; hexane:chloroform:ethyl acetate=30:30:4) and crystallized from isopropyl ether to give 4-(3-chloro-4-methoxybenzylamino)-5-methoxycarbonyl-6-chloro-2-benzylthiopyrimidine as a colorless crystalline powder 125 mg. mp 89–90° C.

(4) A mixture of 4-(3-chloro-4-methoxybenzylamino)-5-methoxycarbonyl-6-chloro-2-benzylthiopyrimidine (prepared in the above (3)) 108 mg, 5,6,7,8-tetrahydroimidazo[1,2-a]pyrazine 57 mg, triethylamine 47 mg and N,N-dimethylacetamide 2.5 ml is stirred at 60° C. for 1 hour. The reaction mixture is diluted with water and extracted with ethyl acetate. The organic layer is washed, dried and concentrated in vacuo. The residue is separated with silica gel chromatography (solvent; chloroform:methanol=200:1) to give 4-(3-chloro-4-methoxybenzylamino)-5-methoxycarbonyl-6-(5,6,7,8-tetrahydroimidazo[1,2-a]pyrazin-7-yl)-2-benzylthiopyrimidine as a colorless foam, 129 mg.

IR (Nujol)cm$^{-1}$: 3335, 1665, 1567, 1518, 1503, 1456 APCI-MS(m/z): 551(M+H)$^{+}$ (5) To a chloroform solution 2 ml of 4-(3-chloro-4-methoxybenzylamino)-5-methoxycarbonyl-6-(5,6,7,8-tetrahydroimidazo[1,2-a]pyrazin-7-yl)-2-benzylthiopyrimidine (prepared in the above (4)) 104 mg is dropped a solution of m-chloroperbenzoic acid 43 mg in chloroform 3 ml over a period of 20 minutes on an ice bath, and the mixture is stirred for 1 hour. The reaction mixture is diluted with an aqueous saturated sodium hydrogen carbonate and extracted with ethyl acetate. The organic layer is washed, dried and concentrated in vacuo to give 4-(3-chloro-4-methoxybenzylamino)-5-methoxycarbonyl-6-(5,6,7,8-tetrahydroimidazo[1,2-a]pyrazin-7-yl)-2-benzylsulfinylpyrimidine as a slightly yellow caramel.

(6) A mixture of whole amount of 4-(3-chloro-4-methoxybenzylamino)-5-methoxycarbonyl-6-(5,6,7,8-tetrahydroimidazo[1,2-a]pyrazin-7-yl)-2-benzylsulfinylpyrimidine (prepared in the above (5)), 4-hydroxypiperidine 57 mg, triethylamine 57 mg and N,N-dimethylacetamide 3 ml is stirred at 60° C. for 1.5 hours. After cooling the reaction mixture is diluted with ice water and extracted with ethyl acetate. The organic layer is washed, dried and concentrated in vacuo. The residue is crystallized from a mixture of ethyl acetate and isopropyl ether to give of 4-(3-chloro-4-methoxybenzylamino)-5-methoxycarbonyl-6-(5,6,7,8-tetrahydroimidazo[1,2-a]pyrazin-7-yl)-2-(4-hydroxypiperidin-1-yl)pyrimidine as a colorless crystalline powder 75 mg.

mp 191–194° C. IR (Nujol)cm$^{-1}$: 3342, 3167, 1648, 1567, 1529, 1462, 1441 APCI-MS(m/z): 528(M+H)$^{+}$ Example 320

(1) To a solution of diisopropylamine 11.93 g in tetrahydrofuran 350 ml is dropped a 1.6M solution of n-butyl lithium in hexane 73.7 ml over a period of 20 minutes on dry ice-acetone bath, and the mixture is stirred for 30 minutes. Thereto is added 4,6-dichloro-2-methylthiopyrimidine 10.00 g in tetrahydrofuran 50 ml over a period of 1 hour on a dry ice-acetone bath, followed by further one hour agitation. The reaction mixture is poured into dry ice and the mixture is stirred for 1.5 hours at room temperature. The reaction mixture is made acidic with 10% hydrochloric acid, diluted with water and extracted with ethyl acetate. The organic layer is washed, dried and condensed in vacuo. The resulting solid is triturated with hexane to give 4,6-dichloro-5-carboxy-2-methylthiopyrimidine as a brown crystalline powder, 10.42 g. mp 151–158° C.(decomposition)

IR (Nujol)cm$^{-1}$: 1707, 1547, 1377 ESI-MS(m/z): 237(M−H)$^{-}$ (2) To a mixture of 4,6-dichloro-5-carboxy-2-methylthiopyrimidine (prepared in the above (1)) 500 mg and triethylamine 0.58 ml in dimethylformamide 3 ml is added 3-chloro-4-methoxybenzylamine 359 mg in dimethylformamide 3 ml at room temperature over a period of 15 minutes, and the mixture is stirred for 4 hour. The reaction mixture is diluted with a 10% aqueous citric acid solution and extracted with ethyl acetate. The organic layer is washed, dried and concentrated in vacuo to give 4-(3-chloro-4-methoxybenzylamino)-5-carboxy-6-chloro-2-methylthiopyrimidine as a slightly brown powder.

(3) A mixture of whole amount of 4-(3-chlorp-4-methoxybenzylamino)-5-carboxy-6-chloro-2-methylthiopyrimidine prepared in the above (2), sodium hydrogen carbonate 193 mg, methyl iodide 0.20 ml and dimethylformamide 4 ml is stirred at room temperature for 3 hours. Further, methyl iodide 0.13 ml is added thereto and the mixture is stirred for 12 hours. The reaction mixture is diluted a 10% aqueous citric acid solution and extracted with ethyl acetate. The organic layer is washed, dried and concentrated in vacuo. The residue is separated with silica gel chromatography (solvent; hexane:chloroform:ethyl acetate=20:10:1) to give 4-(3-chloro-4-methoxybenzylamino)-5-methoxycarbonyl-6-chloro-2-methylthiopyrimidine as a colorless crystalline powder 441 mg. mp 105–108° C.

(4) A mixture of 4-(3-chloro-4-methoxybenzylamino)-5-methoxycarbonyl-6-chloro-2-methylthiopyrimidine (prepared in the above (3)) 100 mg, 4-hydroxypiperidine 78 mg, triethylamine 0.11 ml and N,N-dimethylacetamide 3 ml is stirred at room temperature for 1 hour. The reaction mixture is diluted a 10% aqueous citric acid solution and extracted with ethyl acetate. The organic layer is washed, dried and concentrated in vacuo to give 4-(3-chloro-4-methoxybenzylamino)-5-methoxycarbonyl-6-(4-hydroxypiperidin-1-yl)-2-methylthiopyrimidine as a colorless caramel 132 mg.

IR (Neat+CHCl$_3$)cm$^{-1}$: 3345, 1663, 1569, 1519 APCI-MS(m/z): 453(M+H)$^{+}$ (5) A mixture of 4-(3-chloro-4-methoxybenzylamino)-5-methoxycarbonyl-6-(4-hydroxypiperidin-1-yl)-2-methylthiopyrimidine (prepared in the above (4)) 121 mg in chloroform 3 ml is dropped a solution of m-chloroperbenzoic acid 54 mg in chloroform 4 ml on an ice bath over a period of 15 minutes, and the mixture is stirred for 1 hour. The reaction mixture is diluted with an aqueous sodium hydrogen carbonate solution and extracted with ethyl acetate. The organic layer is washed, dried and concentrated in vacuo to give 4-(3-chloro-4-methoxybenzylamino)-5-methoxycarbonyl-6-(4-hydroxypiperidin-1 yl)-2-methylsulfinylpyrimidine as a colorless caramel.

(6) A mixture of whole amount) of 4-(3-chloro-4-methoxybenzylamino)-5-methoxycarbonyl-6-(4-hydroxypiperidin-1-yl)-2-methylsulfinylpyrimidine (prepared in the above (5)), 5,6,7,8-tetrahydroimidazo[1,2-a]pyrazine 73 mg, triethylamine 0.083 ml and N,N-dimethylacetamide 4 ml is stirred at 110° C. for 4 hours. After cooling the reaction mixture is diluted with a 10% aqueous citric acid solution and washed with ethyl acetate. The organic layer is extracted with a 10% aqueous citric acid solution. The water layer is made basic with sodium hydrogen carbonate and extracted with ethyl acetate. The ethyl acetate layer is washed, dried and concentrated in vacuo. The residue is separated with silica gel chromatography (solvent; chloroform:methanol=100:1→50:1), and then crystallized from a mixture of ethyl acetate, methanol and isopropyl ether to give 4-(3-chloro-4-methoxybenzylamino)-5-methoxycarbonyl-6-(4-hydroxypiperidin-1-yl)-2-(5,6,7,8-tetrahydroimidazo[1,2-a]pyrazin-7-yl)pyrimidine as a colorless crystalline powder 20 mg.

mp 179–180° C. IR (Nujol)cm$^{-1}$: 3380, 3181, 1664, 1572, 1533, 1463 APCI-MS(m/z): 528(M+H)$^+$ Example 321

(1) A mixture of 4-(3-chloro-4-methoxybenzylamino)-5-carboxy-6-chloro-2-methylthiopyrimidine 500 mg and thionyl chloride 2 ml is refluxed for 10 minutes. After reaction thionyl chloride is removed and the solvent is removed in azeotrope with methylene chloride to give 4-(3-chloro-4-methoxybenzylamino)-5-chloroformyl-6-chloro-2-methylthiopyrimidine.

(2) A mixture of whole amount of 4-(3-chloro-4-methoxybenzylamino)-5-chloroformyl-6-chloro-2-methylthiopyrimidine (prepared in the above (1)), methylene chloride 15 ml and 2-benzyloxyethanol 224 mg is refluxed for 30 minutes. After cooling the reaction mixture is diluted with water and neutralized with an aqueous saturated sodium hydrogen carbonate solution. The solution is washed with ethyl acetate. The methylene chloride layer is diluted with ethyl acetate, washed, dried and concentrated in vacuo. The residue is separated with silica gel chromatography (solvent; hexane:ethyl acetate=5:1) to give 4-(3-chloro-4-methoxybenzylamino)-5-(2-benzyloxyethoxycarbonyl)-6-chloro-2-methylthiopyrimidine as a colorless oil 655 mg.

IR (Neat)cm$^{-1}$: 3340, 1731, 1674, 1567, 1555, 1503 APCI-MS(m/z): 508(M+H)$^+$ (3) A mixture of 4-(3-chloro-4-methoxybenzylamino)-5-(2-benzyloxyethoxycarbonyl)-6-chloro-2-methylthiopyrimidine (prepared in the above (2)) 636 mg, 4-hydroxypiperidine 190 mg, triethylamine 0.26 ml and dimethylformamide 4 ml is stirred at room temperature for 30 minutes. The reaction mixture is diluted a 10% aqueous citric acid solution and extracted with ethyl acetate. The organic layer is washed, dried and concentrated in vacuo to give 4-(3-chloro-4-methoxybenzylamino)-5-(2-benzyloxyethoxycarbonyl-6-(4-hydroxypiperidin-1-yl)-2-methylthiopyrimidine as a colorless caramel, 713 mg.

IR (Neat+CHCl$_3$)cm$^{-1}$: 3351, 1661, 1568, 1519 APCI-MS(m/z): 573(M+H)$^+$ (4) To a solution of 4-(3-chloro-4-methoxybenzylamino)-5-(2-benzyloxyethoxycarbonyl)-6-(4-hydroxypiperidin-1-yl)-2-methylthiopyrimidine (prepared in the above (3)) 100 mg in methylene chloride 3 ml is added at room temperature a solution of m-chloroperbenzoic acid 79 mg in methylene chloride 2 ml, and the mixture is stirred for 30 minutes. The reaction mixture is diluted with an aqueous sodium hydrogen carbonate solution and extracted with ethyl acetate. The organic layer is washed, dried and concentrated in vacuo to give 4-(3-chloro-4-methoxybenzylamino)-5-(2-benzyloxyethoxycarbonyl)-6-(4-hydroxypiperidin-1-yl)-2-methylsulfinylpyrimidine.

(5) A mixture of whole amount of 4-(3-chloro-4-methoxybenzylamino)-5-(2-benzyloxyethoxycarbonyl)-6-(4-hydroxypiperidin-1-yl)-2-methylsulfinylpyrimidine (prepared in the above (4)), L-prolinol 53 mg, triethylamine 53 mg and dimethylformamide 4 ml is stirred at room temperature for 1.5 hours and then at 65° C. for 3.5 hours. After cooling the reaction mixture is diluted with water and extracted with ethyl acetate. The ethyl acetate layer is washed, dried and concentrated in vacuo. The residue is separated with silica gel chromatography (solvent; chloroform: ethyl acetate=1:2) to give 4-(3-chloro-4-methoxybenzylamino)-5-(2-benzyloxyethoxycarbonyl)-6-(4-hydroxypiperidin-1-yl)-2-(2-hydroxymethyl-1-pyrrolidinyl)pyrimidine as a colorless caramel 96 mg.

IR (Neat+CHCl$_3$)cm$^{-1}$: 3345, 1650, 1573, 1528, 1501, 1454 APCI-MS(m/z): 626(M+H)+

(6) A mixture of 4-(3-chloro-4-methoxybenzylamino)-5-(2-benzyloxyethoxycarbonyl)-6-(4-hydroxypiperidin-1-yl)-2-(2-hydroxymethyl-1-ptrrolidinyl)pyrimidine (prepared in the above (5)) 60 mg, 28% sodium methoxide/methanol 185 mg and tetrahydrofuran 2.5 ml is stirred at 60° C. for 2.5 hours. After cooling the reaction mixture is diluted with a 10% aqueous citric acid solution and neutralized with an aqueous saturated sodium hydrogen carbonate solution. The solution is extracted with ethyl acetate. The ethyl acetate layer is washed, dried and concentrated in vacuo. The residue is separated with preparative thin-layer silica gel chromatography (solvent; ethyl acetate) to give 4-(3-chloro-4-methoxybenzylamino)-5-methoxycarbonyl-6-(4-hydroxypiperidin-1-yl)-2-(2-hydroxymethyl-1-pyrrolidinyl)pyrimidine as a colorless caramel 36 mg.

IR (Nujol)cm$^{-1}$: 3332, 1654, 1575, 1527, 1501, 1459 APCI-MS(m/z): 506(M+H)+

Example 322

(1) To a solution of 5-carboxy-2,4,6-trichloropyrimidine 10.0 g in dimethylformamide 45 ml is added a suspension of 3-chloro-4-methoxybenzylamine 4.82 g and triethylamine 6.98 ml in dimethylformamide 40 ml over a period of 20 minutes on ice bath, and the mixture is stirred for 1 hour. The reaction mixture is diluted with a 10% aqueous citric acid solution and extracted with ethyl acetate. The organic layer is washed, dried and concentrated in vacuo to give 4-(3-chloro-4-methoxybenzylamino)-5-carboxy-2,6-dichloropyrimidine as a pale brown solid, 17.59 g. mp 150–151° C.

(2) A mixture of 4-(3-chloro-4-methoxybenzylamino)-5-carboxy-2,6-dichloropyrimidine (prepared in the above (1)) 17.55 g, sodium hydrogen carbonate 4.07 g, methyl iodide 5.48 ml and dimethylformamide 50 ml is stirred overnight at room temperature. The reaction mixture is diluted an aqueous saturated sodium hydrogen carbonate solution and extracted with ethyl acetate. The organic layer is washed, dried and concentrated in vacuo to give a pale yellow solid. The solid is suspended in a mixture of methylene chloride, isopropyl ether and hexane, and filtered. The precipitate is washed with a mixture of isopropyl ether and hexane to give 4-(3-chloro-4-methoxybenzylamino)-5-methoxycarbonyl-2,6-dichloropyrimidine as a colorless crystalline powder 8.64 g. mp 118–119° C.

(3) To a solution of 4-(3-chloro-4-methoxybenzylamino)-5-methoxycarbonyl-2,6-dichloropyrimidine (prepared in the above (2)) 1.01 g in dimethylformamide 10 ml are added 4-hydroxypiperidine 338 mg and triethylamine 411 mg at room temperature, and the mixture is stirred for 15 minutes. The reaction mixture is diluted with water and extracted with ethyl acetate. The organic layer is washed, dried and concentrated in vacuo to give a slightly yellow oil. The oil is separated with silica gel chromatography (solvent; chloroform: ethyl acetate=8:1→5:1), and further separated with silica gel chromatography (solvent; hexane:ethyl acetate=1:1) to give 4-(3-chloro-4-methoxybenzylamino)-5-methoxycarbonyl-6-chloro-2-(4-hydroxypiperidin-1-yl)pyrimidine as colorless crystals 540 mg (mp 138–139° C.) and 4-(3-chloro-4-methoxybenzylamino)-5-methoxycarbonyl-6-(4-hydroxypiperidin-1-yl)-2-chloropyrimidine as a colorless foam, 617 mg.

(4) To a solution of 4-(3-chloro-4-methoxybenzylamino)-5-methoxycarbonyl-6-chloro-2-(4-hydroxypiperidin-1-yl)pyrimidine (prepared in the above (3)) 56 mg in N,N-dimethylacetamide 0.5 ml are added a solution of 5,6,7,8-tetrahydroimidazo[1,2-a]pyrazine 31 mg in N,N-dimethylacetamide 0.5 ml and triethylamine 27 μl at room temperature, and the mixture is stirred at 80–90° C. for 5 hours. The reaction mixture is diluted with an aqueous citric acid solution, made basic with an aqueous sodium hydrogen carbonate solution and extracted with ethyl acetate. The organic layer is washed, dried and concentrated in vacuo to give 4-(3-chloro-4-methoxybenzylamino)-5-methoxycarbonyl-6-(5,6,7,8-tetrahydroimidazo[1,2-a]pyrazin-7-yl)-2-(4-hydroxypiperidin-1-yl)pyrimidine as a pale yellow powder, 66 mg.

mp 191–194° C. IR (Nujol)cm$^{-1}$: 3342, 3167, 1648, 1567, 1529, 1462, 1441 APCI-MS (m/z): 528(M+H)$^+$ Example 323

(1) 4-(3-Chloro-4-methoxybenzylamino)-5-methoxycarbonyl-6-chloro-2-(4-methylpiperazin-1-yl)pyrimidine is obtained as a yellow crystalline powder by reacting 4-(3-chloro-4-methoxybenzylamino)-5-methoxycarbonyl-2,6-dichloropyrimidine and N-methylpiperazine in the same manner as Example 322 (3).

IR (Nujol)cm$^{-1}$: 3314, 1659, 1585, 1539, 1241 APCI-MS (m/z): 440(M+H)$^+$ (2) 4-(3-Chloro-4-methoxybenzylamino)-5-methoxycarbonyl-6-(5,6,7,8-tetrahydroimidazo[1,2-a]pyrazin-7-yl)-2-(4-methylpiperazin-1-yl)pyrimidine is obtained by reacting 4-(3-chloro-4-methoxybenzylamino)-5-methoxycarbonyl-6-chloro-2-(4-methylpiperazin-1-yl)pyrimidine (prepared in the above (1)) and 5,6,7,8-tetrahydroimidazo[1,2-a]pyrazine in the same manner as Example 463(4).

The above compound is made into its hydrochloride in the conventional manner.

IR (Nujol)cm$^{-1}$: 3386, 1668, 1623, 1461, 1377 APCI-MS (m/z): 527(M+H)$^+$

Example 324

To a solution of 6,7-dihydro-5-pyrrolo[3,4-b]pyridine 77 mg in N,N-dimethylacetamide 2 ml are added 4-(3-chloro-4-methoxybenzylamino)-5-methoxycarbonyl-6-(4-hydroxypiperidin-1-yl)-2-chloropyrimidine (prepared in Example 322 (3)) 105 mg and triethylamine 75 mg, and the mixture is stirred at room temperature for 1 hour, at 80–90° C. for 3 hours and then at 100–110° C. for 2 hours. The reaction mixture is diluted with water and extracted with ethyl acetate. The ethyl acetate layer is washed, dried and concentrated in vacuo to give a dark brown oil. The oil is separated with silica gel chromatography (solvent; chloroform:ethyl acetate=1:1→ethyl acetate) to give 4-(3-chloro-4-methoxybenzylamino)-5-methoxycarbonyl-6-(4-hydroxypiperidin-1-yl)-2-(6,7-dihydro-5-pyrrolo[3,4-b]pyridin-6-yl-)pyrimidine as a slightly brown solid, 76 mg. mp 165–172° C. (decomposition)

Example 325

(1) 4-(3-Chloro-4-methoxybenzylamino)-5-methoxycarbonyl-6-(4-hydroxypiperidin-1-yl)-2-(2-pyridylmethoxy)pyrimidine is obtained as a foam by reacting 4-(3-chloro-4-methoxybenzylamino)-5-methoxycarbonyl-6-(4-hydroxypiperidin-1-yl)-2-chloropyrimidine and 2-(hydroxymethyl)pyridine in the same manner as Example 324.

IR (Neat+CHCl$_3$)cm$^{-1}$: 3344, 1663, 1582, 1537, 1501, 1440, 1410, 1345, 1260 APCI-MS(m/z): 514(M+H)$^+$ Example 326

(1) To a solution of 4-(2-hydroxyethyl)phenol 9.50 g in acetic acid 60 ml is dropped bromine 3.54 ml over a period of 10 minutes on a water bath, and the mixture is stirred for 15 minutes. The reaction mixture is diluted with water and extracted with ethyl acetate. The ethyl acetate layer is washed, dried and concentrated in vacuo. The residue is dissolved in methanol 120 ml and thereto is added potassium carbonate 25 g. The mixture is stirred at room temperature for 5 hours. and then diluted with water and with ethyl acetate. The solution is acidified with concentrated sulfuric acid. The organic layer is extracted with ethyl acetate, washed, dried and concentrated in vacuo. The residue is crystallized from chloroform to give 2-bromo-4-(2-hydroxyethyl)phenol as a slightly brown crystalline powder 9.37 g. mp 83–85° C.

Furthermore, a mother liquid is concentrated in vacuo and separated with silica gel chromatography (solvent; chloroform:ethyl acetate=10:1→5:1), to give 2-bromo-4-(2-hydroxyethyl)phenol as a colorless crystalline powder 2.72 g. mp 85–86° C.

(2) To a solution of 2-bromo-4-(2-hydroxyethyl)phenol (prepared in the above (1)) 11.79 g in N,N-dimethylacetamide 155 ml are added 28% sodium methoxide/methanol 9.43 g and merryfield resin (chloro methylated stylene-divinylbenzene copolymer) 15.28 g at room temperature, and the mixture is stirred for 18 hours at 80° C. After cooling the resin is filtered, washed and dried to give 2-bromo-4-(2-hydroxyethyl)phenoxymethyl resin 21.50 g.

(3) A mixture of 4-(3-chloro-4-methoxybenzylamino)-5-carboxy-6-chloro-2-methylthiopyrimidine 10.50 g and thionyl chloride 25 ml is stirred for 20 minutes at 75° C. After reaction thionyl chloride is distilled off and the solvent is removed by azeotrope with methylene chloride to give 4-(3-chloro-4-methoxybenzylamino)-5-chloroformyl-6-chloro-2-methylthiopyrimidine.

(4) To a mixture of 2-bromo-4-(2-hydroxyethyl)phenoxymethyl resin (prepared in the above (2)) 8.84 g and phenyldimethylamine (6.23 ml) in methylene chloride 70 ml is added a solution of a whole amount of 4-(3-chloro-4-methoxybenzylamino)-5-chloroformyl-6-chloro-2-methylthiopyrimidine (prepared in the above (3)) in methylene chloride 40 ml at room temperature, and the mixture is stirred for 21 hours. After filtration the resin is washed and dried to give 4-(3-chloro-4-methoxybenzylamino)-5-[2-(4-resin-methoxy-3-bromophenyl)ethoxycarbonyl]-6-chloro-2-methylthiopyrimidine 13.60 g.

Examples 327–335

(1) 4-(3-Chloro-4-methoxybenzylamino)-5-[2-(4-resin-methoxy-3-bromophenyl)ethoxycarbonyl]-6-chloro-2-methylthiopyrimidine (prepared in Example 326(4)) and a corresponding starting compound are reacted in the same manner as Example 312(3), namely the resin combined with a compound is suspended in dimethylformamide and thereto are added triethylamine (3 mol) and R—H (an amine represented by the following Table 16) (3 mol), and the mixture is stirred for 16 hours at room temperature. The resin is filtered, washed with dimethylformamide, hydrous dimethylformamide (50%), water, methanol, tetrahydrofuran, isopropyl ether, respectively several times, and then dried in vacuo to give each compound listed in the following Table 16.

(2) Each resin prepared in the above (1) and a corresponding starting compound are reacted in the same manner as Example 321(4), namely the resin reacted is suspended in methylene chloride and swelled, and thereto are added a solution of m-chloroperbenzoic acid (1–2.5 mol) in methylene chloride and the mixture is stirred for 16 hours at room temperature. The resin is filtered, washed with methylene chloride, dimethylacetamide, methanol and isopropyl ether, respectively several times, and then dried in vacuo to give each compound listed in the following Table 17.

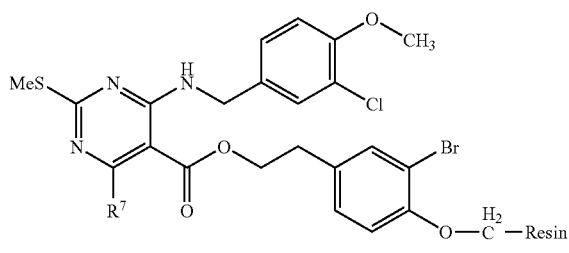

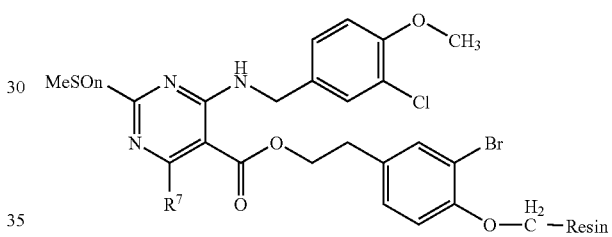

TABLE 16

| Example No. | R⁷ |
|---|---|
| 327-1 | ![structure] |
| 328-1 | ![structure] |
| 329-1 | ![structure] |
| 330-1 | ![structure] |
| 331-1 | ![structure] |
| 332-1 | ![structure] |
| 333-1 | —NMe₂ |
| 334-1 | ![structure] |
| 335-1 | ![structure] |

TABLE 17

| Example No. | R⁷ | n |
|---|---|---|
| 327-2 | ![structure] | 1 |
| 328-2 | ![structure] | 2 |
| 329-2 | ![structure] | 2 |
| 330-2 | ![structure] | 2 |
| 331-2 | ![structure] | 2 |
| 332-2 | ![structure] | 1 |
| 333-2 | —NMe₂ | 2 |

TABLE 17-continued

| Example No. | R⁷ | n |
|---|---|---|
| 334-2 | 1-methylpyrrolidin-2-yl-CH(OH)- | 2 |
| 335-2 | -N(CH₃)CH₂CH₂OH | 2 |

(3) Each resin prepared in the above (2) and a corresponding starting compound are reacted in the same manner as Example 321(5), namely the resin reacted is suspended in dimethylacetamide and thereto are added triethylamine (4 mol) and L-prolinol (4 mol), and the mixture is stirred for 9 hours at 75° C. After cooling to room temperature the resin is filtered, washed with dimethylacetamide and methanol, respectively several times to give each compound listed in the following Table 18.

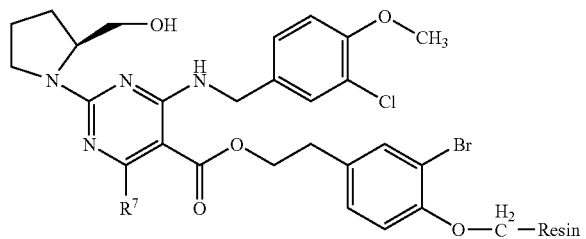

TABLE 18

| Example No. | R⁷ |
|---|---|
| 327-3 | -NHCH₂-(pyrimidin-2-yl) |
| 328-3 | 7-methyl-5,6,7,8-tetrahydroimidazo[1,2-a]pyrazin-2-yl |
| 329-3 | -NH-(trans-4-hydroxycyclohexyl) |
| 330-3 | morpholin-4-yl |
| 331-3 | 4-(2-hydroxyethyl)piperidin-1-yl |
| 332-3 | -NHCH₂CH₂-(morpholin-4-yl) |
| 333-3 | -NMe₂ |

TABLE 18-continued

| Example No. | R⁷ |
|---|---|
| 334-3 | 1-methylpyrrolidin-2-yl-CH(OH)- |
| 335-3 | -N(CH₃)CH₂CH₂OH |

(4) Each resin prepared in the above (3) and a corresponding starting compound are reacted in the same manner as Example 321(6), namely the resin reacted is suspended in tetrahydrofuran and thereto is added sodium methoxide/methanol (10 mol). The mixture is stirred at 65° C. for 2.5 hours. After cooling the reaction mixture is diluted with a 10% aqueous citric acid solution and neutralized with an aqueous saturated sodium hydrogen carbonate solution. The solution is extracted with ethyl acetate. The ethyl acetate layer is washed with an aqueous sodium chloride solution, dried over anhydrous magnesium sulfate and concentrated in vacuo. The residue is purified with silica gel chromatography, preparative thin-layer chromatography, etc. to give compounds listed in Table 19, Examples 332-4, 334-4 and 335-4.

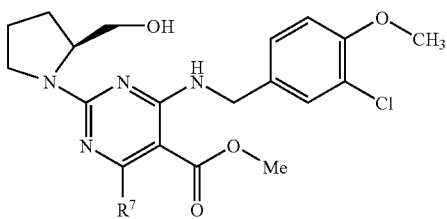

TABLE 19

| Example No. | R⁷ | Physical property etc. |
|---|---|---|
| 327-4 | -NHCH₂-(pyrimidin-2-yl) | APCI-MS(m/z): 514(M + H)⁺ |
| 328-4 | 7-methyl-5,6,7,8-tetrahydroimidazo[1,2-a]pyrazin-2-yl | APCI-MS(m/z): 528(M + H)⁺ |
| 329-4 | -NH-(trans-4-hydroxycyclohexyl) | APCI-MS(m/z): 520(M + H)⁺ |
| 330-4 | morpholin-4-yl | APCI-MS(m/z): 492(M + H)⁺ |
| 331-4 | 4-(2-hydroxyethyl)piperidin-1-yl | APCI-MS(m/z): 534(M + H)⁺ |
| 333-4 | -NMe₂ | APCI-MS(m/z): 450(M + H)⁺ |

Example 332-4

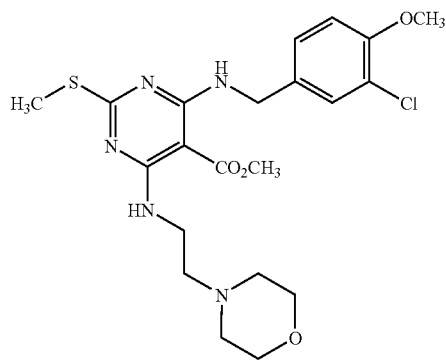

APCI-MS(m/z): 482(M+H)+

Example 335-4

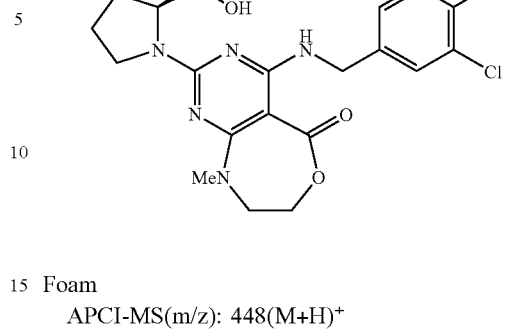

Foam
APCI-MS(m/z): 448(M+H)+

Example 334-4

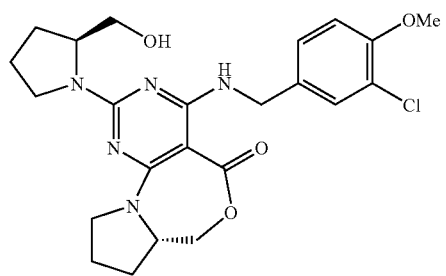

Foam
APCI-MS(m/z): 474(M+H)+

Examples 336 to 346

4-(3-Chloro-4-methoxybenzylamino)-5-[2-(4-resin-methoxy-3-bromophenyl)ethoxycarbonyl]-6-chloro-2-methylthiopyrimidine prepared in Example 326(4) and a corresponding starting compound (R$^1$H) are reacted in the same manner as Example 327–335(1)–(4), to give compounds listed in the following Table 20 and compouds of Exammples 340 and 341.

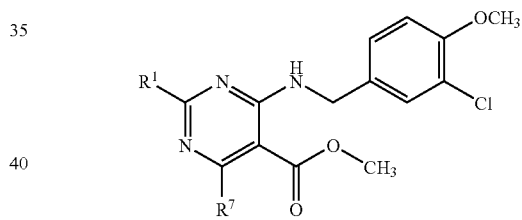

TABLE 20

| Example No. | R$^7$ | R$^1$ | Physical property etc. |
|---|---|---|---|
| 336 | | | mp: 184–186° C. |
| 337 | | | APCI-MS(m/z): 542(M + H)+ |
| 338 | | | APCI-MS(m/z): 514(M + H)+ |
| 339 | —NMe$_2$ | | APCI-MS(m/z): 472(M + H)+ |

Example 340

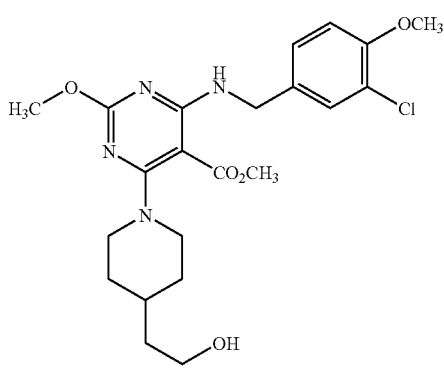

mp 111–114° C.

Example 341

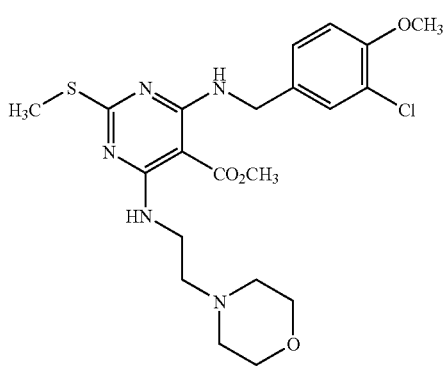

APCI-MS (m/z): 482(M+H)+

Example 342

To a solution of 4-(3-chloro-4-methoxybenzylamino)-5-[2-(4-resin-methoxy-3-bromophenyl)ethoxycarbonyl]-6-chloro-2-methylthiopyrimidine (prepared in Example 326 (4)) 1.20 g in tetrahydrofuran 8 ml is gradually added a solution of 28% sodium methoxide/methanol 229 mg in tetrahydrofuran 3 ml at room temperature. The mixture is stirred for 2 hours. After filtration the resin is washed with tetrahydrofuran and dimethylformamide. The filtrate and washed solution is diluted with a 10% aqueous citric acid solution and neutralized with an aqueous saturated sodium hydrogen carbonate solution. The solution is extracted with ethyl acetate. The ethyl acetate layer is washed, dried and concentrated in vacuo to give 4-(3-chloro-4-methoxybenzylamino)-5-methoxycarbonyl-6-methoxy-2-methylthiopyrimidine as a colorless caramel, 293 mg. mp 124–126° C.

(2) A mixture of 4-(3-chloro-4-methoxybenzylamino)-5-methoxycarbonyl-6-methoxy-2-methylthiopyrimidine (prepared in the above (1)) 271 mg, a 2.0M aqueous sodium hydroxide solution 3.53 ml, water 2 ml and dimethyl sulfoxide 6 ml is stirred at 65° C. for 14 hours. After cooling the reaction mixture is neutralized with a 10% aqueous citric acid solution and extracted with ethyl acetate. The ethyl acetate layer is washed, dried and concentrated in vacuo and the resulting powder is triturated with isopropyl ether to give 4-(3-chloro-4-methoxybenzylamino)-5-carboxy-6-methoxy-2-methylthiopyrimidine as a colorless crystalline powder, 210 mg. mp 167–170° C.

(3) To a mixture of 4-(3-chloro-4-methoxybenzylamino)-5-carboxy-6-methoxy-2-methylthiopyrimidine (prepared in the above (2)) 183 mg, 2-aminomethylpyrimidine 70 mg, 1-hydroxybenzotriazole hydrate 67 mg and dimethylformamide 4 ml is added 1-(3-dimethylaminopropyl)-3-ethylcarbodiimido hydrochloride 114 mg on an ice bath, and the mixture is stirred for 14 hours at room temperature. The reaction mixture is diluted with an aqueous sodium hydrogen carbonate solution and extracted with ethyl acetate. The ethyl acetate layer is washed, dried and concentrated in vacuo. The residue is separated with silica gel chromatography (solvent; chloroform:ethyl acetate=20:1→10:1) to give 4-(3-chloro-4-methoxybenzylamino)-5-[N-(2-pyrimidinylmethyl)carbamoyl]-6-methoxy-2-methylthiopyrimidine as a colorless crystalline powder 208 mg. mp 171–172° C.

(4) 4-(3-Chloro-4-methoxybenzylamino)-5-[N-(2-pyrimidinylmethyl)carbamoyl]-6-methoxy-2-methylthiopyrimidine (prepared in the above (3)) is treated in the same manner as Example 321(4) to give 4-(3-chloro-4-methoxybenzylamino)-5-[N-(2-pyrimidinylmethyl)carbamoyl]-6-methoxy-2-methylsulfinylpyrimidine as a colorless powder.

(5) 4-(3-Chloro-4-methoxybenzylamino)-5-[N-(2-pyrimidinylmethyl)carbamoyl]-6-methoxy-2-methylsulfinylpyrimidine (prepared in the above (4)) and L-prolinol is treated in the same manner as Example 321(5) to give 4-(3-chloro-4-methoxybenzylamino)-5-[N-(2-pyrimidinylmethyl)carbamoyl]-6-methoxy-2-(2-hydroxymethyl-1-pyrrolodinyl)pyrimidine as a colorless crystalline powder 88 mg. mp 153–154° C.

Example 343

(1) 4,6-Dichloro-5-carboxy-2-methylthiopyrimidine prepared in Example 320(1) and 2-bromo-4-(2-hydroxyethyl)phenol prepared in Example 326(1) are treated in the same manner as Example 326(3) and (4) to give 5-[2-(4-resin-methoxy-3-bromophenyl)ethoxycarbonyl]-4,6-chloro-2-methylthiopyrimidine.

(2) 5-[2-(4-Resin-methoxy-3-bromophenyl)ethoxycarbonyl]-4,6-chloro-2-methylthiopyrimidine prepared in the above (1) and 2-(3,4-dimethoxyphenyl)ethylamine 254 mg (0.892 mmol/g) are suspended in dimethylformamide 1 ml, and thereto is added triethylamine 23 mg. To the mixture is added a solution of 3,4-dimethoxyphenethylamine 41 mg in dimethylformamide 1 ml. The mixture is stirred for 23 hours at room temperature. The reacted resin is filtered, washed with dimethylformamide, hydrous dimethylformamide, methanol, tetrahydrofuran, isopropyl ether, respectively several times, and then dried in vacuo to give 4-(2-(3,4-dimethoxyphenyl)ethylamino-5-[2-(4-resin-methoxy-3-bromophenyl)ethoxycarbonyl]-6-chloro-2-methylthiopyrimidine 279 mg.

(3) 4-(2-(3,4-Dimethoxyphenyl)ethylamino-5-[2-(4-resin-methoxy-3-bromophenyl)ethoxycarbonyl]-6-chloro-2-methylthiopyrimidine (prepared in the above (2)) 237 mg is suspended in dimethylformamide 2.5 ml. Thereto is added triethylamine 81 μl and 4-hydroxypiperidine 59 mg and the mixture is stirred for 14 hours at room temperature. The reacted resin is filtered, washed with dimethylformamide, hydrous dimethylformamide, methanol and dichloromethane, respectively several times, and then dried to give 4-(2-(3,4-dimethoxyphenyl)ethylamino)-5-[2-(4-resin-methoxy-3-bromophenyl)ethoxycarbonyl]-6-(4-hydroxypiperidin-1-yl)-2-methylthiopyrimidine.

(4) 4-(2-(3,4-Dimethoxyphenyl)ethylamino)-5-[2-(4-resin-methoxy-3-bromophenyl)ethoxycarbonyl]-6-(4-hydroxypiperidine-1-yl)-2-methylthiopyrimidine prepared in the above (3) is suspended in dichloromethane 2.5 ml. After swelling m-chloroperbenzoic acid 119 mg is added thereto and the mixture is stirred for 9 hours at room temperature. The reacted resin is filtered, washed with dichloromethane, dimethylacetamide and methanol, respectively several times, and then dried to give 4-(2-(3,4-dimethoxyphenyl)ethylamino)-5-[2-(4-resin-methoxy-3-bromophenyl)ethoxycarbonyl]-6-(4-hydroxypiperidin-1-yl)-2-methylsulfinylpyrimidine.

(5) 4-(2-(3,4-Dimethoxyphenyl)ethylamino)-5-[2-(4-resin-methoxy-3-bromophenyl)ethoxycarbonyl]-6-(4-hydroxypiperidin-1-yl)-2-methylsulfinylpyrimidine prepare in the above (4) is suspended in dimethylacetamide 2.5 ml, and thereto are added triethylamine 108 µl and L-prolinol 76 µl. The mixture is stirred for 9 hours at 75° C. The reacted resin is filtered, washed with dimethylacetamide and tetrahydrofuran, respectively several times, and then dried to give 4-(2-(3,4-dimethoxyphenyl)ethylamino)-5-[2-(4-resin-methoxy-3-bromophenyl)ethoxycarbonyl]-6-(4-hydroxypiperidin-1-yl)-2-(2-hydroxymethyl-1-pyrrolidinyl)pyrimidine.

(6) 4-(2-(3,4-Dimethoxyphenyl)ethylamino)-5-[2-(4-resin-methoxy-3-bromophenyl)ethoxycarbonyl]-6-(4-hydroxypiperidin-1-yl)-2-(2-hydroxymethyl-1-pyrrolidinyl)pyrimidine prepared in the above (5) is suspended in tetrahydrofuran 2 ml, and thereto is added 28% sodium methoxide/methanol 370 mg. The mixture is stirred at 55° C. for 2.5 hours. After filtration the resin is washed with tetrahydrofuran. The filtrate is diluted with a 10% aqueous citric acid solution and made weakly alkaline with an aqueous saturated sodium hydrogen carbonate solution. The solution is extracted with methylene chloride. The combined organic layer is washed with an aqueous saturated sodium chloride solution, dried over anhydrous magnesium sulfate and concentrated in vacuo. The residue is separated and purified with silica gel chromatography (eluate; chloroform:ethyl acetate=1:1→ethyl acetate) to give 4-(2-(3,4-dimethoxyphenyl)ethylamino)-5-methoxycarbonyl-6-(4-hydroxypiperidin-1-yl)-2-(2-hydroxymethyl-1-pyrrolidinyl)pyrimidine as a colorless foam, 20 mg.

APCI-MS(m/z): 516(M+H)$^+$

Example 344

(1) A mixture of dimethyl N-cyanodithioiminocarbonate 3.21 g, L-prolinol 2.31 g and chloroform 22 ml is stirred at room temperature for a day. After reaction the mixture is separated with silica gel chromatography (solvent; hexane:ethyl acetate=1:3→ethyl acetate) to give a compound 1.65 g. mp 44–48° C.

(2) To a mixture of 1-mercaptacetic acid ethyl ester 1.06 ml and triethylamine 9 ml is added the compound (prepared in the above (1)) 1.46 g at room temperature, and the mixture is stirred for a day. After reaction triethylamine is distilled off and the residue is separated with silica gel chromatography (solvent; hexane:ethyl acetate=1:4) to give 4-amino-5-ethoxycarbonyl-2-(2-hydroxymethyl-1-pyrrolodinyl)thiazole as a colorless viscous oil, 197 mg.

IR (Neat)cm$^{-1}$: 3441, 3324, 1656, 1613, 1545, 1509
APCI-MS(m/z): 272(M+H)$^+$ (3) To a mixture of 4-amino-5-ethoxycarbonyl-2-(2-hydroxymethyl-1-pyrrolodinyl)thiazole (prepared in the above (2)) 177 mg, 3-chloro-4-methoxybenzaldehyde 111 mg, acetic acid 78 mg and 1,2-dichloroethane 8 ml is added sodium triacetoxyborohydride 415 mg, and the mixture is stirred at room temperature for 6 hours. Further 3-chloro-2 5 4-methoxybenzaldehyde 111 mg and sodium triacetoxyborohydride 415 mg are added thereto, and the mixture is stirred at room temperature for 3 days. The reaction mixture is diluted with an aqueous sodium hydrogen carbonate solution and the organic layer is washed, dried and concentrated in vacuo. The residue is separated with reversed phase column chromatography and preparative thin-layer chromatography, and then triturated with ether to give 4-(3-chloro-4-methoxybenzylamino)-5-ethoxycarbonyl-2-(2-hydroxymethyl-1-pyrrolodinyl)thiazole as crystals, 171 mg. mp 103.5–104.5° C.

Example 345

(1) A solution of carbobenzoxychloride 7.87 g in methylene chloride 50 ml is dropped to a mixture of L-prolinol 4.9 g in methylene chloride 50 ml and sodium hydrogen carbonate 11.6 g in water 50 ml at 0° C. under vigorously agitation. The mixture is stirred for 1 hour at room temperature. The organic layer is separated, washed, dried and concentrated in vacuo to give N-carbobenzoxy-L-prolinol 10.25 g.

(2) To a mixture of N-carbobenzoxy-L-prolinol (prepared in the above (1)) 5.26 g, diisopropylamine 45 ml and dimethylformamide 22 ml is dropped methoxymethyl chloride 4.1 g at 0° C., and the mixture is stirred for 3 days at room temperature. The reaction mixture is diluted with water and extracted with ethyl acetate. The organic layer is neutralized with 10% hydrochloric acid, washed, dried and concentrated in vacuo. The residue is separated with silica gel chromatography (solvent; hexane:ethyl acetate=2:1) to N-carbobenzoxy-2-methoxymethoxymethylpyrrolidine 3.944 g.

(3) To a solution of N-carbobenzoxy-2-methoxymethoxymethylpyrrolidine (prepared in the above (2)) 3.9 g in methanol 80 ml is added palladium-carbon 1 g at argon atmosphere. Hydrogen gas is blown through the mixture and the mixture is stirred at room temperature for 3 hours. After reaction catalyst is removed by filtration and the filtrate is concentrated in vacuo to give 2-methoxymethoxymethylpyrrolidine 2.02 g.

(4) A mixture of 2-methoxymethoxymethylpyrrolidine (prepared in the above (3)) 2 g, cyanoisothiocyanate dimethylacetal 2.24 g and chloroform 20 ml is stirred at room temperature for 24 hours. The reaction mixture is concentrated in vacuo and the residue is separated with silica gel chromatography (solvent; hexane:ethyl acetate=1:1) to give N-cyano-2-methoxymethoxymethylpyrrolidinethiocarboimidic acid methyl ester 2.746 g.

(5) To a mixture of 1-mercaptacetic acid 1 g and trifluoroacetic acid 5 ml is added triphenylmethanol 2.8 g, and the mixture is stirred at room temperature for 1 hour. After reaction trifluoroacetic acid is distilled off and the residue is separated with silica gel chromatography (solvent; chloroform) and triturated with hexane to give 1-(triphenylmethylthio)acetic acid 1.233 g. mp 155–158° C.

(6) A mixture of 1-(triphenylmethylthio)acetic acid (prepared in the above (5)) 1.218 g, 2-aminomethylpyrimidine 517 mg, 1-hydroxybenzotriazole hydrate 540 mg, 1-(3-dimethylaminopropyl)-3-ethylcarbodiimide hydrochloride 768 mg and dimethylformamide 15 ml is stirred at room temperature overnight. The reaction mixture is diluted with ethyl acetate and an aqueous sodium hydrogen carbonate solution, and extracted with ethyl acetate. The organic layer is washed, dried and concentrated in vacuo. The residue is triturated with ether to give N-(2-pyrimidinylmethyl)-1-(triphenylmethylthio)acetamide 1.416 g.

mp 171–173° C.

(7) To a mixture of N-(2-pyrimidinylmethyl)-1-(triphenylmethylthio)acetamide 990 mg, trifluoroacetic acid 5 ml and methylene chloride 5 ml is dropped triethylsilane 1.35 g at 0° C., and the mixture is stirred for 5 minutes. The reaction mixture is concentrated in vacuo and the residue is separated with silica gel chromatography (solvent; chloroform:methanol=80:1→25:1) to give N-(2-pyrimidinylmethyl)-1-mercaptoacetamide 451 mg.

(8) A mixture of a compound (prepared in the above (4)) 515 mg, N-(2-pyrimidinylmethyl)-1-mercaptoacetamide (prepared in the above (7)) 427 mg and triethylamine 6 ml is stirred at room temperature for 20 hours. The reaction mixture is further stirred at 60–70° C. for 5 hours. The mixture is concentrated in vacuo and the residue is separated with silica gel chromatography (solvent; chloroform:methanol=80:1) to give 4-amino-5-[N-(2-pyrimidinylmethyl)amido]-2-(2-methoxymethoxymethyl-1-pyrrolidinyl)thiazole 457 mg.

(9) To a mixture of 4-amino-5-[N-(2-pyrimidinylmethyl)amido]-2-(2-methoxymethoxymethyl-1-pyrrolidinyl)thiazole (prepared in the above (8)) 345 mg, 3-chloro-4-methoxybenzaldehyde 401 mg, acetic acid 141 mg and 1,2-dichloroethane 14 ml is added sodium triacetoxyborohydride 798 mg, and the mixture is stirred overnight at room temperature. The reaction mixture is diluted with water and extracted with ethyl acetate. The organic layer is washed, dried and concentrated in vacuo. The residue is separated with reverse phase column chromatography to give 4-(3-chloro-4-methoxybenzylamino)-5-[N-(2-pyrimidinylmethyl)amido]-2-(2-methoxymethoxymethyl-1-pyrrolidinyl)thiazole 334 mg.

(10) To a mixture of 4-(3-chloro-4-methoxybenzylamino)-5-[N-(2-pyrimidinylmethyl)amido]-2-(2-methoxymethoxymethyl-1-pyrrolidinyl)thiazole (prepared in the above (9)) 334 mg and methanol 4 ml is added concentrated hydrochloric acid 2 ml, and the mixture is stirred at room temperature for 2 hours. The reaction mixture is diluted with chloroform and an aqueous sodium hydrogen carbonate solution and extracted with chloroform. The organic layer is dried and concentrated in vacuo. The residue is separated with silica gel chromatography (solvent; chloroform:methanol=50:1) to give 4-(3-chloro-4-methoxybenzylamino)-5-[N-(2-pyrimidinylmethyl)amido]-2-(2-hydromethyl-1-pyrrolidinyl)thiazole 213 mg.

IR (Neat)cm$^{-1}$: 3316, 2929, 2871, 1603, 1563, 1543, 1503
FAB-MS(m/z): 489(M+H)$^+$ Example 346

(1) 4-(3-Chloro-4-methoxybenzylamino)-5-[2-(4-resin-methoxy-3-bromophenyl)ethoxycarbonyl-6-(N-methyl-2-hydroxyethylamino)-2-methylsulfinylpyrimidine and 5,6,7,8-tetrahydroimidazo[1,2-a]pyrazine are treated in the same manner as Examples 468–476(3) to give 4-(3-chloro-4-methoxybenzylamino)-5-[2-(4-resin-methoxy-3-bromophenyl)ethoxycarbonyl-6-(N-methyl-2-hydroxyethylamino)-2-(5,6,7,8-tetrahydroimidazo[1,2-a]pyrazin-7-yl)pyrimidine.

(2) 4-(3-Chloro-4-methoxybenzylamino)-5-[2-(4-resin-methoxy-3-bromophenyl)ethoxycarbonyl-6-(N-methyl-2-hydroxyethylamino)-2-(5,6,7,8-tetrahydroimidazo[1,2-a]pyrazin-7-yl)pyrimidine (prepared in the above (1)) is treated in the same manner as Example 327–335(4) to 4-(3-chloro-4-methoxybenzylamino)-2-(5,6,7,8-tetrahydroimidazo[1,2-a]pyrazin-7-yl)-9-methyl-8,9-dihydro-7H-pyrido[4,5-e][1,4]oxazepin-5-one.

APCI-MS(m/z): 470(M+H)$^+$

Example 347

(1) 2-Bromo-4-(2-hydroxyethyl)phenoxymethyl-resin (prepared in Example 326(2)) (1.27 mmol/g) 30.00 g is suspended in anhydrous methylene chloride 25 ml. While triethylamine 13.28 g is added thereto and the mixture is stirred, acryloyl chloride 6.19 ml is dropped thereto under ice cooling in argon atmosphere over a period of 15 minutes. The reaction mixture is stirred at room temperature for 14 hours. The reacted resin compound is filtered, washed with methylene chloride, dimethylformamide, hydrous dimethylformamide, methanol, tetrahydrofuran and isopropyl ether, respectively several times, and dried in vacuo to give 2-bromo-4-(2-acryloyloxyethyl)phenoxymethyl-resin 35.78 g.

(2) 2-Bromo-4-(2-acryloyloxyethyl)phenoxymethyl-resin (prepared in the above (1)) 35.09 g is suspended in a mixture of tetrahydrofuran 200 ml, dimethyl sulfoxide 80 ml and ethanol 40 ml. To the suspension are added triethylamine 10.37 ml and 4-methoxy-3-chlorobenzylamine hydrochloride 15.49 g, and the mixture is stirred at 60° C. for 22 hours. The reacted resin compound is filtered, washed with tetrahydrofuran, dimethylformamide, hydrous dimethylformamide, methanol and isopropyl ether, respectively several times, and dried in vacuo to give 2-bromo-4-(2-(3-(4-methoxy-3-chlorobenzylamino)propionyloxy)ethyl)phenoxymethyl-resin 38.93 g.

(3) A mixture of 4,6-dichloro-5-carboxy-2-methylthiopyrimidine (prepared in Example 320(1)) 5.00 g, N,N-dimethylacetamide 50 ml, tetrahydrofuran 20 ml and sodium hydride (60%) 1.673 g is stirred for 20 minutes on an ice bath. Methanol 5 ml is dropped thereto over a period of 30 minutes and the mixture is stirred for 15 minutes. The reaction mixture is diluted with a 10% aqueous citric solution and extracted with ethyl acetate. The organic layer is washed, dried and concentrated in vacuo. The resulting solid is triturated with hexane in ice to give 4-chloro-5-carboxy-6-methoxy-2-methylthiopyrimidine as a slightly brown crystalline powder, 4.61 g. mp 179–181° C.

(4) A mixture of 4-chloro-5-carboxy-6-methoxy-2-methylthiopyrimidine (prepared in the above (3)) 2.00 g and thionyl chloride 5 ml is stirred at 40° C. for 15 minutes. Thionyl chloride, etc. is distilled off and the solvent is removed with azeotrope with methylene chloride to give 4-chloro-5-chloroformyl-6-methoxy-2-methylthiopyrimidine.

(5) To a mixture of whole amount of 4-chloro-5-chloroformyl-6-methoxy-2-methylthiopyrimidine (prepared in the above (4)) and methylene chloride 10 ml is dropped a mixture of 2-aminomethylpyrimidine 930 mg, triethylamine 2.38 ml and methylene chloride 10 ml over a period of 5 minutes on an ice bath, and the mixture is stirred for 20 minutes. The mixture is further stirred at room temperature for 40 minutes. The reaction mixture is diluted with water and the water layer is extracted with methylene chloride. The organic layer is dried and concentrated in vacuo. The residue is separated with silica gel chromatography (solvent; chloroform:ethyl acetate 1:1) and recrystallized from a mixture of methylene chloride, ethyl acetate and isopropyl ether to give 4-chloro-5-[N-(2-pyrimidinylmethyl)carbamoyl]-6-methoxy-2-methylthiopyrimidine as a colorless crystalline powder, 1.56 g. mp 176–177° C.

(6) 2-Bromo-4-(2-(3-(4-methoxy-3-chlorobenzylamino) propionyloxy)ethyl)phenoxymethyl-resin (prepared in the above (2)) 400 mg is suspended in N,N-dimethylacetamide 3.5 ml. To the suspension are added triethylamine 107 μl and 4-chloro-5-[N-(2-pyrimidinylmethylcarbamoyl]-6-methoxy-2-methylthiopyrimidine (prepared in the above (5)) 249 mg, and the mixture is stirred at 70° C. for 17 hours. The reacted resin compound is filtered, washed with N,N-dimethylformamide, hydrous N,N-dimethylformamide, methanol, tetrahydrofuran and methylene chloride, respectively several times, and dried in vacuo to give 4-[N-(4-methoxy-3-chlorobenzyl)-N-[2-(4-resin-methoxy-3-bromophenethyloxycarbonyl)ethyl]amino]-5-[N-(2-pyrimidinylmethyl)carbamoyl]-6-methoxy-2-methylthiopyrimidine.

(7) The resin compound (prepared in the above (6)) is suspended in methylene chloride 2.5 ml. To the suspension is added a solution of m-chloroperbenzoic acid 104 mg in methylene chloride 1 ml, and the mixture is stirred at room temperature for 16 hours. The reacted resin compound is filtered, washed with hydrous N,N-dimethylformamide, methanol, methylene chloride and N,N-dimethylacetamide, respectively several times, to give 4-[N-(4-methoxy-3-chlorobenzyl)-N-[2-(4-resin-methoxy-3-bromophenethyloxycarbonyl)ethyl]amino]-5-[N-(2-pyrimidinylmethyl)carbamoyl]-6-methoxy-2-methylsulfinylpyrimidine.

(8) The resin compound prepared in the above (7) is suspended in N,N-dimethylacetamide 2.5 ml. To the suspension are added triethylamine 160 μl and L-prolinol 116 mg and then the mixture is stirred at 75° C. for 14 hours. The reacted resin compound is filtered, washed with N,N-dimethylformamide, hydrous N,N-dimethylformamide, methanol, tetrahydrofuran and a mixture of tert-butanol and tetrahydrofuran (1:9), respectively several times, to give 4-[N-(4-methoxy-3-chlorobenzyl)-N-[2-(4-resin-methoxy-3-bromophenethyloxycarbonyl)ethyl]amino]-5-[N-(2-pyrimidinylmethyl)carbamoyl]-6-methoxy-2-(2-hydroxymethyl-1-pyrrolidinyl)pyrimidine.

(9) The resin compound (prepared in the above (8)) is suspended in a mixture of tert-butanol and tetrahydrofuran (1:9). To the suspension is added tert-potassium butoxide 214 mg under ice cooling. The mixture is stirred for 20 minutes. A 10% aqueous citric acid solution 2 ml is added thereto and the resin is filtered, washed with tetrahydrofuran. The washed solution is made basic with an aqueous saturated sodium hydrogen carbonate solution and extracted with ethyl acetate. The combined organic layer is washed with an aqueous sodium chloride solution, dried over magnesium sulfate and concentrated in vacuo. The residue is separated and purified with preparative thin-layer silica gel chromatography (eluent; chloroform:ethyl acetate: methanol=20:20:1) and recrystallized from a mixture of ethanol and isopropyl ether to give 4-(4-methoxy-3-chlorobenzylamino)-5-[N-(2-pyrimidinylmethyl)carbamoyl]-6-methoxy-2-(2-hydroxymethyl-1-pyrrolidinyl)pyrimidine as a colorless crystalline powder, 28 mg. mp 153–154° C.

Examples 348–354

(1) The following compounds are prepared in the same manner in Example 347(3) and (4).

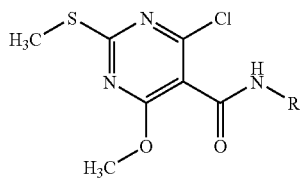

TABLE 21

| | R | mp |
|---|---|---|
| 348-1 | 2-ethylpyridin-yl | 120–122° C. |
| 349-1 | propyl-O-CH₃ | 133–134° C. |
| 350-1 | trans-4-hydroxycyclohexyl | 195–197° C. |
| 351-1 | 2-ethyl-5-methylpyrazinyl | 155–156° C. |
| 352-1 | 3-ethyl-2-methylpyridinyl | 155–158° C. |
| 353-1 | 2-methyl-3-methylpyridinyl | 193–195° C. |
| 354-1 | 3-(morpholin-4-yl)propyl | 109–112° C. |

(2) The following compounds are prepared starting from the compounds prepared in the above (1) in the same manner as Example 347(6).

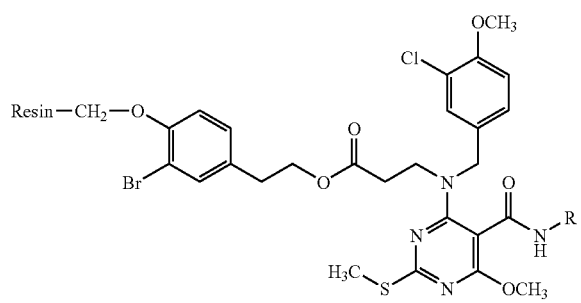

TABLE 22
| | R |
|---|---|
| 348-2 | 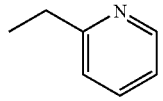 |
| 349-2 | 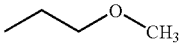 |
| 350-2 | 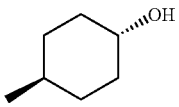 |
| 351-2 | 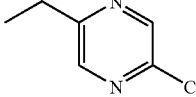 |
| 352-2 | 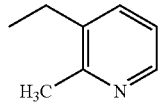 |
| 353-2 | 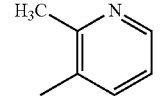 |
| 354-2 | 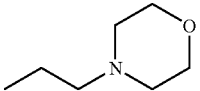 |
Examples 355–394
The compounds listed in the following Tables 23–30 are prepared starting from the compounds prepared in the above (2) and Example 347 (5) in the same manner as Example 347(6)–(8).
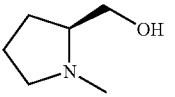
TABLE 23
| Example No. | $R^1$ |
|---|---|
| 355 | 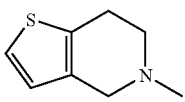 |
| 356 | 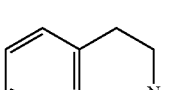 |
| 357 | 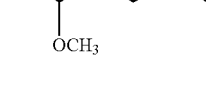 |
| 358 | 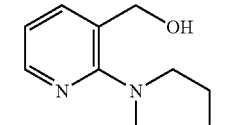 |
| 359 | 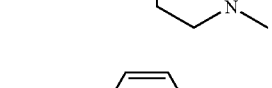 |
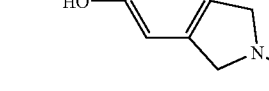
TABLE 24
| Example No. | $R^1$ |
|---|---|
| 360 | 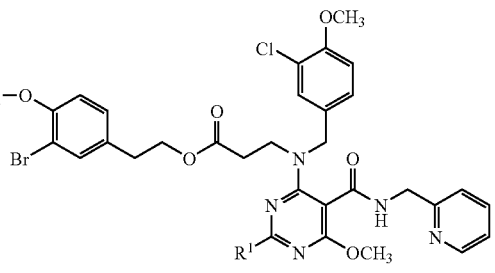 |
| 361 | 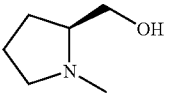 |
| 362 | 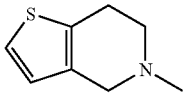 |

TABLE 24-continued

| Example No. | R¹ |
|---|---|
| 363 | (7-methyl-5,6,7,8-tetrahydroimidazo[1,2-a]pyrazin-yl) |
| 364 | (6-hydroxy-2-methylisoindolin-yl) |

[Structure: Resin-OCH2-C6H3(Br)-CH2CH2-O-C(=O)-CH2CH2-N(CH2-C6H3(Cl)(OCH3))-pyrimidine(R¹)(OCH3)-C(=O)-NH-CH2CH2-OMe]

TABLE 25

| Example No. | R¹ |
|---|---|
| 365 | ((S)-1-methylpyrrolidin-2-yl)methanol |
| 366 | (5-methyl-4,5,6,7-tetrahydrothieno[3,2-c]pyridinyl) |
| 367 | (8-methoxy-2-methyl-1,2,3,4-tetrahydroisoquinolinyl) |
| 368 | (7-methyl-5,6,7,8-tetrahydroimidazo[1,2-a]pyrazinyl) |
| 369 | (2-dimethylamino-4-(4-methylpiperazin-1-yl)pyrimidinyl) |

[Structure: Resin-CH2-O-C6H3(Br)-CH2CH2-O-C(=O)-CH2CH2-N(CH2-C6H3(Cl)(OCH3))-pyrimidine(R¹)(OCH3)-C(=O)-NH-cyclohexyl-OH]

TABLE 26

| Example No. | R¹ |
|---|---|
| 370 | ((S)-1-methylpyrrolidin-2-yl)methanol |
| 371 | (5-methyl-4,5,6,7-tetrahydrothieno[3,2-c]pyridinyl) |
| 372 | (8-methoxy-2-methyl-1,2,3,4-tetrahydroisoquinolinyl) |
| 373 | (7-methyl-5,6,7,8-tetrahydroimidazo[1,2-a]pyrazinyl) |
| 374 | (2-dimethylamino-4-(4-methylpiperazin-1-yl)pyrimidinyl) |

[Structure: Resin-CH2-O-C6H3(Br)-CH2CH2-O-C(=O)-CH2CH2-N(CH2-C6H3(Cl)(OCH3))-pyrimidine(R¹)(OCH3)-C(=O)-NH-CH2-(5-methylpyrazin-2-yl)]

TABLE 27

| Example No. | R¹ |
|---|---|
| 375 | ((S)-1-methylpyrrolidin-2-yl)methanol |

TABLE 27-continued
| Example No. | R¹ |
|---|---|
| 376 | 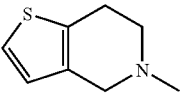 |
| 377 | 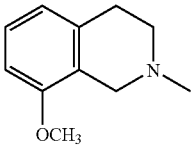 |
| 378 | 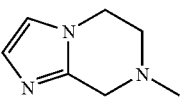 |
| 379 | 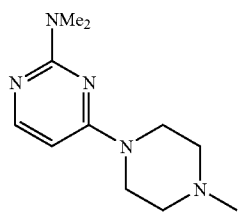 |
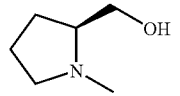
TABLE 28
| Example No. | R¹ |
|---|---|
| 380 | 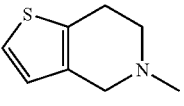 |
| 381 | 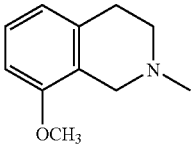 |
| 382 | 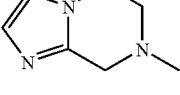 |
| 383 | 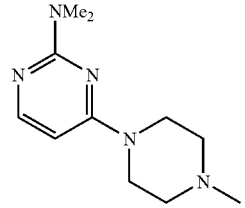 |
TABLE 28-continued
| Example No. | R¹ |
|---|---|
| 384 | 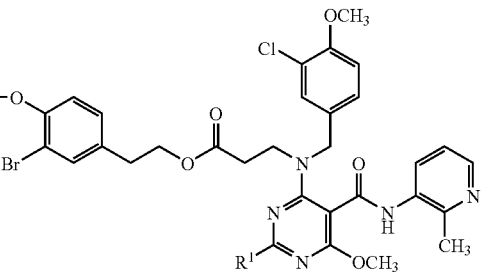 |
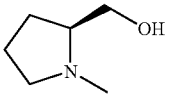
TABLE 29
| Example No. | R¹ |
|---|---|
| 385 | 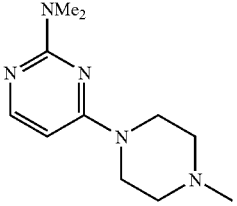 |
| 386 | |
| 387 | |
| 388 | |
| 389 | |

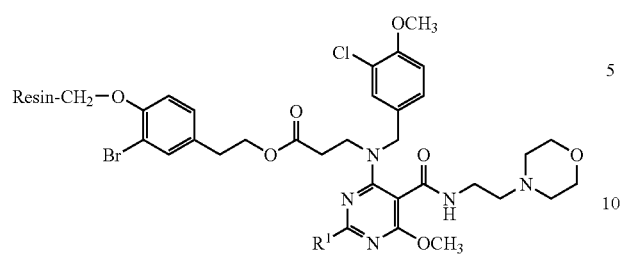

TABLE 30

| Example No. | R¹ |
|---|---|
| 390 | (S)-1-methyl-2-(hydroxymethyl)pyrrolidinyl |
| 391 | 5-methyl-4,5,6,7-tetrahydrothieno[3,2-c]pyridinyl |
| 392 | 8-methoxy-2-methyl-1,2,3,4-tetrahydroisoquinolinyl |
| 393 | 7-methyl-5,6,7,8-tetrahydroimidazo[1,2-a]pyrazinyl |
| 394 | 2-(dimethylamino)-6-(4-methylpiperazin-1-yl)pyrimidin-4-yl |

Examples 395–432

The compounds listed in the following Tables 31–39 are prepared by removing the resin from the compounds prepared in Example 347 (5) and Examples 355–395 in the same manner as Example 347(9).

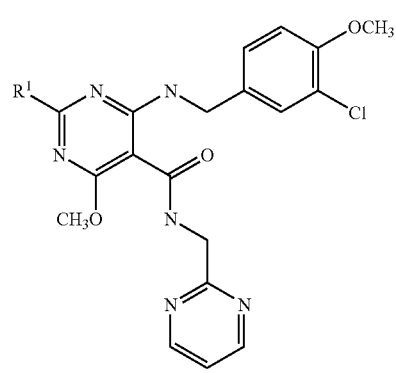

TABLE 31

| Example No. | R¹ | Physical property etc. |
|---|---|---|
| 395 | (S)-1-methyl-2-(hydroxymethyl)pyrrolidinyl | mp: 153–154° C. APCI-MS(m/z): 514 (M + H)⁺ |
| 396 | 5-methyl-4,5,6,7-tetrahydrothieno[3,2-c]pyridinyl | mp: 152–155° C. APCI-MS(m/z): 552 (M + H)⁺ |
| 397 | 8-methoxy-2-methyl-1,2,3,4-tetrahydroisoquinolinyl | mp: 169–172° C. APCI-MS(m/z): 576 (M + H)⁺ |
| 398 | 2-(4-methylpiperazin-1-yl)-3-(hydroxymethyl)pyridinyl | Foam APCI-MS(m/z): 606 (M + H)⁺ |

TABLE 32

| Example No. | Product | Physical property etc. |
|---|---|---|
| 399 | 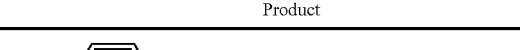 | mp: 186–188° C. APCI-MS(m/z): 456 (M + H)⁺ |

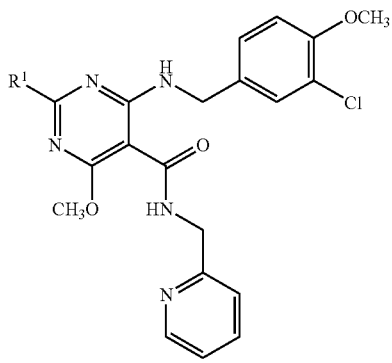

TABLE 33

| Example No. | R¹ | Physical property etc. |
|---|---|---|
| 400 | (S)-1-methylpyrrolidin-2-yl-methanol | Foam APCI-MS (m/z): 513 (M + H)⁺ |
| 401 | 5-methyl-4,5,6,7-tetrahydrothieno[3,2-c]pyridin-2-yl | mp: 153–155° C. APCI-MS (m/z): 551 (M + H)⁺ |
| 402 | 8-methoxy-2-methyl-1,2,3,4-tetrahydroisoquinolin-... | mp: 137–139° C. APCI-MS (m/z): 575 (M + H)⁺ |
| 403 | A mixture of 5-hydroxy-isoindolin-2-yl and 5-methoxy-isoindolin-2-yl | mp: 198–201° C. APCI-MS (m/z): 547 (M + H)⁺ |

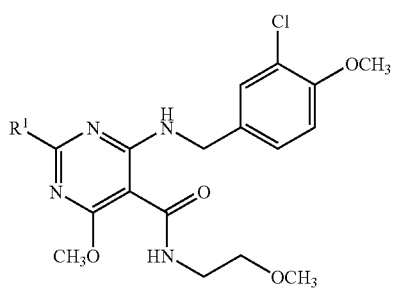

TABLE 34

| Example No. | R¹ | Physical property etc. |
|---|---|---|
| 404 | (S)-1-methylpyrrolidin-2-yl-methanol | Oil APCI-MS (m/z): 480 (M + H)⁺ |
| 405 | 5-methyl-4,5,6,7-tetrahydrothieno[3,2-c]pyridin-2-yl | Oil APCI-MS (m/z): 518 (M + H)⁺ |
| 406 | 8-methoxy-2-methyl-1,2,3,4-tetrahydroisoquinolin-yl | mp: 93–96° C. APCI-MS (m/z): 542 (M + H)⁺ |
| 407 | HO— | mp: 216–218° C. APCI-MS (m/z): 397 (M + H)⁺ |
| 408 | 2-(dimethylamino)-4-(4-methylpiperazin-1-yl)pyrimidin-yl | mp: 71–73° C. APCI-MS (m/z): 586 (M + H)⁺ |

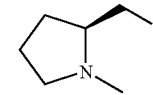

TABLE 35

| Example No. | R¹ | Physical property etc. |
|---|---|---|
| 409 | (S)-1-methylpyrrolidin-2-yl-methanol | Foam APCI-MS(m/z): 520 (M + H)⁺ |
| 410 | 5-methyl-4,5,6,7-tetrahydrothieno[3,2-c]pyridin-2-yl | Oil APCI-MS(m/z): 558 (M + H)⁺ |
| 411 | 8-methoxy-2-methyl-1,2,3,4-tetrahydroisoquinolin-yl | Foam APCI-MS(m/z): 582 (M + H)⁺ |
| 412 | nBuO— | Oil APCI-MS(m/z): 493 (M + H)⁺ |

TABLE 35-continued

| Example No. | R¹ | Physical property etc. |
|---|---|---|
| 413 | 2-(NMe₂)pyrimidin-4-yl-N-methylpiperazinyl | Oil APCI-MS(m/z): 626 (M + H)⁺ |
| 414 | HO— | mp 216–218° C. APCI-MS(m/z): 437 (M + H)⁺ |

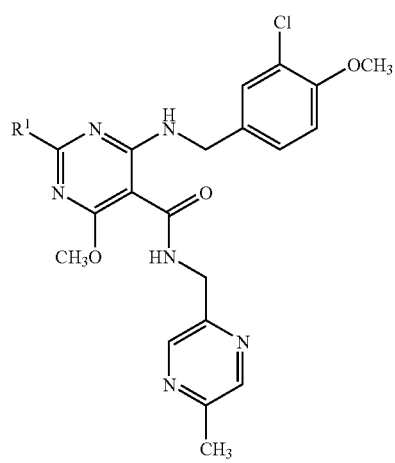

TABLE 36

| Example No. | R¹ | Physical property etc. |
|---|---|---|
| 415 | (1-methylpyrrolidin-2-yl)methanol | Foam APCI-MS(m/z): 528(M + H)⁺ |
| 416 | 5-methyl-4,5,6,7-tetrahydrothieno[3,2-c]pyridin-5-yl | mp 140–142° C. APCI-MS(m/z): 566(M + H)⁺ |
| 417 | 8-methoxy-2-methyl-1,2,3,4-tetrahydroisoquinolin-2-yl | mp 163–165° C. APCI-MS(m/z): 590(M + H)⁺ |
| 418 | nBuO— | mp 98–101° C. APCI-MS(/z): 501(M + H)⁺ |

TABLE 36-continued

| Example No. | R¹ | Physical property etc. |
|---|---|---|
| 419 | 2-(NMe₂)pyrimidin-4-yl-N-methylpiperazinyl | mp 193–194° C. APCI-MS(m/z): 634(M + H)⁺ |

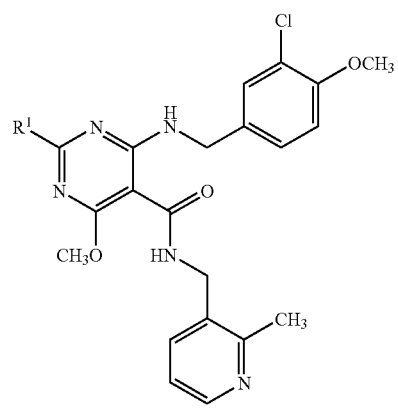

TABLE 37

| Example No. | R¹ | Physical property etc. |
|---|---|---|
| 420 | (1-methylpyrrolidin-2-yl)methanol | Foam APCI-MS(m/z): 527(M + H)⁺ |
| 421 | 2-(NMe₂)pyrimidin-4-yl-N-methylpiperazinyl | mp 172–173° C. APCI-MS(m/z): 565(M + H)⁺ |
| 422 | 8-methoxy-2-methyl-1,2,3,4-tetrahydroisoquinolin-2-yl | mp 86–88° C. APCI-MS(m/z): 589(M + H)⁺ |
| 423 | CH₃S— | mp 160–162° C. APCI-MS(m/z): 474(M + H)⁺ |

TABLE 37-continued

| Example No. | R¹ | Physical property etc. |
|---|---|---|
| 424 | NMe₂-pyrimidin-4-yl-(4-methylpiperazin-1-yl) | mp 182–184° C. APCI-MS(m/z): 633(M + H)⁺ |

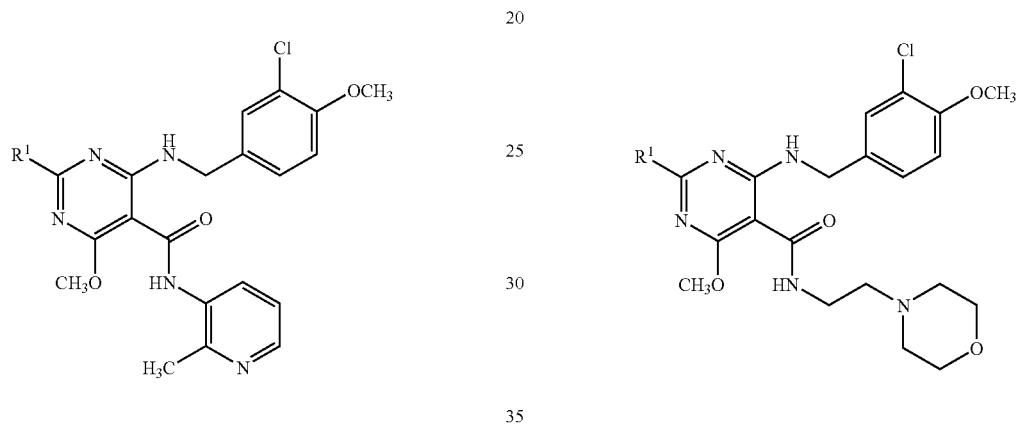

TABLE 38

| Example No. | R¹ | Physical property etc. |
|---|---|---|
| 425 | (1-methylpyrrolidin-2-yl)methanol | Foam APCI-MS(m/z): 513 (M + H)⁺ |
| 426 | 5-methyl-4,5,6,7-tetrahydrothieno[3,2-c]pyridine | Foam APCI-MS(m/z): 551 (M + H)⁺ |
| 427 | 8-methoxy-2-methyl-1,2,3,4-tetrahydroisoquinoline | APCI-MS(m/z): 575(M + H)⁺ mp 187–192° C. |
| 428 | 7-methyl-5,6,7,8-tetrahydroimidazo[1,2-a]pyrazine | Foam APCI-MS(m/z): 535 (M + H)⁺ |

TABLE 38-continued

| Example No. | R¹ | Physical property etc. |
|---|---|---|
| 429 | NMe₂-pyrimidin-4-yl-(4-methylpiperazin-1-yl) | Foam APCI-MS(m/z): 619 (M + H)⁺ |

TABLE 39

| Example No. | R¹ | Physical property etc. |
|---|---|---|
| 430 | (1-methylpyrrolidin-2-yl)methanol | Oil APCI-MS(m/z): 535(M + H)⁺ |
| 431 | 5-methyl-4,5,6,7-tetrahydrothieno[3,2-c]pyridine | Oil APCI-MS(m/z): 573(M + H)⁺ |
| 432 | 8-methoxy-2-methyl-1,2,3,4-tetrahydroisoquinoline | Oil APCI-MS(m/z): 597(M + H)⁺ |

Examples 433–482

The compounds listed in the following Table 15 are prepared as mentioned above.

TABLE 15

| Example No. | Structure | Physical property etc. |
|---|---|---|
| 433 | 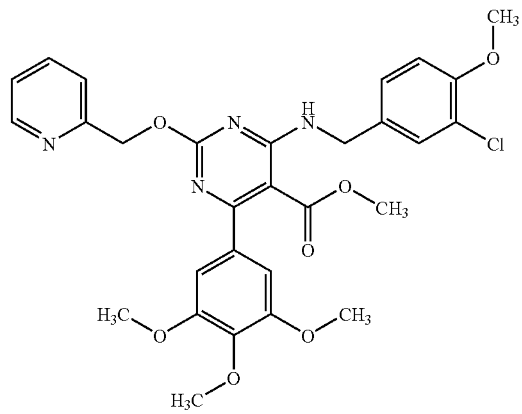 | mp 158–162° C. |
| 434 | 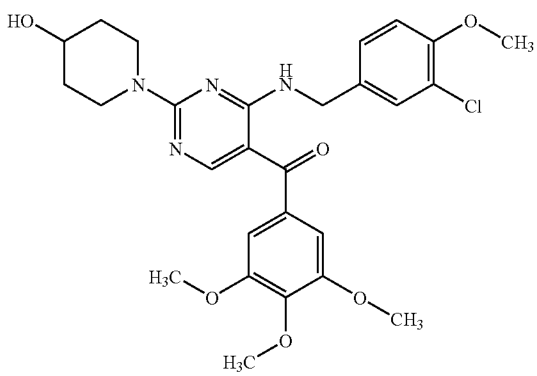 | mp 132–133° C. |
| 435 | 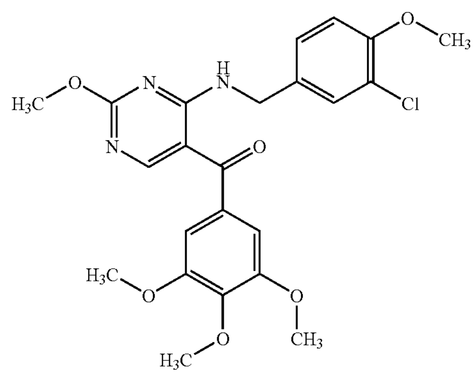 | mp 136–138° C. |
| 436 | 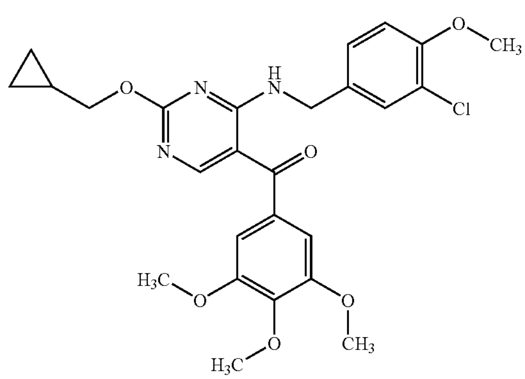 | mp 98–100° C. |

TABLE 15-continued

| Example No. | Structure | Physical property etc. |
|---|---|---|
| 437 | 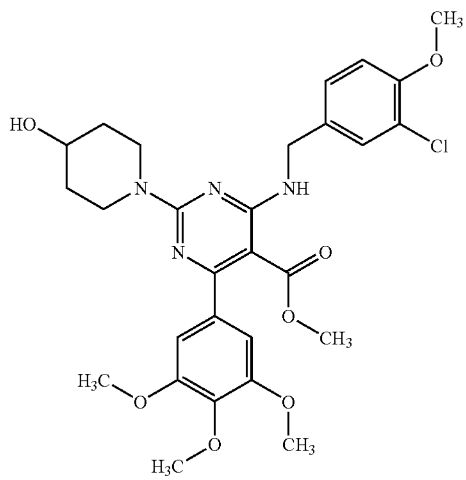 | mp 169–171° C. |
| 438 | 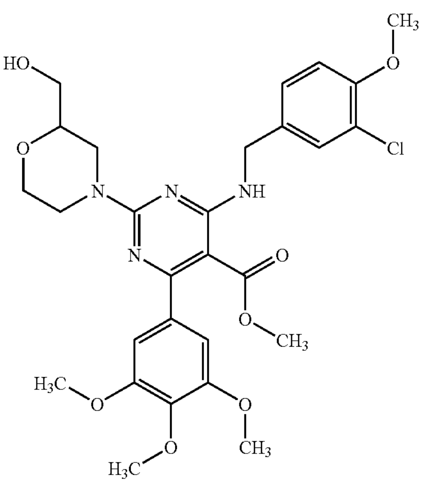 | Foam<br>MS(m/z): 589(M + H)$^+$ |
| 439 | 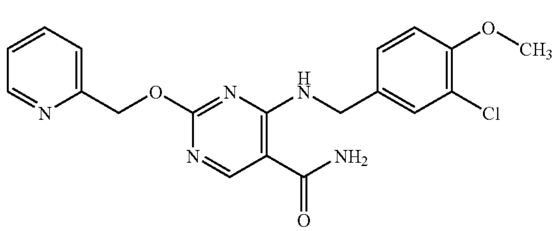 | mp 208–209° C. |

TABLE 15-continued

| Example No. | Structure | Physical property etc. |
|---|---|---|
| 440 | 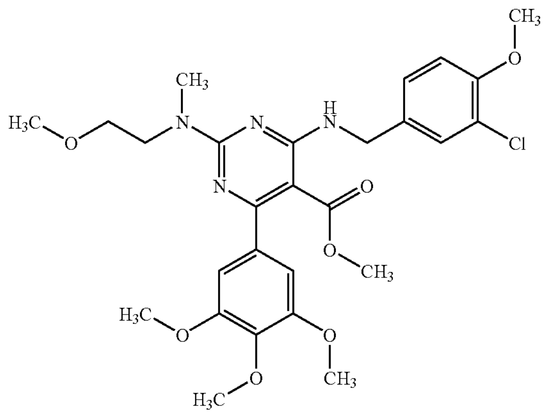 | Foam MS(m/z): 561(M + H)+ |
| 441 | 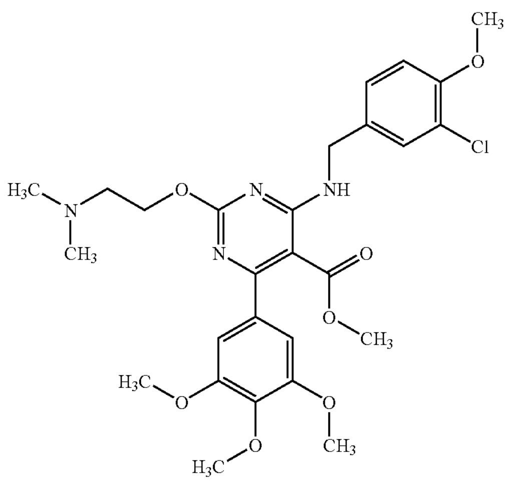 | Foam MS(m/z): 561(M + H)+ |
| 442 | 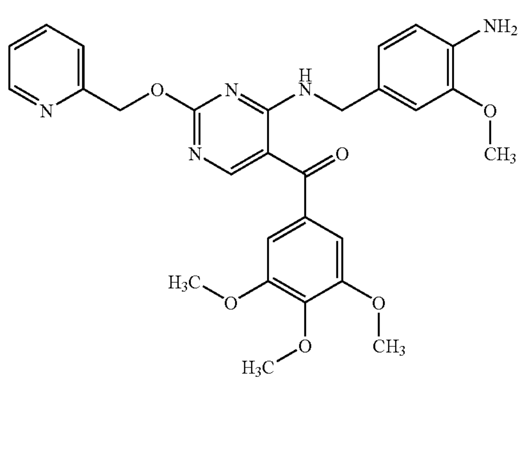 | mp 146–148° C. |

TABLE 15-continued

| Example No. | Structure | Physical property etc. |
|---|---|---|
| 443 | 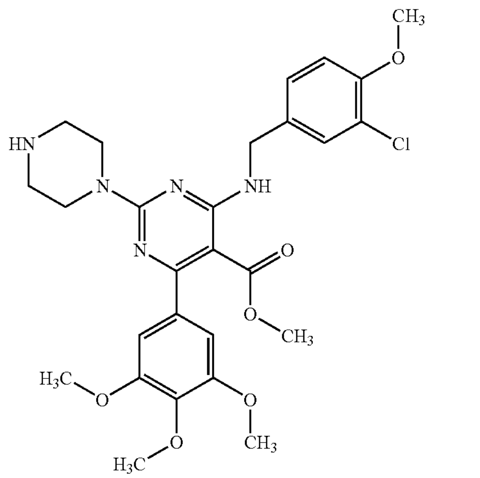 | mp 153–155° C. |
| 444 | 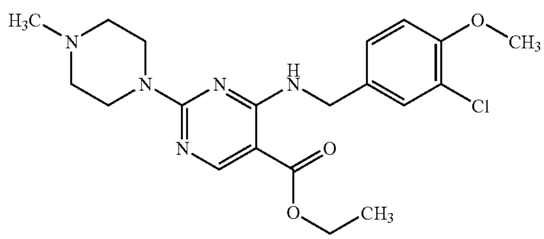 | mp 136.5–137.5° C. |
| 445 | 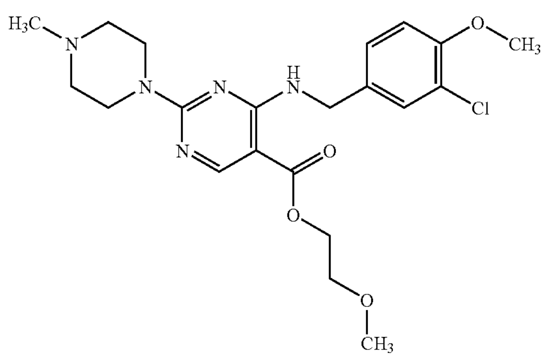 | mp 112.5–113° C. |
| 446 | 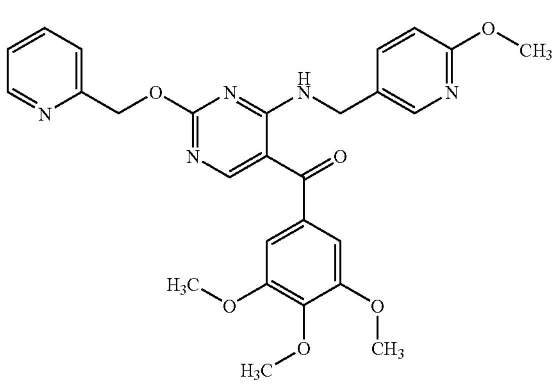 | mp 42–45° C. |

TABLE 15-continued

| Example No. | Structure | Physical property etc. |
|---|---|---|
| 447 | 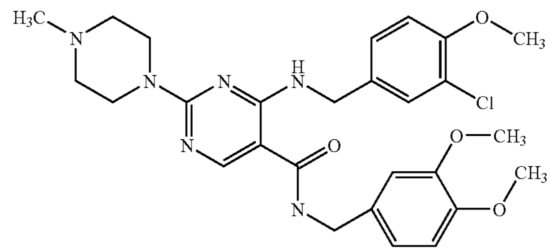 | D.c. 90–130° C. |
| 448 | 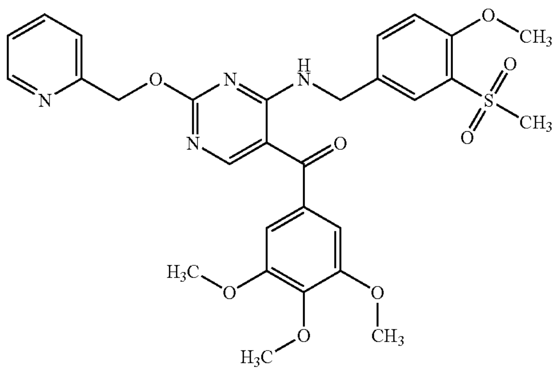 | Amorphous MS(m/z): 595(M + H)+ |
| 449 | 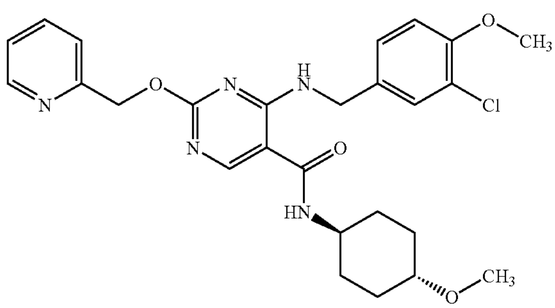 | mp 139–140° C. |
| 450 | 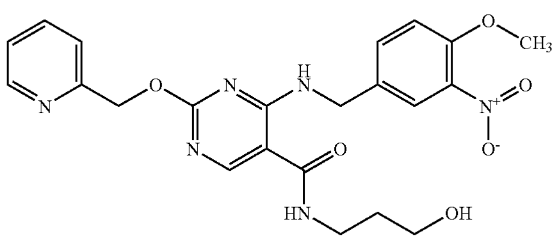 | mp 142–145° C. |
| 451 | 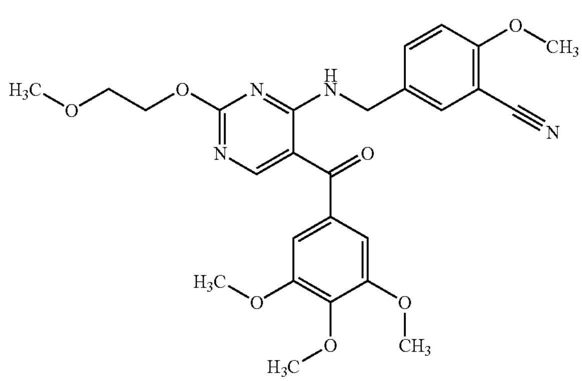 | mp 149–150° C. |

TABLE 15-continued

| Example No. | Structure | Physical property etc. |
|---|---|---|
| 452 | 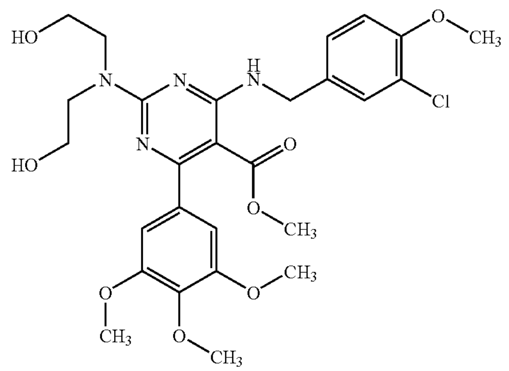 | D.c. 86–90° C. |
| 453 | 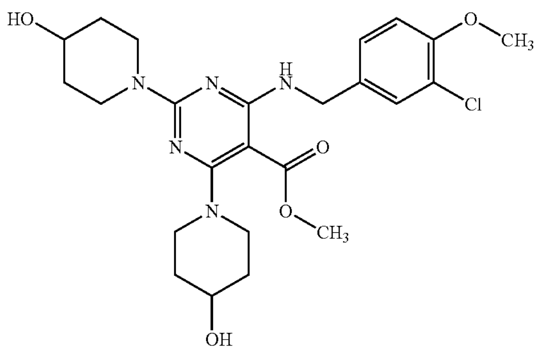 | Powder MS(m/z): 506(M + H)+ |
| 454 | 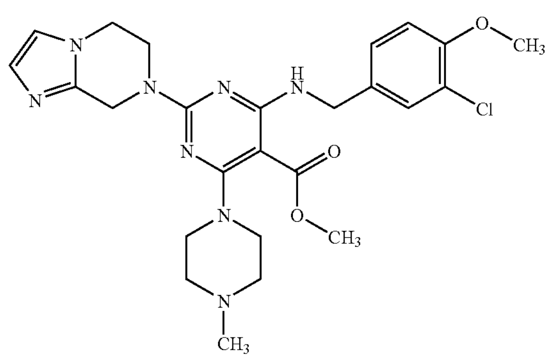 | Oil MS(m/z): 527(M + H)+ |
| 455 | 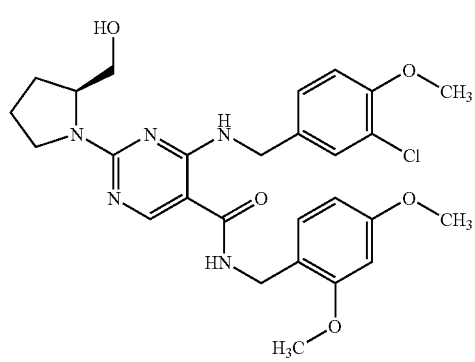 | Foam MS(m/z): 542(M + H)+ |

TABLE 15-continued

| Example No. | Structure | Physical property etc. |
| --- | --- | --- |
| 456 | 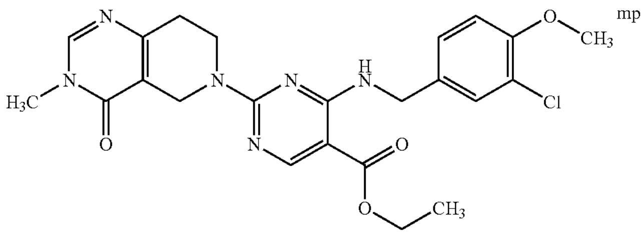 | mp 185–188° C. |
| 457 | 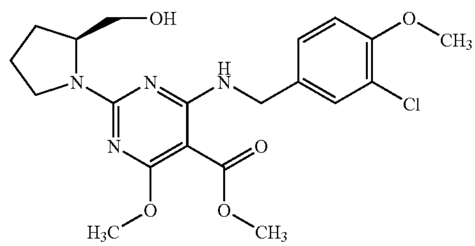 | Foam<br>MS(m/z): 437(M + H)⁺ |
| 458 | 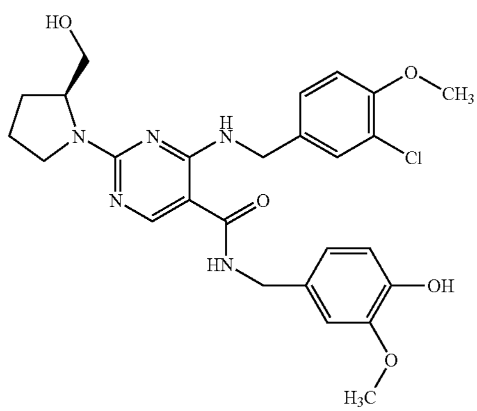 | Powder<br>MS(m/z): 528(M + H)⁺ |
| 459 | 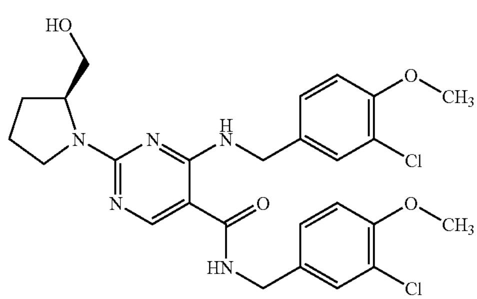 | mp 158–160° C. |
| 460 | 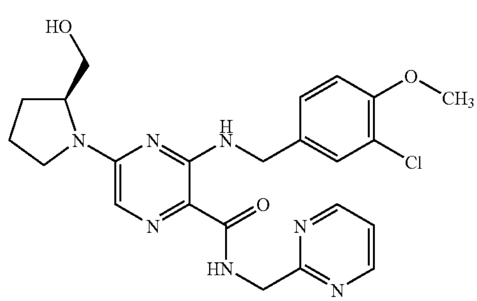 | Hydrochloride<br>Powder<br>MS(m/z): 484(M + H)⁺ |

TABLE 15-continued

| Example No. | Structure | Physical property etc. |
| --- | --- | --- |
| 461 | 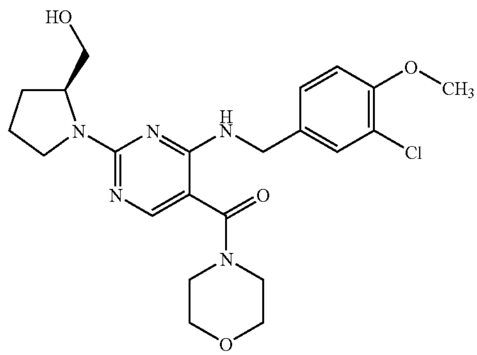 | Powder<br>MS(m/z): 462(M + H)⁺ |
| 462 | 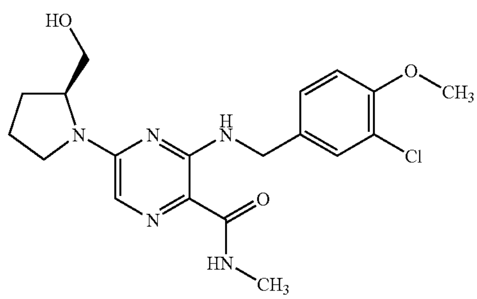 | mp 191–193° C. |
| 463 | 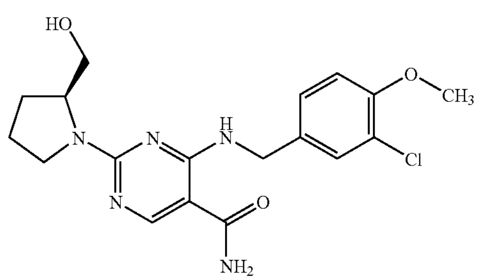 | mp 152.5–154.5° C. |
| 464 | 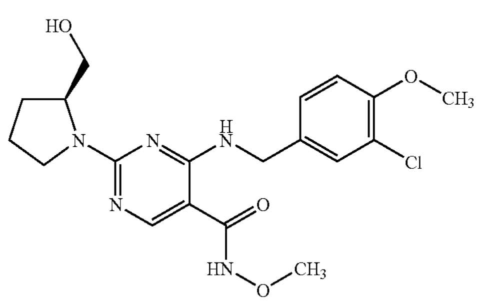 | mp 155–157° C. |

TABLE 15-continued

| Example No. | Structure | Physical property etc. |
|---|---|---|
| 465 | 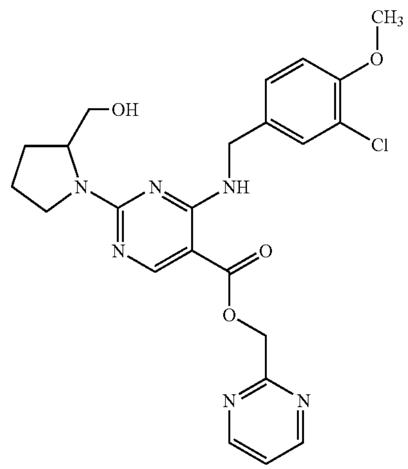 | mp 146–147° C. |
| 466 | 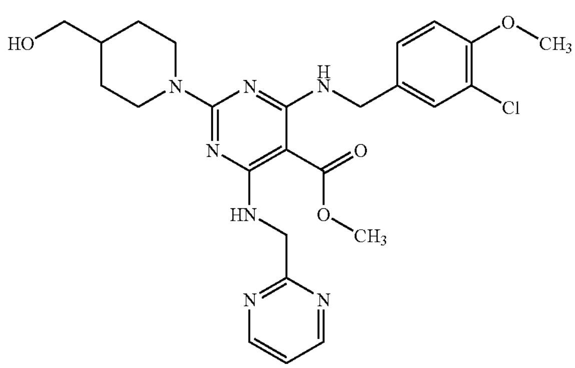 | MS(m/z): 528(M + H)+ mp 97° C. |
| 467 | 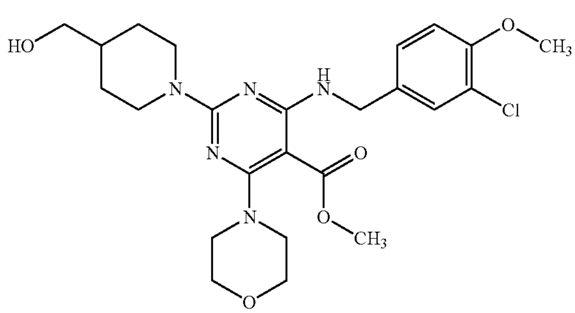 | Foam MS(m/z): 506(M + H)+ |
| 468 | 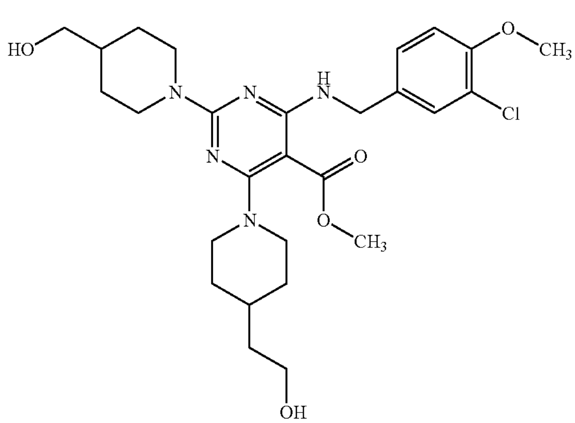 | Foam MS(m/z): 548(M + H)+ |

TABLE 15-continued

| Example No. | Structure | Physical property etc. |
|---|---|---|
| 469 | 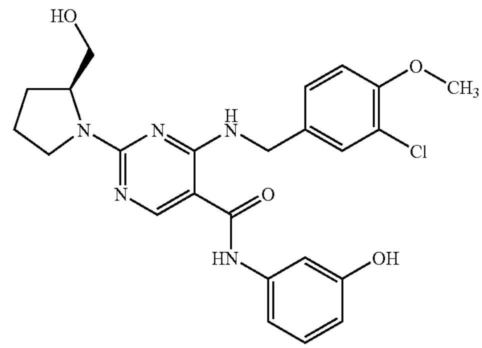 | mp 214–215° C. |
| 470 | 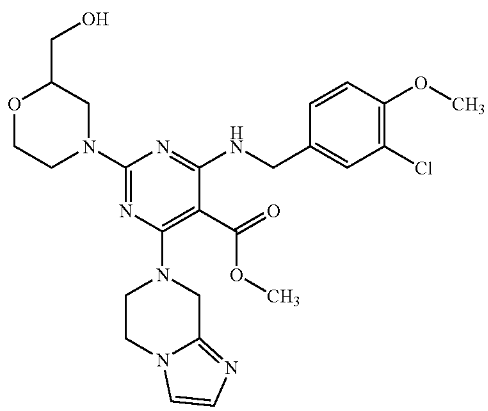 | Foam MS(m/z): 544(M + H)+ |
| 471 | 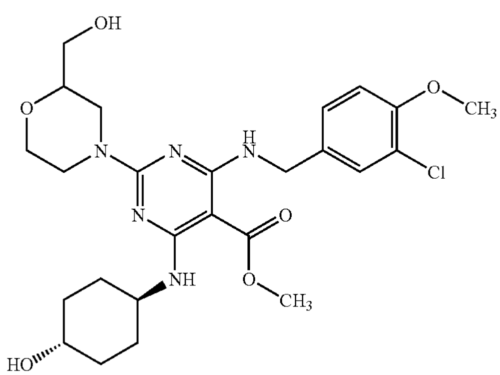 | mp 176–182° C. |
| 472 | 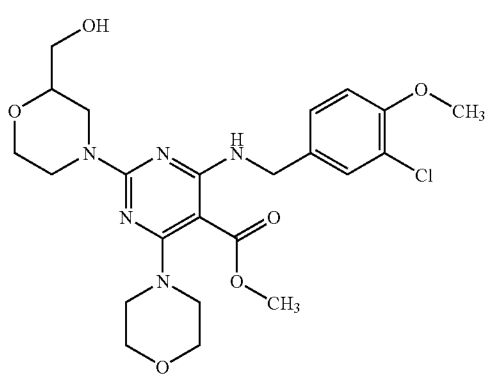 | Foam MS(m/z): 508(M + H)+ |

TABLE 15-continued
| Example No. | Structure | Physical property etc. |
|---|---|---|
| 473 | 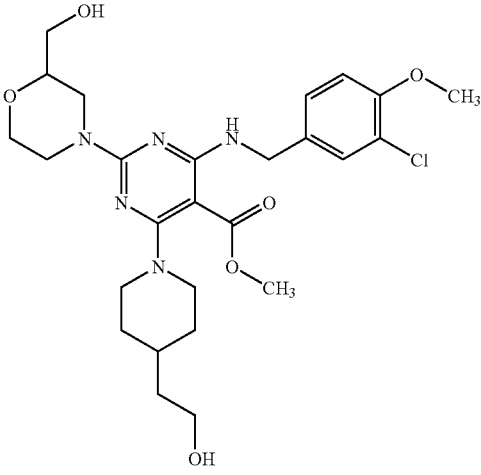 | Foam<br>MS(m/z): 548(M + H)+ |
| 474 | 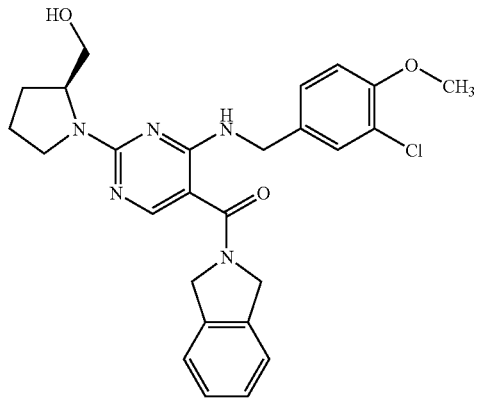 | Powder<br>MS(m/z): 494(M + H)+ |
| 475 | 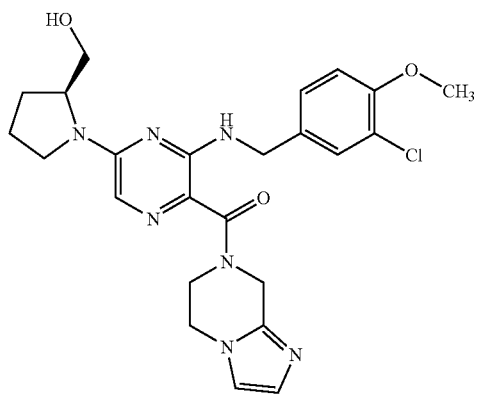 | Powder<br>MS(m/z): 498(M + H)+ |

TABLE 15-continued

| Example No. | Structure | Physical property etc. |
|---|---|---|
| 476 | 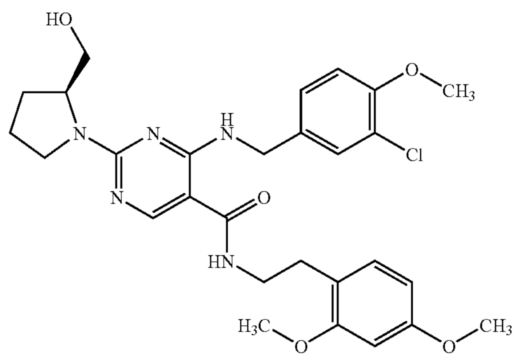 | Powder<br>MS(m/z): 556(M + H)+ |
| 477 | 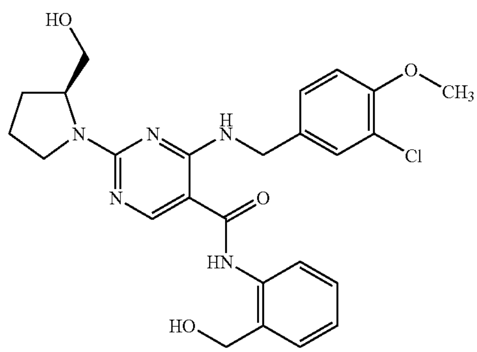 | Powder<br>MS(m/z): 498(M + H)+ |
| 478 | 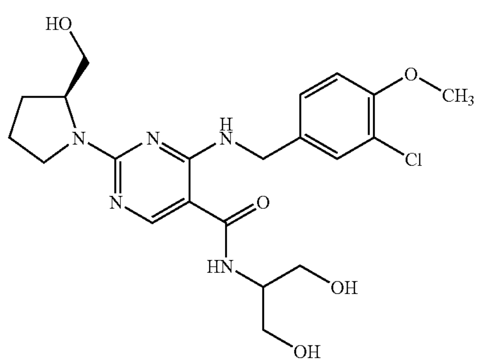 | mp 184–185° C. |
| 479 | 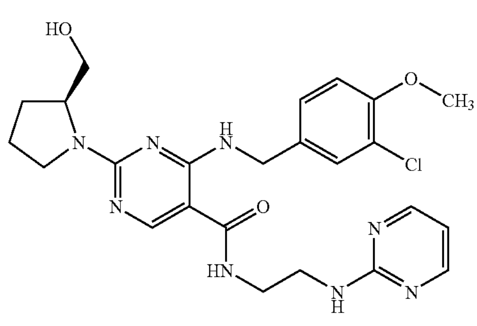 | mp 146–148° C. |

TABLE 15-continued

| Example No. | Structure | Physical property etc. |
|---|---|---|
| 480 | 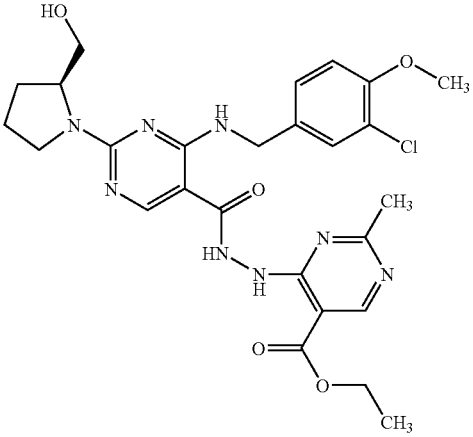 | mp 208–209° C. |
| 481 | 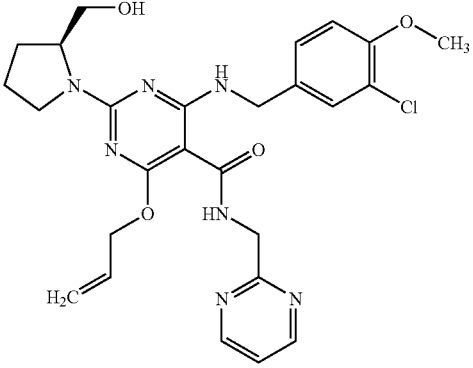 | mp 123–126° C. |
| 482 | 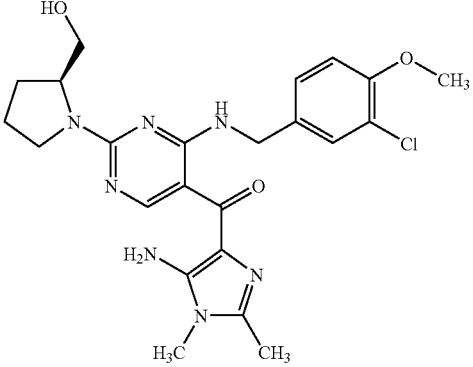 | Powder MS(m/z): 486(M + H)+ |

Reference Example (1) A solution of 2-cyanopyrimidine 80 g in ethanol 400 ml is put in a 5L autoclave, and therein are 10% palladium-carbon 48 g in ethanol and 15% ammonia/ethanol (ammonia 224 g, 1.6 L). After the atmosphere is three times substituted with 3 hydrogen pressure, the reaction is carried out at 7 hydrogen pressure for 5 hours. The mixture is filtered with precoated active carbon 40 g and washed with ethanol. The solvent is removed under atmospheric pressure. To the residue is added ethanol and then gradually added maleic acid 97.2 g and the mixture is stirred for 1 hour. To the mixture is dropped ethyl acetate 800 ml over about a period of about 20 minutes. The mixture is gradually cooled to 30° C., and is stirred for 30 minutes under ice cooling. The resulting crystals are collected by filtration, washed with a mixture of ethanol and ethyl acetate (1:2) 160 ml to give 2-aminomethylpyrimidine maleate 114.6 g (yield: 67%).

(2) 2-Aminomethylpyrimidine maleate 70 g and ethanol 280 ml are put in a 4 neck-flask (2 L). To the suspension is dropped a solution of hydrogen chloride in ethanol (previously prepared) 69.6 g over a period of 10 minutes, and the mixture is stirred at 70° C. for 2 hours. After reaction ethyl acetate 560 ml is dropped thereto at 60° C. and the mixture is gradually cooled to 30° C. and stirred for 30 minutes under ice cooling. The resulting crystals are collected by filtration, washed with a cold mixture of ethanol and ethyl acetate (1:2) 140 ml and dried to give 2-aminomethylpyrimidine hydrochloride as powder-like crystals 43.1 g. mp 207–210 (decomposition)

INDUSTRIAL APPLICABILITY

The compound (I) of the present invention and its pharmacologically acceptable salt have excellent specific PDE V inhibitory activity and therefore, are effective for treating various diseases due to functional disorders on cGMP-signaling, such as chronic or acute heart failure, myocardial infarction, erectile dysfunction, hypertension, pulmonary hypertension, diabetic gastroparesis, angina pectoris, female sexual dysfunction, prostatic hyperplasia, asthema, diarrhea, constipation, achalasia, etc.

The compound (I) of the present invention and its pharmacologically acceptable salt have excellent characteristic properties as they hardly show side effects including toxicity, exhibit selectively the desired effect and are safe as a medicine.

The invention claimed is:

1. A cyclic compound of the formula (I) or a pharmacologically acceptable salt thereof,

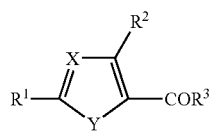

(I)

wherein X is =N—,
Y is —N=CH—,
$R^1$ is
 (1) a lower alkoxy group which is optionally substituted by one to three, same or different, substituents selected from the group consisting of a cyclo lower alkyl group, a hydroxy group, a lower alkylamino group which is optionally protected, a lower alkoxy group, a hydroxy-substituted lower alkyl group, a phenyl group, a lower alkoxyphenyl group, a hydroxy-substituted lower alkylphenyl group, a furyl group, a pyridyl group, a lower alkoxypyridyl group, a hydroxy-substituted lower alkylpyridyl group, a lower alkylpyridyl group, a pyrimidinyl group, a lower alkoxypyrimidinyl group, or a morpholinyl group,
 (2) a lower alkylamino group which is optionally substituted by one to three, same or different, substituents selected from the group consisting of a hydroxy group, a lower alkoxy group, a lower alkyl group, a pyridyl group, a lower alkylamino group, a cyano group, a phenyl group which is optionally substituted by a lower alkoxy group and/or a halogen atom, or a hydroxy-substituted lower alkyl group,
 (3) an indanylamino group,
 (4) a hydroxy group which is optionally substituted by a pyridyl group, or
 (5) a cyano group,
$R^2$ is
 (1) a lower alkylamino group substituted by an aryl group which is optionally substituted by one to four, same or different, substituents selected from the group consisting of a lower alkoxy group, a halogen atom, an amino group, a lower alkanoylamino group, a formylamino group, a hydroxy group, a lower alkoxypyridyl group, a lower alkylamino group, a nitro group, a halogeno-substituted lower alkyl group, a lower alkylenedioxy group, a cyano group, a lower alkyl group substituted by a hydroxy group which is optionally protected, a lower alkylsulfonyl group, or a lower alkylsulfinyl group,
 (2) a lower alkoxy group substituted by one to four, same or different, substituents selected from the group consisting of a lower alkoxy group or a halogen atom,
 (3) a lower alkoxy group substituted by a pyridyl group,
 (4) a lower alkylamino group substituted by an indolyl group, a pyrimidinyl group, a benzofuranyl group, a dihydrobenzofuranyl group, a lower alkylpyrimidinyl group, a dihydrobenzoxazolyl or a dihydrobenzimidazolyl group, or
 (5) an indanylamino group, and
$R^3$ is
 (1) an aryl group which is optionally substituted by one to four, same or different, substituents selected from the group consisting of a lower alkoxy group and an lower alkylamino group, or an aryl group which is optionally substituted by one or two lower alkylenedioxy groups,
 (2) a heterocyclic ring containing N atom(s) which is optionally substituted by one to four, same or different, substituents selected from the group consisting of a lower alkyl group, a hydroxy group, an amino group, a chlorosulfinyloxy group and a piperidinyloxysulfinyloxy group,
 (3) a lower alkyl group which is optionally substituted by one to three, same or different, substituents selected from the group consisting of a morpholinyl group and a di-lower alkoxyphosphoryl group,
 (4) a lower alkoxy group which is optionally substituted by one to three, same or different, substituents selected from the group consisting of a pyridyl group, a lower alkoxypyridyl group, a pyrimidinyl group, a lower alkylamino group, a pyrazinyl group, a lower alkoxy group which is optionally substituted by a phenyl group, a pyrimidinyl-substituted oxy group, a pyridyl-substituted oxy group, a pyrimidinyl-substituted lower alkoxy group, a morpholinyl group, a lower alkylmorpholinyl group, a N-lower alkyl-N-pyrimidinylamino group, a lower alkyldioxolanyl group, a lower alkoxy-substituted lower alkoxy group, a pyridylcarbonylamino group, a hydroxy group, and a lower alkylpiperidyl group,
 (5) a cyclo lower alkoxy group which is optionally substituted by a hydroxy group, or
 (6) a piperidyl-substituted hydroxy group which is optionally substituted by one to four, same or different, substituents selected from the group consisting of a pyrimidinyl group, a lower alkyl group and a cyano-substituted lower alkyl group.

2. The compound claimed in claim 1, wherein an aryl group on $R^2$ or $R^3$ is a monocyclic, bicyclic or tricyclic 6–14 membered aryl group which may be partially saturated, or a heterocyclic ring containing N atom(s) on $R^3$ is a monocyclic or bicyclic 5 to 14 membered heterocyclic containing N atom(s).

3. The compound claimed in claim 2, wherein the monocyclic, bicyclic or tricyclic 6–14 membered aryl group which may be partially saturated on $R^2$ or $R^3$ is phenyl, naphthyl, indenyl or indanyl.

4. The compound claimed in claim 2, wherein the monocyclic or bicyclic 5 to 14 membered heterocyclic ring containing N atom(s) on $R^3$ is pyridyl, pyrimidinyl, imidazolyl, piperidyl, pyrazolyl, morpholinyl, piperazinyl, pyrrolidinyl, dihydroisoindolyl, tetrahydroimidazo[1,2-a]pyrazyl, tetrahydroisoquinolyl, dihydro-5H-pyrrolo[3,4-b]pyridyl, naphthylidinyl, pyrazo[3,4-d]pyridyl, tetrahydropyridyl, oxazolo[4,5-c]pyridyl, octahydropyrido[3,4-d]pyrimidinyl, thiazolo[4,5-d]pyridyl, imidazo[4,5-d]pyridyl, perhydrodiazepinyl, perhydropiperadino[3,4-c]piperadinyl, tetrahydroisoxazolo[4,5-c]pyridyl, hexahydropyrazolo[4,3-c]pyridyl, dihydropyridyl, tetrahydroxazolo[5,4-c]pyridyl, hexahydropyrido[3,4-d]pyrimidinyl, octahydropyrido[4,3-d]pyrimidinyl, tetrahydrothiazolo[5,4-c]pyridyl, imidazo[4,5-b]pyridyl, homopiperazinyl, perhydropyrazino[1,2-a]pyrazinyl, tetrahydropyrido[4,3-d]pyrimidinyl, tetrahydrothieno[3,2-c]pyridyl, or tetrahydronaphthylidinyl.

5. A pharmaceutical composition containing a compound claimed in claim 1, or its pharmacologically acceptable salt as an active ingredient.

6. A method for treating erectile dysfunction, comprising administering to a patient in need thereof an effective amount of a compound claimed in claim 1, or its pharmacologically acceptable salt.

7. A method for treating pulmonary hypertension, comprising administering to a patient in need thereof an effective amount of a compound claimed in claim 1, or its pharmacologically acceptable salt.

8. A method for treating diabetic gastroparesis comprising administering to a patient in need thereof an effective amount of a compound claimed in claim 1, or its pharmacologically acceptable salt.

* * * * *